(12) United States Patent
Agrawal et al.

(10) Patent No.: US 7,713,535 B2
(45) Date of Patent: May 11, 2010

(54) MODULATION OF IMMUNOSTIMULATORY PROPERTIES BY SMALL OLIGONUCLEOTIDE-BASED COMPOUNDS

(75) Inventors: Sudhir Agrawal, Shrewsbury, MA (US); Fu-Gang Zhu, Dorchester, MA (US); Ekambar R. Kandimalla, Southboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 1058 days.

(21) Appl. No.: 10/852,598

(22) Filed: May 24, 2004

(65) Prior Publication Data

US 2005/0130918 A1 Jun. 16, 2005

Related U.S. Application Data

(60) Provisional application No. 60/528,277, filed on Dec. 8, 2003.

(51) Int. Cl.
*A61K 45/00* (2006.01)
(52) U.S. Cl. .................................... 424/278.1
(58) Field of Classification Search ........................ None
See application file for complete search history.

(56) References Cited

U.S. PATENT DOCUMENTS

| | | | |
|---|---|---|---|
| 5,149,798 | A | 9/1992 | Agrawal et al. |
| 5,366,878 | A | 11/1994 | Pederson et al. |
| 5,635,377 | A | 6/1997 | Pederson et al. |
| 5,652,355 | A | 7/1997 | Metelev et al. |
| 5,912,332 | A | 6/1999 | Agrawal et al. |
| 6,143,881 | A | 11/2000 | Metelev et al. |
| 6,346,614 | B1 | 2/2002 | Metelev et al. |
| 6,683,167 | B2 | 1/2004 | Metelev et al. |
| 2002/0132995 | A1 | 9/2002 | Agrawal et al. |
| 2003/0199466 | A1* | 10/2003 | Fearon et al. .................. 514/44 |
| 2003/0212026 | A1* | 11/2003 | Krieg et al. .................... 514/44 |
| 2005/0026861 | A1* | 2/2005 | Kandimalla et al. ........... 514/44 |

FOREIGN PATENT DOCUMENTS

| | | |
|---|---|---|
| EP | 1393745 | 3/2004 |
| WO | WO98/49288 | 11/1998 |
| WO | WO01/12804 | 2/2001 |
| WO | WO91/12804 | 2/2001 |
| WO | US01/13682 | 4/2001 |
| WO | WO01/55370 | 8/2001 |
| WO | US01/30137 | 9/2001 |
| WO | WO03/057822 | 7/2003 |
| WO | WO2004/064782 | 8/2004 |

OTHER PUBLICATIONS

U.S. Appl. No. 60/477,608, filed Jun. 11, 2003.*
Agrawal et al., "Protocols for Oligonucleotides and Analogs", *Meth. in Mol. Biol.*, 20:164-189.
Oligonucleotides and Analogues, A Practical Approach, 87-108 (F. Eckstein, ed., 1991).
Agrawal et al., "Modified Oligonucleotides as Therapeutic and Diagnostic Agents", Curr. Op. In Biotech., 6:12-19 (1995).
Crooke et al., *Antisense Research and Applications*, eds., CRC Press, Boca Raton, (1993).
Khorana et al., "Total Synthesis of the Structural Gene for an Alanine Transfer Ribonucleic Acid from Yeast", *J. Mol. Biol.*, 72:209-217 (1972).
Beaucage et al., "Deoxynucleoside Phosphoramidites—A New Class of Key Intermediates for Deoxypolynucleotide Synthesis", *Tetrahedron Lett.*, 22(20):1859-1862. (1981).
Agrawal et al., "Oligodeoxynucleoside Methylphosphonates: Synthesis and Enzymic Degradation", *Tetrahedron Lett.*, 28(31):3539-3542 (1987).
Connolly et al., "Synthesis and Characterization of an Octanucleotide Conyaining the *EcoRI* Recognition Sequence with a Phosphorothioate Group at the Cleavage Site", *Biochem.*, 23:3443-3453 (1984).
Jager et al., "Oligonucleotide *N*-Alkylphosphoramidates: Synthesis and Bindings to Polynucleotides", *Biochem.*, 27:7237-7246 (1988).
Agrawal et al., Oligodeoxynucleotides Phosphoramidites and Phosphorothiotes as Inhibitors of Human Immunodeficiency Virus, *Proc. Natl. Acad. Sci. (USA)*, 85:7079-7083 (1988).
Kuramoto et al., "Oligonucleotide Sequences Required for Natural Killer Cell Actovation", *Jpn. J. Cancer Res.*, 83:1128-1131 (1992).
Reese et al., "The Chemical Synthesis of Oligo- and Poly-Nucleotides by the Phosphotriester Approach", *Tetrahedron Lett.* 34:3143-3179, (1978).
Krieg et al., "CpG Motifs in Bacterial DNA Trigger Direct B-Cell Activation", *Nature*, 374: 546-549. (1995).
Liang et al., "Activation of Human B Cells by Phosphorothioate Oligodeoxynucleotides", *J. Clin. Invest*., 98: 1119-1129, (1996).
Zhao et al., "Effect of Different Chemically Modified Oligodeoxynucleotides on Immune Stimulation", *Biochem. Pharmacol*. 51:173-182, (1996).
Zhao et al., "Modulation of Oligonucleotide-Induced Immune Stimulation by Cyclodextrin Analogs", *Biochem. Pharmacol*. 52:1537-1544, (1996).
Zhao et al., "Pattern and Kinetics of Cytokine Production Following Administration of Phosphorothiote Oligonucleotides in Mice", *Antisense Nucleic Acid Drug Dev*. 7:495-502, (1997).

(Continued)

*Primary Examiner*—Emily M. Le
(74) *Attorney, Agent, or Firm*—Wood, Phillips, Katz, Clark & Mortimer; Joseph C. Zucchero

(57) ABSTRACT

The invention relates to the therapeutic use of oligonucleotides as immunostimulatory agents in immunotherapy applications. More particularly, the invention provides immunomers for use in methods for generating an immune response or for treating a patient in need of immunostimulation. The immunomers of the invention comprise at least two oligonucleotides linked at their 3' ends, internucleoside linkages or functionalized nucleobase or sugar to a non-nucleotidic linker, at least one of the oligonucleotides being an immunostimulatory oligonucleotide and having an accessible 5' end.

14 Claims, 31 Drawing Sheets

OTHER PUBLICATIONS

McCluskie et al., "Cutting Edge:CpG DNA is a Potent Enhancer of Systemic and Mucosal Immune Responses Against Hepatitis B Surface Antigen with Intranasal Administration to Mice", *J. Immunol.* 161:4463-4466, (1998.

Moldovan et al., "CpG DNA, A Novel Immune Enhancer for a Systemic and Mucosal Immunization with Influenza Virus", *Vaccine* 16(11/12):1216-124, (1998).

Zhao et al., "Site of Chemical Modifications in CpG Containing Phosphorothioate Oligodeoxynucleotide Modulates its Immunostimulatory Activity", *Bioorg. Med. Chem. Lett.* 9:3453-3458, (1999).

Zhao et al., "Immunostimulatory Activity of CpG Containing Phosphorothioate Oligodeoxynucleotide is Modulated by Modification of a Single Deoxynucleoside", *Bioorg. Med. Chem. Lett.* 10:1051-1054, (2000).

Yu et al., "Accessible 5'-End of CpG-Containing Phosphorothioate Oligodeoxynucleotides is Essential for Immunostimulatory Activity", *Bioorg. Med. Chem. Lett.* 10:2585-2588,(2000).

Kandimalla et al., "Effect of Chemical Modifications of Cytosine and Guanine in a CpG-Motif of Oligonucleotides: Structure-Immunostimulatory Activity Relationships", *Bioorg. Med. Chem.* 9:807-813,(2001).

Yu et al., "Modulation of Immunostimulatory Activity of CpG Oligonucleotides by Site-Specific Deletion of Nucleobases", *Bioorg. Med. Chem. Lett.* 11:2263-2267, (2001).

\* cited by examiner

Linkers for linear synthesis

Parallel Synthesis of Immunomers

Immunomer

Figure 22

IMO1  5'-CTGTCCRTTCTC-X-CTCTTRCTGTC-5'
IMO2  5'-TCRTCRTTG-X-GTTRCTRCT-5'
IMO3  5'-TCTGTCRTTCT-X-TCTTRCTGTCT-5'
IMO4  5'-TCTGTR'GTTCT-X-TCTTGR'TGTCT-5'
IMO5  5'-TCRTCRTTG-X-GTTRCTRCT-5'
IMO6  5'-YYCTGACGTTCTCTGT-X-TGTCTCTTGCAGTCYY-5'

R – 2'-deoxy-7-deazaguanosine   X – Glycerol linker

R – Arabinoguanosine

R' – 1-(2'-deoxy-β-D-ribofuranosyl)-2-oxo-7-deaza-8-methyl-purine

Y = C3-linker; PO=Phosphodiester backbone

US 7,713,535 B2

MODULATION OF IMMUNOSTIMULATORY PROPERTIES BY SMALL OLIGONUCLEOTIDE-BASED COMPOUNDS

RELATED APPLICATION

This application claims the benefit of U.S. Provisional Application No. 60/528,277, filed Dec. 8, 2003, which is incorporated by reference in its entirety.

BACKGROUND OF THE INVENTION

1. Field of the Invention

The invention relates to immunology and immunotherapy applications using oligonucleotides as immunostimulatory agents.

2. Summary of the Related Art

Oligonucleotides have become indispensable tools in modern molecular biology, being used in a wide variety of techniques, ranging from diagnostic probing methods to PCR to antisense inhibition of gene expression and immunotherapy applications. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See, e.g., *Methods in Molecular Biology*, Vol. 20: *Protocols for Oligonucleotides and Analogs* pp. 165-189 (S. Agrawal, ed., Humana Press, 1993); *Oligonucleotides and Analogues, A Practical Approach*, pp. 87-108 (F. Eckstein, ed., 1991); and Uhlmann and Peyman, supra; Agrawal and Iyer, *Curr. Op. in Biotech.* 6:12 (1995); and *Antisense Research and Applications* (Crooke and Lebleu, eds., CRC Press, Boca Raton, 1993). Early synthetic approaches included phosphodiester and phosphotriester chemistries. For example, Khorana et al., *J. Molec. Biol.* 72:209 (1972) discloses phosphodiester chemistry for oligonucleotide synthesis. Reese, *Tetrahedron Lett.* 34:3143-3179 (1978), discloses phosphotriester chemistry for synthesis of oligonucleotides and polynucleotides. These early approaches have largely given way to the more efficient phosphoramidite and H-phosphonate approaches to synthesis. For example, Beaucage and Caruthers, *Tetrahedron Lett.* 22:1859-1862 (1981), discloses the use of deoxyribonucleoside phosphoramidites in polynucleotide synthesis. Agrawal and Zamecnik, U.S. Pat. No. 5,149,798 (1992), discloses optimized synthesis of oligonucleotides by the H-phosphonate approach. Both of these modern approaches have been used to synthesize oligonucleotides having a variety of modified internucleotide linkages. Agrawal and Goodchild, *Tetrahedron Lett.* 28:3539-3542 (1987), teaches synthesis of oligonucleotide methylphosphonates using phosphoramidite chemistry. Connolly et al., *Biochem.* 23:3443 (1984), discloses synthesis of oligonucleotide phosphorothioates using phosphoramidite chemistry. Jager et al., *Biochem.* 27:7237 (1988), discloses synthesis of oligonucleotide phosphoramidates using phosphoramidite chemistry. Agrawal et al., *Proc. Natl. Acad. Sci.* (USA) 85:7079-7083 (1988), discloses synthesis of oligonucleotide phosphoramidates and phosphorothioates using H-phosphonate chemistry.

More recently, several researchers have demonstrated the validity of the use of oligonucleotides as immunostimulatory agents in immunotherapy applications. The observation that phosphodiester and phosphorothioate oligonucleotides can induce immune stimulation has created interest in developing this side effect as a therapeutic tool. These efforts have focused on phosphorothioate oligonucleotides containing the dinucleotide natural CpG. Kuramoto et al., *Jpn. J Cancer Res.* 83:1128-1131 (1992) teaches that phosphodiester oligonucleotides containing a palindrome that includes a CpG dinucleotide can induce interferon-alpha and gamma synthesis and enhance natural killer activity. Krieg et al., *Nature* 371:546-549 (1995) discloses that phosphorothioate CpG-containing oligonucleotides are immunostimulatory. Liang et al., *J. Clin. Invest.* 98:1119-1129 (1996) discloses that such oligonucleotides activate human B cells. Moldoveanu et al., *Vaccine* 16:1216-124 (1998) teaches that CpG-containing phosphorothioate oligonucleotides enhance immune response against influenza virus. McCluskie and Davis, *J. Immunol.* 161:4463-4466 (1998) teaches that CpG-containing oligonucleotides act as potent adjuvants, enhancing immune response against hepatitis B surface antigen.

Other modifications of CpG-containing phosphorothioate oligonucleotides can also affect their ability to act as modulators of immune response. See, e.g., Zhao et al., *Biochem. Pharmacol.* (1996) 51:173-182; Zhao et al., *Biochem Pharmacol.* (1996) 52:1537-1544; Zhao et al., *Antisense Nucleic Acid Drug Dev.* (1997) 7:495-502; Zhao et al., *Bioorg. Med Chem. Lett.* (1999) 9:3453-3458; Zhao et al., *Bioorg. Med Chem. Lett.* (2000) 10:1051-1054; Yu et al., *Bioorg. Med. Chem. Lett.* (2000) 10:2585-2588; Yu et al., *Bioorg. Med. Chem. Lett.* (2001) 11:2263-2267; and Kandimalla et al., *Bioorg. Med. Chem.* (2001) 9:807-813.

One response that CpG-containing oligonucleotides may modulate is asthma. An allergic asthma response is characterized by activation of T-helper type 2 (Th2) lymphocytes. The responses induced by Th2 lymphocytes play a major role in the pathogenesis and propagation of allergic inflammation in asthma. The Th2 cytokine IL-5 increases the generation and survival of eosinophils, leading to increased airway eosinophilia. Other Th2 cytokines (IL-4, IL-9, and IL-13) also play critical roles in allergic inflammation by inducing production of allergen-specific IgE, mast-cell proliferation, endothelial-cell adhesion-molecule expression, and airway hyper-responsiveness. Corticosteroids are currently the only widely used treatment for allergic asthma. Steroid treatment is effective only in minimizing the manifestations of inflammation, however, and does not cure the disease. Continuous therapy is required to prevent the progression of allergic asthma.

These reports make clear that there remains a need to be able to enhance and modify the immune response caused by immunostimulatory oligonucleotides.

BRIEF SUMMARY OF THE INVENTION

The invention provides methods for enhancing and modifying the immune response caused by oligonucleotide compounds. The methods according to the invention enable increasing the immunostimulatory effect of immunostimulatory oligonucleotides for immunotherapy applications. The present inventors have surprisingly discovered that modification of an immunostimulatory oligonucleotide to optimally present its 5' end dramatically enhances its immunostimulatory capability. Such an oligonucleotide is referred to herein as an "immunomer."

In a first aspect, therefore, the invention provides immunomers comprising at least two oligonucleotides linked at their 3' ends, an internucleotide linkage, or a functionalized nucleobase or sugar via a non-nucleotidic linker, at least one of the oligonucleotides being an immunostimulatory oligonucleotide and having an accessible 5' end.

In one embodiment, the immunostimulatory oligonucleotide immunomer comprises the sequence of SEQ ID NO 76.

In a second aspect, the invention provides an immunomodulatory composition comprising the immunomodulatory oligonucleotide immunomer comprising the sequence of SEQ ID NO 76; and further comprising a co-stimulatory molecule selected from the group consisting of cytokines, chemokines, protein ligands, a trans-activating factors, peptides, and peptides comprising a modified amino acid. In this aspect of the invention, the co-stimulatory molecule is, optionally, conjugated to the immunomodulatory oligonucleotide immunomer, and the immunomodulatory composition further, optionally, comprises an adjuvant and/or a pharmaceutically acceptable carrier.

In a third aspect, the invention provides an immunomodulatory composition comprising the immunomodulatory oligonucleotide immunomer comprising the sequence of SEQ ID NO 76; and further comprising an antigen, wherein the antigen is selected from the group consisting of peptides, glycoproteins, lipoproteins, polysaccharides, and lipids, or wherein the antigen is an allergen. In this aspect of the invention, the immunomodulatory composition further, optionally, comprises an adjuvant and/or a pharmaceutically acceptable carrier.

In another embodiment, the immunostimulatory oligonucleotide immunomer comprises the sequence of SEQ ID NO 72.

In a fourth aspect, the invention provides an immunomodulatory composition comprising the immunomodulatory oligonucleotide immunomer comprising the sequence of SEQ ID NO 72; and further comprising a co-stimulatory molecule selected from the group consisting of cytokines, chemokines, protein ligands, a trans-activating factors, peptides, and peptides comprising a modified amino acid. In this aspect of the invention, the co-stimulatory molecule is, optionally, conjugated to the immunomodulatory oligonucleotide immunomer, and the immunomodulatory composition further, optionally, comprises an adjuvant and/or a pharmaceutically acceptable carrier.

In a fifth aspect, the invention provides an immunomodulatory composition comprising the immunomodulatory oligonucleotide immunomer comprising the sequence of SEQ ID NO 72; and further comprising an antigen, wherein the antigen is selected from the group consisting of peptides, glycoproteins, lipoproteins, polysaccharides, and lipids, or wherein the antigen is an allergen. In this aspect of the invention, the immunomodulatory composition further, optionally, comprises an adjuvant and/or a pharmaceutically acceptable carrier.

In another embodiment, the invention provides a method for therapeutically treating a patient having airway inflammation, inflammatory disorders, allergy, or asthma, such method comprising administering to the patient an immunomer.

In a sixth aspect, the invention provides a method for therapeutically treating a patient wherein the immunomer comprises at least two oligonucleotides linked by a non-nucleotidic linker and having more than one 5' end, wherein at least one of the oligonucleotides is an immunostimulatory oligonucleotide having an accessible 5' end and comprises an immunostimulatory dinucleotide. The immunostimulatory dinucleotide is selected from the group consisting of CpG, C*pG, CpG*, and C*pG*, wherein C is cytidine or 2'-deoxycytidine, C* is 2'-deoxythymidine, arabinocytidine, 1-(2'-deoxy-β-D-ribofuranosyl)-2-oxo-7-deaza-8-methyl-purine, 2'-deoxy-2'-substitutedarabinocytidine, 2'-O-substitutedarabinocytidine, 2'-deoxy-5-hydroxycytidine, 2'-deoxy-N-4-alkyl-cytidine, 2'-deoxy-4-thiouridine or other non-natural pyrimidine nucleoside, G is guanosine or 2'-deoxyguanosine, G* is 2' deoxy-7-deazaguanosine, 2'-deoxy-6-thioguanosine, arabinoguanosine, 2'-deoxyinosine, 2'-deoxy-2'substituted-arabinoguanosine, 2'-O-substituted-arabinoguanosine.

In a seventh aspect, the invention provides a method for therapeutically treating a patient, wherein the immunomer comprises the sequence of SEQ ID NO 76, or the sequence of SEQ ID NO 72, or the sequence of SEQ ID NO 18, or the sequence of SEQ ID NO 73.

In an eighth aspect, the invention provides a method for therapeutically treating a patient further comprising administering an antigen associated with said disease or disorder, wherein the immunomer or the antigen, or both, are linked to an immunogenic protein or non-immunogenic protein, and/or further comprising administering an adjuvant.

In another embodiment, the invention provides a method for modulating an immune response in a patient having airway inflammation, inflammatory disorders, allergy, or asthma comprising administering to the patient an immunomer, wherein the immune response is a Th1 and/or a Th2 immune response.

In a ninth aspect, the invention provides a method for modulating an immune response in a patient, wherein the immunomer comprises at least two oligonucleotides linked by a non-nucleotidic linker and having more than one 5' end, wherein at least one of the oligonucleotides is an immunostimulatory oligonucleotide having an accessible 5' end and comprises an immunostimulatory dinucleotide. The immunostimulatory dinucleotide is selected from the group consisting of CpG, C*pG, CpG*, and C*pG*, wherein C is cytidine or 2'-deoxycytidine, C* is 2'-deoxythymidine, arabinocytidine, 1-(2'-deoxy-β-D-ribofuranosyl)-2-oxo-7-deaza-8-methyl-purine, 2'-deoxy-2'-substitutedarabinocytidine, 2'-O-substitutedarabinocytidine, 2'-deoxy-5-hydroxycytidine, 2'-deoxy-N-4-alkyl-cytidine, 2'-deoxy-4-thiouridine or other non-natural pyrimidine nucleoside, G is guanosine or 2'-deoxyguanosine, G* is 2' deoxy-7-deazaguanosine, 2'-deoxy-6-thioguanosine, arabinoguanosine, 2'-deoxyinosine, 2'-deoxy-2'substituted-arabinoguanosine, 2'-O-substituted-arabinoguanosine.

In a tenth aspect the invention provides a method for modulating an immune response in a patient wherein the immunomer comprises the sequence of SEQ ID NO 76, or the sequence of SEQ ID NO 72, or the sequence of SEQ ID NO 18, or the sequence of SEQ ID NO 73.

In an eleventh aspect, the invention provides a method for therapeutically treating a patient further comprising administering an antigen associated with said disease or disorder, wherein the immunomer or the antigen, or both, are linked to an immunogenic protein or non-immunogenic protein, and/or further comprising administering an adjuvant.

BRIEF DESCRIPTION OF THE DRAWINGS

FIG. 22 shows sequences and chemical modifications of immunomers (IMOs) (SEQ ID NOS 76, 72, 18, 77, 73, and 8, respectively in order of appearance).

FIG. 26 shows serum antigen-specific and total antibodies. IMOs 1 and 2 produced dose-dependent reduction of OVA-specific IgE and increase of OVA-specific IgG2a.

DETAILED DESCRIPTION OF THE PREFERRED EMBODIMENTS

Figure 1:
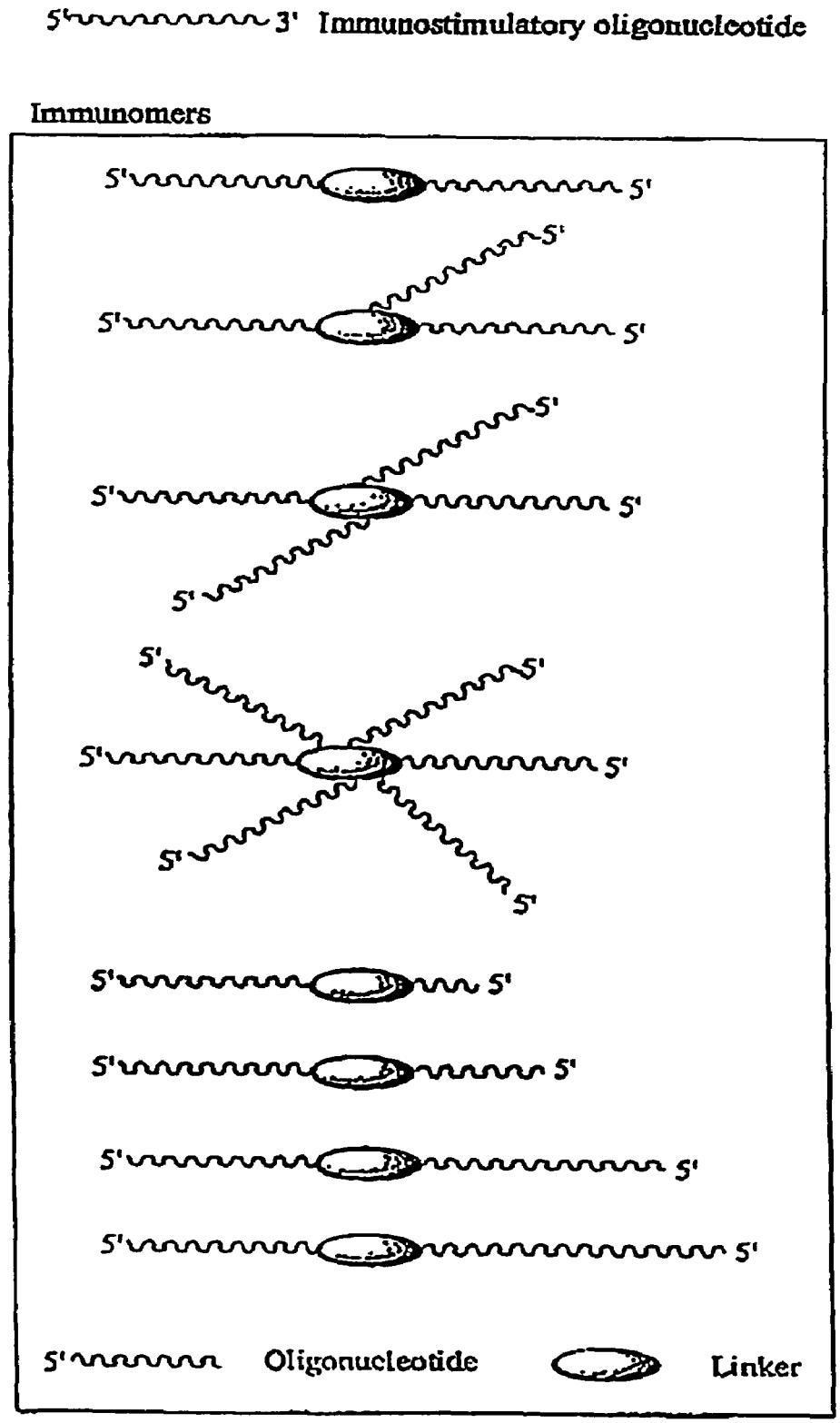
FIG. 1 is a schematic representation of representative immunomers of the invention.

The invention relates to the therapeutic use of oligonucleotides as immunostimulatory agents for immunotherapy applications. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for enhancing and modifying the immune response caused by immunostimulatory compounds used for immunotherapy applications such as, but not limited to, treatment of cancer, autoimmune disorders, asthma, respiratory allergies, food allergies, and bacteria, parasitic, and viral infections in adult and pediatric human and veterinary applications. Allergic asthma is a particularly preferred condition for treatment by the present methods and compounds. Thus, the invention further provides compounds having optimal levels of immunostimulatory effect for immunotherapy and methods for making and using such compounds. In addition, immunomers of the invention are useful as adjuvants in combination with DNA vaccines, antibodies, allergens, chemotherapeutic agents, and antisense oligonucleotides.

The present inventors have surprisingly discovered that modification of an immunostimulatory oligonucleotide to optimally present its 5' ends dramatically affects its immunostimulatory capabilities. Such an oligonucleotide is referred to herein as an "immunomer."

In a first aspect, the invention provides immunomers comprising at least two oligonucleotides linked at their 3' ends, or an internucleoside linkage or a functional ized nucleobase or sugar to a non-nucleotidic linker, at least one of the oligonucleotides being an immunostimulatory oligonucleotide and having an accessible 5' end. As used herein, the term "accessible 5' end" means that the 5' end of the oligonucleotide is sufficiently available such that the factors that recognize and bind to immunomers and stimulate the immune system have access to it. In oligonucleotides having an accessible 5' end, the 5' OH position of the terminal sugar is not covalently linked to more than two nucleoside residues. Optionally, the 5' OH can be linked to a phosphate, phosphorothioate, or phosphorodithioate moiety, an aromatic or aliphatic linker, cholesterol, or another entity which does not interfere with accessibility.

For purposes of the invention, the term "immunomer" refers to any compound comprising at least two oligonucleotides linked at their 3' ends or internucleoside linkages, or functionalized nucleobase or sugar directly or via a non-nucleotidic linker, at least one of the oligonucleotides (in the context of the immunomer) being an immunostimulatory oligonucleotide and having an accessible 5' end, wherein the compound induces an immune response when administered to a vertebrate. In some embodiments, the vertebrate is a mammal, including a human.

In some embodiments, the immunomer comprises two or more immunostimulatory oligonucleotides, (in the context of the immunomer) which may be the same or different. Preferably, each such immunostimulatory oligonucleotide has at least one accessible 5' end.

In certain embodiments, in addition to the immunostimulatory oligonucleotide(s), the immunomer also comprises at least one oligonucleotide that is complementary to a gene. As used herein, the term "complementary to" means that the oligonucleotide hybridizes under physiological conditions to a region of the gene. In some embodiments, the oligonucleotide downregulates expression of a gene. Such downregulatory oligonucleotides preferably are selected from the group consisting of antisense oligonucleotides, ribozyme oligonucleotides, small inhibitory RNAs and decoy oligonucleotides. As used herein, the term "downregulate a gene" means to inhibit the transcription of a gene or translation of a gene product. Thus, the immunomers according to these embodiments of the invention can be used to target one or more specific disease targets, while also stimulating the immune system.

In certain embodiments, the immunomer includes a ribozyme or a decoy oligonucleotide. As used herein, the term "ribozyme" refers to an oligonucleotide that possesses catalytic activity. Preferably, the ribozyme binds to a specific nucleic acid target and cleaves the target. As used herein, the term "decoy oligonucleotide" refers to an oligonucleotide that binds to a transcription factor in a sequence-specific manner and arrests transcription activity. Preferably, the ribozyme or decoy oligonucleotide exhibits secondary structure, including, without limitation, stem-loop or hairpin structures. In certain embodiments, at least one oligonucleotide comprising poly(I)-poly(dC). In certain embodiments, at least one set of Nn includes a string of 3 to 10 dGs and/or Gs or 2'-substituted ribo or arabino Gs.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substitutedarabinose, 2'-O-substitutedarabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_P)$- or $(S_P)$-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

In some embodiments, the oligonucleotides each have from about 3 to about 35 nucleoside residues, preferably from about 4 to about 30 nucleoside residues, more preferably from about 4 to about 20 nucleoside residues. In some embodiments, the oligonucleotides have from about 5 to about 18, or from about 5 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above. In some embodiments, one or more of the oligonucleotides have 11 nucleotides.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

As used herein, the term "secondary structure" refers to intramolecular and intermolecular hydrogen bonding.

Intramolecular hydrogen bonding results in the formation of a stem-loop structure. Intermolecular hydrogen bonding results in the formation of a duplexed nucleic acid molecule.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-fluoroarabinoside.

For purposes of the invention, the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of such 2'-O-substituted ribonucleosides include, without limitation 2'-O-methylribonucleosides and 2'-O-methoxyethylribonucleosides.

The term "2'-substituted ribonucleoside" also includes ribonucleosides in which the 2'-hydroxyl group is replaced with a lower alkyl group containing 1-6 saturated or unsaturated carbon atoms, or with an amino or halo group. Examples of such 2'-substituted ribonucleosides include, without limitation, 2'-amino, 2'-fluoro, 2'-allyl, and 2'-propargyl ribonucleosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,683,167, 6,346,614 and 6,143,881).

For purposes of the invention, the term "immunostimulatory oligonucleotide" refers to an oligonucleotide as described above that induces an immune response when administered to a vertebrate, such as a fish, fowl, or mammal. As used herein, the term "mammal" includes, without limitation rats, mice, cats, dogs, horses, cattle, cows, pigs, rabbits, non-human primates, and humans. Useful immunostimulatory oligonucleotides can be found described in Agrawal et al., WO 98/49288, published Nov. 5, 1998; WO 01/12804, published Feb. 22, 2001; WO 01/55370, published Aug. 2, 2001; PCT/US01/13682, filed Apr. 30, 2001; and PCT/US01/30137, filed Sep. 26, 2001. Preferably, the immunostimulatory oligonucleotide comprises at least one phosphodiester, phosphorothioate, or phosphordithioate internucleoside linkage.

In some embodiments, the immunostimulatory oligonucleotide comprises an immunostimulatory dinucleotide of formula 5'-Pyr-Pur-3', wherein Pyr is a natural or synthetic pyrimidine nucleoside and Pur is a natural or synthetic purine nucleoside. As used herein, the term "pyrimidine nucleoside" refers to a nucleoside wherein the base component of the nucleoside is a pyrimidine base. Similarly, the term "purine nucleoside" refers to a nucleoside wherein the base component of the nucleoside is a purine base. For purposes of the invention, a "synthetic" pyrimidine or purine nucleoside includes a non-naturally occurring pyrimidine or purine base, a non-naturally occurring sugar moiety, or a combination thereof.

Preferred pyrimidine nucleosides according to the invention have the structure (I):

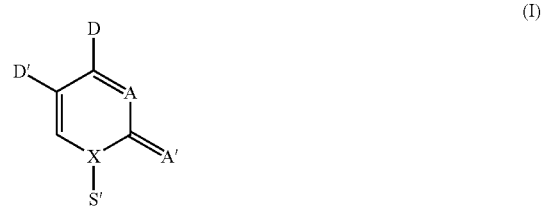

(i) wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C═O, C═S, and the ring nitrogen atoms of an aromatic heterocycle, e.g., N3 of cytosine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. However, in some embodiments 5-bromocytosine is specifically excluded.

In some embodiments, the sugar moiety S' in (I) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are examples of a preferred sugar moieties.

Preferred purine nucleoside analogs according to the invention have the structure (II):

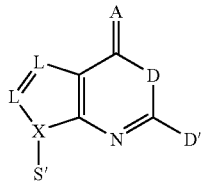

(ii) wherein:

D is a hydrogen bond donor;

D' is selected from the group consisting of hydrogen, hydrogen bond donor, and hydrophilic group;

A is a hydrogen bond acceptor or a hydrophilic group;

X is carbon or nitrogen;

each L is independently selected from the group consisting of C, O, N and S; and S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, —NO$_2$ and the ring nitrogen atoms of an aromatic heterocycle, e.g., N1 of guanine.

In some embodiments, the base moiety in (II) is a non-naturally occurring purine base. Examples of preferred non-naturally occurring purine bases include, without limitation, 6-thioguanine and 7-deazaguanine. In some embodiments, the sugar moiety S' in (II) is a naturally occurring sugar moiety, as described above for structure (I).

In preferred embodiments, the immunostimulatory dinucleotide is selected from the group consisting of CpG, C*pG, CpG*, and C*pG*, wherein C is cytidine or 2'-deoxycytidine, C* is 2'-deoxythymidine, 1-(2'-deoxy-β-D-ribofuranosyl)-2-oxo-7-deaza-8-methyl-purine, arabinocytidine, 2'-deoxythymidine, 2'-deoxy-2'-substitutedarabinocytidine, 2'-O-substitutedarabinocytidine, 2'-deoxy-5-hydroxycytidine, 2'-deoxy-N-4-alkyl-cytidine, 2'-deoxy-4-thiouridine or other non-natural pyrimidine nucleoside or rarely occurring pyrimidine nucleoside, G is guanosine or 2'-deoxyguanosine, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside or rarely occurring purine nucleoside, and p is an internucleoside linkage selected from the group consisting of phosphodiester, phosphorothioate, and phosphorodithioate. In certain preferred embodiments, the immunostimulatory dinucleotide is not CpG.

The immunostimulatory oligonucleotides may include immunostimulatory moieties on one or both sides of the immunostimulatory dinucleotide. Thus, in some embodiments, the immunostimulatory oligonucleotide comprises in immunostimulatory domain of structure (III):

5'-Nn-N1-Y-Z-N1-Nn-3'     (III)

wherein:

Y is cytidine, 2'deoxythymidine, 2' deoxycytidine arabinocytidine, 2'-deoxy-2'-substitutedarabinocytidine, 2'-deoxythymidine, 2'-O-substitutedarabinocytidine, 2'-deoxy-5-hydroxycytidine, 2'-deoxy-N-4-alkyl-cytidine, 2'-deoxy-4-thiouridine or other non-natural pyrimidine nucleoside;

Z is guanosine or 2'-deoxyguanosine, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'deoxyinosine, or other non-natural purine nucleoside;

N1, at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly(ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;

Nn, at each occurrence, is preferably a naturally occurring nucleoside or an immunostimulatory moiety selected from the group consisting of abasic nucleosides, arabinonucleosides, 2'-deoxyuridine, α-deoxyribonucleosides, 2'-O-substituted ribonucleosides, and nucleosides linked by a modified internucleoside linkage to the adjacent nucleoside on the 3' side, the modified internucleotide linkage preferably being selected from the group consisting of amino linker, 2'-5' internucleoside linkage, and methylphosphonate internucleoside linkage;

provided that at least one N1 or Nn is an immunostimulatory moiety;

wherein n is a number from 0 to 30; and wherein the 3'end, an internucleoside linker, or a derivatized nucleobase or sugar is linked directly or via a non-nucleotidic linker to another oligonucleotide, which may or may not be immunostimulatory.

In some preferred embodiments, YZ is arabinocytidine or 2'-deoxy-2'-substituted arabinocytidine and arabinoguanosine or 2'deoxy-2'-substituted arabinoguanosine. Preferred immunostimulatory moieties include modifications in the phosphate backbones, including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., ($R_P$)- or ($S_P$)-phosphorothioate, alkylphosphonate, or phosphotriester linkages).

Preferred immunostimulatory moieties according to the invention further include nucleosides having sugar modifications, including, without limitation, 2'-substituted pentose sugars including, without limitation, 2'-O-methylribose, 2'-O-methoxyethylribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethyl-arabinose, and 2'-substituted arabinose sugars; hexose sugars, including, without limitation, 1,5-anhydrohexitol; and alpha-anomers. In embodiments in which the modified sugar is a 3'-deoxyribonucleoside or a 3'-O-substituted ribonucleoside, the immunostimulatory moiety is attached to the adjacent nucleoside by way of a 2'-5' internucleoside linkage.

Preferred immunostimulatory moieties according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some such functionalized alkyl linkers are poly(ethylene glycol) linkers of formula —O—($CH_2$—$CH_2$—O—)$_n$ (n=1-9). Some other functionalized alkyl linkers are peptides or amino acids.

Preferred immunostimulatory moieties according to the invention further include DNA isoforms, including, without limitation, β-L-deoxyribonucleosides and a-deoxyribonucleosides. Preferred immunostimulatory moieties according to the invention incorporate 3' modifications, and further include nucleosides having unnatural internucleoside linkage positions, including, without limitation, 2'-5',2'-2', 3'-3' and 5'-5' linkages.

Preferred immunostimulatory moieties according to the invention further include nucleosides having modified heterocyclic bases, including, without limitation, 5-hydroxycytosine, 5-hydroxymethylcytosine, N4-alkylcytosine, preferably N4-ethylcytosine, 4-thiouracil, 6-thioguanine, 7-deazaguanine, inosine, nitropyrrole, C5-propynylpyrimidine, and diaminopurines, including, without limitation, 2,6-diaminopurine.

By way of specific illustration and not by way of limitation, for example, in the immunostimulatory domain of structure (III), a methylphosphonate internucleoside linkage at position N1 or Nn is an immunostimulatory moiety, a linker having a length of from about 2 angstroms to about 200 angstroms, C2-C18 alkyl linker at position X1 is an immunostimulatory moiety, and a β-L-deoxyribonucleoside at position X1 is an immunostimulatory moiety. See Table 1 below for representative positions and structures of immunostimulatory moieties. It is to be understood that reference to a linker as the immunostimulatory moiety at a specified position means that the nucleoside residue at that position is substituted at its 3'-hydroxyl with the indicated linker, thereby creating a modified internucleoside linkage between that nucleoside residue and the adjacent nucleoside on the 3' side. Similarly, reference to a modified internucleoside linkage as the immunostimulatory moiety at a specified position means that the nucleoside residue at that position is linked to the adjacent nucleoside on the 3' side by way of the recited linkage.

TABLE 1

| Position | TYPICAL IMMUNOSTIMULATORY MOIETIES |
|---|---|
| N1 | Naturally-occurring nucleosides, abasic nucleoside, arabinonucleoside, 2'-deoxyuridine, β-L-deoxyribonucleoside C2-C18 alkyl linker, poly(ethylene glycol) linkage, 2-aminobutyl-1,3-propanediol linker (amino linker), 2'-5' internucleoside linkage, methylphosphonate internucleoside linkage |
| Nn | Naturally-occurring nucleosides, abasic nucleoside, arabinonucleosides, 2'-deoxyuridine, 2'-O-substituted ribonucleoside, 2'-5' internucleoside linkage, methylphosphonate internucleoside linkage, provided that N1 and N2 cannot both be abasic linkages |

Table 2 shows representative positions and structures of immunostimulatory moieties within an immunostimulatory oligonucleotide having an upstream potentiation domain. As used herein, the term "Spacer 9" refers to a poly(ethylene glycol) linker of formula —O—($CH_2CH_2$—O)$_n$—, wherein n is 3. The term "Spacer 18" refers to a poly(ethylene glycol) linker of formula —O—($CH_2CH_2$—O)$_n$—, wherein n is 6. As used herein, the term "C2-C18 alkyl linker refers to a linker of formula —O—($CH_2$)$_q$—O—, where q is an integer from 2 to 18. Accordingly, the terms "C3-linker" and "C3-alkyl linker" refer to a linker of formula —O—($CH_2$)$_3$—O—. For each of Spacer 9, Spacer 18, and C2-C18 alkyl linker, the linker is connected to the adjacent nucleosides by way of phosphodiester, phosphorothioate, or phosphorodithioate linkages.

TABLE 2

| Position | TYPICAL IMMUNOSTIMULATORY MOIETY |
|---|---|
| 5' N2 | Naturally-occurring nucleosides, 2-aminobutyl-1,3-propanediol linker |
| 5' N1 | Naturally-occurring nucleosides, β-L-deoxyribonucleoside, C2-C18 alkyl linker, poly(ethylene glycol), abasic linker, 2-aminobutyl-1,3-propanediol linker |
| 3' N1 | Naturally-occurring nucleosides, 1',2'-dideoxyribose, 2'-O-methyl-ribonucleoside, C2-C18 alkyl linker, Spacer 9, Spacer 18 |
| 3' N2 | Naturally-occurring nucleosides, 1',2'-dideoxyribose, 3'-deoxyribonucleoside, β-L-deoxyribonucleoside, 2'-O-propargylribonucleoside, C2-C18 alkyl linker, Spacer 9, Spacer 18, methylphosphonate internucleoside linkage |
| 3' N 3 | Naturally-occurring nucleosides, 1',2'-dideoxyribose, C2-C18 alkyl linker, Spacer 9, Spacer 18, methylphosphonate internucleoside linkage, 2'-5' internucleoside linkage, d(G)n, polyI-polydC |
| 3'N 2 + 3'N 3 | 1',2'-dideoxyribose, β-L-deoxyribonucleoside, C2-C18 alkyl linker, d(G)n, polyI-polydC |
| 3'N3 + 3' N 4 | 2'-O-methoxyethyl-nucleoside, methylphosphonate internucleoside linkage, d(G)n, polyI-polydC |
| 3'N5 + 3' N 6 | 1',2'-dideoxyribose, C2-C18 alkyl linker, d(G)n, polyI-polydC |
| 5'N1 + 3' N 3 | 1',2'-dideoxyribose, d(G)n, polyI-polydC |

Table 3 shows representative positions and structures of immunostimulatory moieties within an immunostimulatory oligonucleotide having a downstream potentiation domain.

TABLE 3

| Position | TYPICAL IMMUNOSTIMULATORY MOIETY |
|---|---|
| 5' N2 | methylphosphonate internucleoside linkage |
| 5' N1 | methylphosphonate internucleoside linkage |
| 3' N1 | 1',2'-dideoxyribose, methylphosphonate internucleoside linkage, 2'-O-methyl |
| 3' N2 | 1',2'-dideoxyribose, β-L-deoxyribonucleoside, C2-C18 alkyl linker, Spacer 9, Spacer 18, 2-aminobutyl-1,3-propanediol linker, methylphosphonate internucleoside linkage, 2'-O-methyl |
| 3' N3 | 3'-deoxyribonucleoside. 3'-O-substituted ribonucleoside, 2'-O-propargyl-ribonucleoside |
| 3' N2 + 3' N3 | 1',2'-dideoxyribose, β-L-deoxyribonucleoside |

The immunomers according to the invention comprise at least two oligonucleotides linked at their 3' ends or internucleoside linkage or a functionalized nucleobase or sugar via a non-nucleotidic linker. For purposes of the invention, a "non-nucleotidic linker" is any moiety that can be linked to the oligonucleotides by way of covalent or non-covalent linkages. Preferably such linker is from about 2 angstroms to about 200 angstroms in length. Several examples of preferred linkers are set forth below. Non-covalent linkages include, but are not limited to, electrostatic interaction, hydrophobic interactions, π-stacking interactions, and hydrogen bonding. The term "non-nucleotidic linker" is not meant to refer to an internucleoside linkage, as described above, e.g., a phosphodiester, phosphorothioate, or phosphorodithioate functional group, that directly connects the 3'-hydroxyl groups of two nucleosides. For purposes of this invention, such a direct 3'-3' linkage is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

Figure 13:
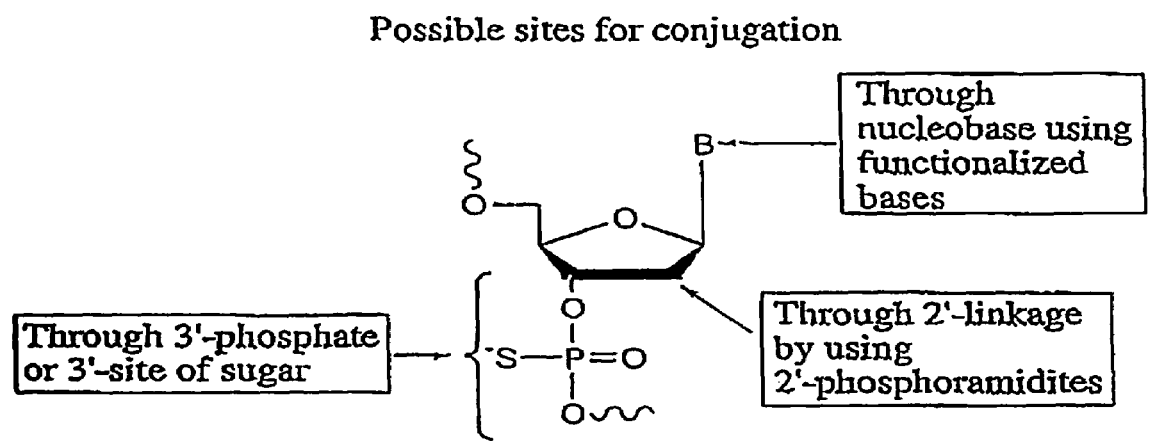
FIG. 13 is a schematic representation of the 3'-terminal nucleoside of an oligonucleotide, showing that a non-nucleotidic linkage can be attached to the nucleoside at the nucleobase, at the 3' position, or at the 2' position.

In yet other embodiments, the non-nucleotidic linker is an organic moiety having functional groups that permit attachment to the oligonucleotide. Such attachment preferably is by any stable covalent linkage. As a non-limiting example, the linker may be attached to any suitable position on the nucleoside, as illustrated in FIG. 13. In some preferred embodiments, the linker is attached to the 3'-hydroxyl. In such embodiments, the linker preferably comprises a hydroxyl functional group, which preferably is attached to the 3'-hydroxyl by means of a phosphodiester, phosphorothioate, phosphorodithioate or non-phosphate-based linkages.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_n$—C(O)NH—$CH_2$—CH(OH)—$CH_2$—NHC(O)—$(CH_2)_n$—OH, wherein m is an integer from 0 to about 10, from 0 to about 6, from 2 to about 6, or from 2 to about 4.

Some non-nucleotidic linkers according to the invention permit attachment of more than two oligonucleotides, as schematically depicted in FIG. 1. For example, the small molecule linker glycerol has three hydroxyl groups to which oligonucleotides may be covalently attached. Some immunomers according to the invention, therefore, comprise more than two oligonucleotides linked at their 3' ends to a non-nucleotidic linker. Some such immunomers comprise at least two immunostimulatory oligonucleotides, each having an accessible 5' end.

Figure 5:
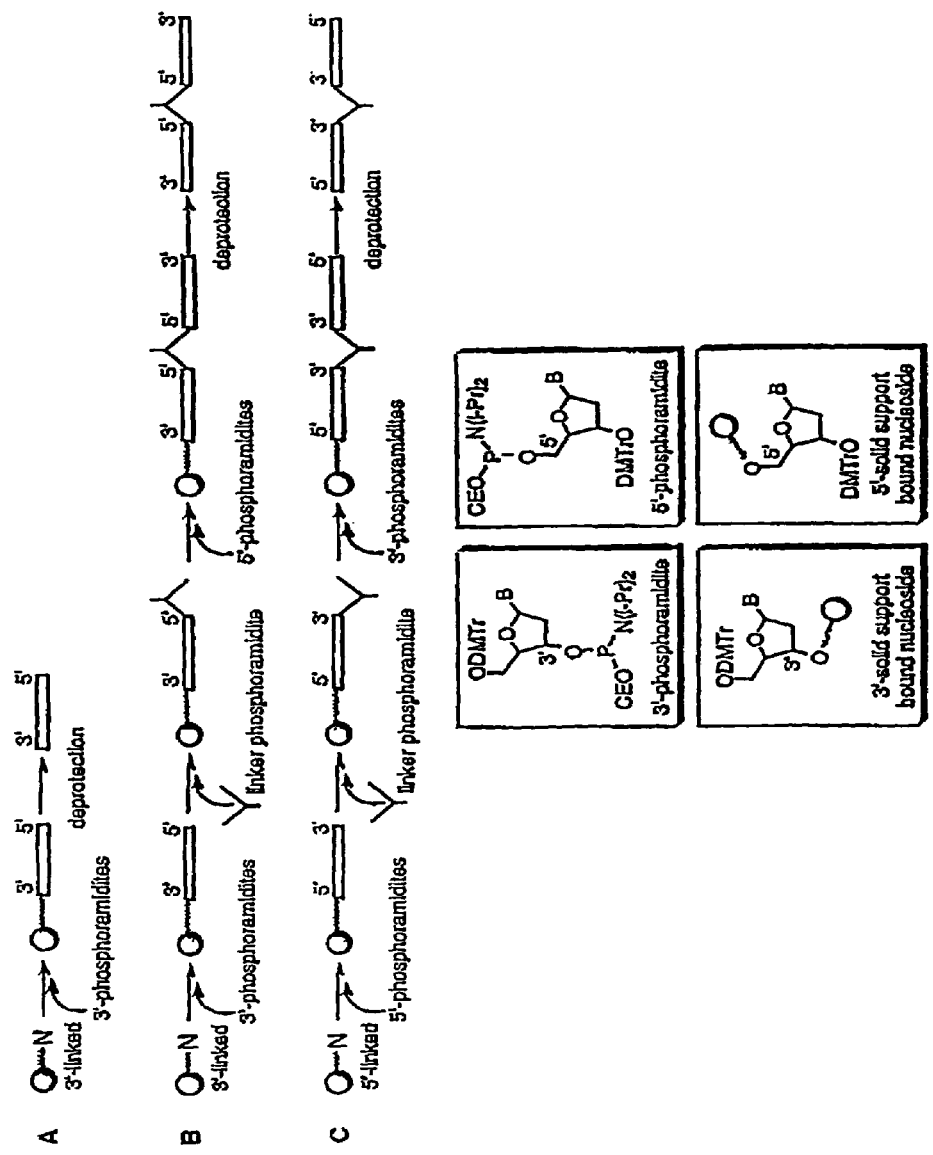
FIG. 5 is a synthetic scheme for the linear synthesis of immunomers of the invention. DMTr=4,4'-dimethoxytrityl; CE=cyanoethyl.
Figure 6:
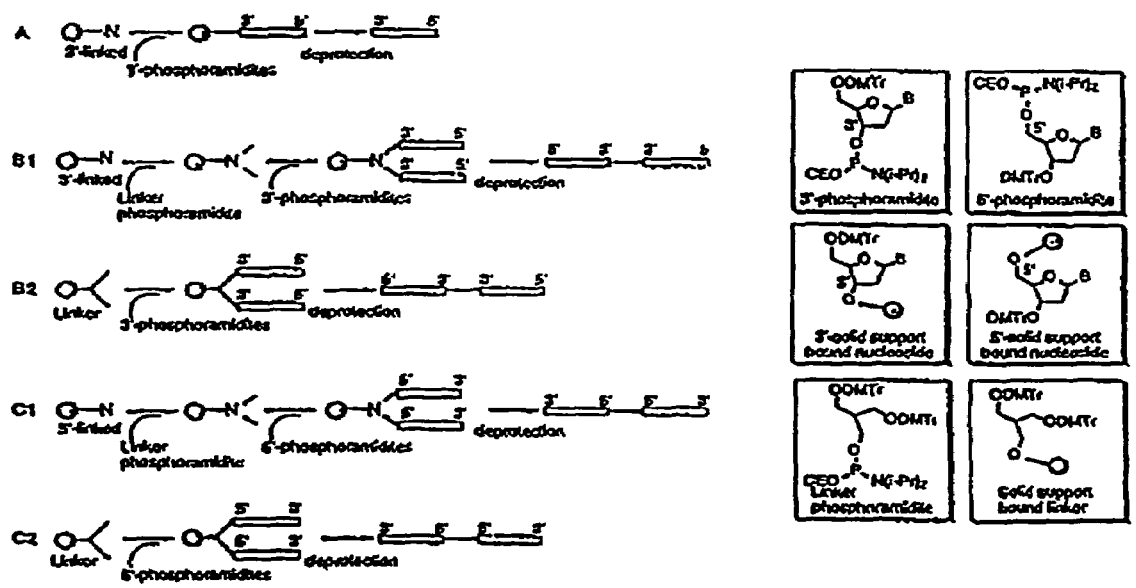
FIG. 6 is a synthetic scheme for the parallel synthesis of immunomers of the invention. DMTr=4,4'-dimethoxytrityl; CE=cyanoethyl.

The immunomers of the invention may conveniently be synthesized using an automated synthesizer and phosphoramidite approach as schematically depicted in FIGS. 5 and 6, and further described in the Examples. In some embodiments, the immunomers are synthesized by a linear synthesis approach (see FIG. 5). As used herein, the term "linear synthesis" refers to a synthesis that starts at one end of the immunomer and progresses linearly to the other end. Linear synthesis permits incorporation of either identical or un-identical (in terms of length, base composition and/or chemical modifications incorporated) monomeric units into the immunomers.

An alternative mode of synthesis is "parallel synthesis", in which synthesis proceeds outward from a central linker moiety (see FIG. 6). A solid support attached linker can be used for parallel synthesis, as is described in U.S. Pat. No. 5,912,332. Alternatively, a universal solid support (such as phosphate attached controlled pore glass support can be used.

Parallel synthesis of immunomers has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immunomer product.

At the end of the synthesis by either linear synthesis or parallel synthesis protocols, the immunomers may conveniently be deprotected with concentrated ammonia solution or as recommended by the phosphoramidite supplier, if a modified nucleoside is incorporated. The product immunomer is preferably purified by reversed phase HPLC, detritylated, desalted and dialyzed.

Tables 4A and 4B show representative immunomers according to the invention. Additional immunomers are found described in the Examples.

TABLE 4

Examples of Immunomer Sequences

| OLIGO/ IMMUNOMER # | SEQ ID NO. | Sequences and Modification (5'-3') |
|---|---|---|
| 1 | 1 | 5'-GAGAACGCTCGACCTT-3' |
| 2 | 1 | 5'-GAGAACGCTCGACCTT-3'-3'-TTCCAGCTCGCAAGAG-5' |
| 3 | 1 | 3'-TTCCAGCTCGCAAGAG-5'-5'-GCGAACGCTCGACCTT-3' |
| 4 | 2 | 5'-CTATCTGACGTTCTCTGT-3' |
| 5 | 78 and 3 | 5'-T-3'—⟨ HNCO—$C_4H_8$—CTATLTGACGTTCTCTGT-3' / HNCO—$C_4H_8$—CTATLTGACGTTCTCTGT-3' ⟩ |

TABLE 4-continued

Examples of Immunomer Sequences

| OLIGO/ IMMUNOMER # | SEQ ID NO. | Sequences and Modification (5'-3') |
|---|---|---|
| 6 | 78 and 3 | 5'-CTATLTGACGTTCTCTGT-3'-C$_4$H$_8$—CONH⌉<br>                                                       ⎯3'-C-5'<br>5'-CTATLTGACGTTCTCTGT-3'-C$_4$H$_8$—CONH⌋ |
| 7 | 2 | 5'-CTATCTGACGTTCTCTGT-3'-C$_4$H$_8$—CONH⌉<br>                                                       ⎯3'-C-5'<br>5'-CTATCTGACGTTCTCTGT-3'-C$_4$H$_8$—CONH⌋ |
| 8 | 2 | 5'-CTATCTGACGTTCTCTGT-3'⌉<br>                                  ⎯3'-C-5'<br>5'-CTATCTGACGTTCTCTGT-3'⌋ |
| 9 | 4 | 5'-CTATCTGAYGTTCTCTGT-3'⌉<br>                                  ⎯3'-C-5'<br>5'-CTATCTGAYGTTCTCTGT-3'⌋ |
| 10 | 5 | 5'-CTATCTGACRTTCTCTGT-3'⌉<br>                                  ⎯3'-C-5'<br>5'-CTATCTGACRTTCTCTGT-3'⌋ |
| 11 | 79 and 6 | 5'-CTALCTGAYGTTCTCTGT-3'⌉<br>                                  ⎯3'-C-5'<br>5'-CTALCTGAYGTTCTCTGT-3'⌋ |
| 12 | 79 and 7 | 5'-CTALCTGACRTTCTCTGT-3'⌉<br>                                  ⎯3'-C-5'<br>5'-CTALCTGACRTTCTCTGT-3'⌋ |
| 13 | 8 | 5'-CTGACGTTCTCTGT-3' |
| 14 | 8 | 5'-CTGACGTTCTCTGT-3'⌉<br>                         ⎯3'-C-5'<br>5'-CTGACGTTCTCTGT-3'⌋ |
| 15 | 6 | 5'-CTGAYGTTCTCTGT-3'⌉<br>                         ⎯3'-C-5'<br>5'-CTGAYGTTCTCTGT-3'⌋ |
| 16 | 7 | 5'-CTGACRTTCTCTGT-3'⌉<br>                         ⎯3'-C-5'<br>5'-CTGACRTTCTCTGT-3'⌋ |
| 17 | 9 | 5'-XXTGACGTTCTCTGT-3' |
| 18 | 10 | 5'-XXXTGACGTTCTCTGT-3'⌉<br>                           ⎯3'-C-5'<br>5'-XXXTGACGTTCTCTGT-3'⌋ |

TABLE 4-continued

Examples of Immunomer Sequences

| OLIGO/<br>IMMUNOMER # | SEQ<br>ID NO. | Sequences and Modification (5'-3') |
|---|---|---|
| 19 | 11 | 5'-XXXTGAYGTTCTCTGT-3'⎤<br>　　　　　　　　　　　　　├─3'-C-5'<br>5'-XXXTGAYGTTCTCTGT-3'⎦ |
| 20 | 12 | 5'-XXXTGACRTTCTCTGT-3'⎤<br>　　　　　　　　　　　　　├─3'-C-5'<br>5'-XXXTGACRTTCTCTGT-3'⎦ |
| 21 | 13 | 5'-TCTGACGTTCT-3' |
| 22 | 14 | 5'-XXXTCTGACGTTCT-3'⎤<br>　　　　　　　　　　　├─3'-C-5'<br>5'-XXXTCTGACGTTCT-3'⎦ |
| 23 | 15 | 5'-XXXTCTGAYGTTCT-3'⎤<br>　　　　　　　　　　　├─3'-C-5'<br>5'-XXXTCTGAYGTTCT-3'⎦ |
| 24 | 16 | 5'-XXXTCTGACRTTCT-3'⎤<br>　　　　　　　　　　　├─3'-C-5'<br>5'-XXXTCTGACRTTCT-3'⎦ |

```
    ┌─NHCOC4H8─
─┤              = Symmetric longer branches;
    └─NHCOC4H8─

─┤   = Symmetric glycerol (short) branches
```

L = C3-alkyl linker; X = 1',2'-dideoxyriboside; Y = $^{5OH}$dC; R = 7-deaza-dG

TABLE 4B

```
SEQ ID
NO.    Sequences and Modification (5'-3')

76    5'-CTGTCRTTCTC-X-CTCTTRCTGTC-5'

72    5'-TCRTCRTTG-X-GTTRCTRCT-5'

18    5'-TCTGTCRTTCT-X-TCTTRCTGTCT-5'

77    5'-TCTGTR'GTTCT-X-TCTTGR'TGTCT-5'

73    5'-TCRTCRTTG-X-GTTRCTRCT-5'

8    5'-YYCTGACGTTCTCTGT-X-TGTCTCTTGCAGTCYY-5'

X = glycerol linker;
R = Arabinoguanosine;
R = 2'-deoxy-7'-deazaguanosine,
R' = 1-(2'-deoxy-b-D-ribofuranosyl)-2-oxo-7-deaza-
8-methyl-purine;
Y = C3-linker
```

In another aspect the invention provides an immunostimulatory nucleic acid comprising at least two oligonucleotides, wherein the immunostimulatory nucleic acid has a secondary structure. In this aspect, immunostimulatory nucleic acid comprises a structure as detailed in formula (I).

Domain A-Domain B-Domain C　　　　　　　(I)

Domains may be from about 2 to about 12 nucleotides in length. Domain A may be 5'-3' or 3'-5' or 2'-5' DNA, RNA, RNA-DNA, DNA-RNA having or not having a palindromic or self-complementary domain containing or not containing at least one dinucleotide selected from the group consisting of CpG, YpG, YpR, CpR, R*pG and R*pR, wherein C is cytidine or 2'deoxycitidine, G is guanosine or 2' deoxyguanosine, Y is cytidine, 2'-deoxythymidine, 2'-deoxycytidine, 2' dideoxy-5-halocytosine, 2' dideoxy-5-nitrocytosine, arabinocytidine, 2'-deoxy-2'-substitutedarabinocytidine, 2'-O-substituted arabinocytidine, 2'-deoxy-5-hydroxycytidine, 2'-deoxy-N-4-alkyl-cytidine, 2'-deoxy-4-thiouridine, other non-natural pyrimidine nucleosides, R* is 1-(2'-deoxy-β-D-ribofuranosyl)-2-oxo-7-deaza-8-methyl-purine; R is guanosine or 2' deoxyguanosine, 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

In certain embodiments, Domain A will have more than one dinucleotide selected from the group consisting of CpG, YpG, YpR, CpR, R*pG and R*pR located in the 5'-end of the Domain A oligonucleotide.

Domain B is a linker joining Domains A and C that may be a 3'-'5' linkage, a 2'-5' linkage, a 3'-3' linkage, a phosphate group, a nucleoside, or a non-nucleoside linker that may be aliphatic, aromatic, aryl, cyclic, chiral, achiral, a peptide, a carbohydrate, a lipid, a fatty acid, mono- tri- or hexapolyethylene glycol, or a heterocyclic moiety.

Domain C may be 5'-3' or 3'-5',2'-5' DNA, RNA, RNA-DNA, DNA-RNA, Poly I-Poly C having or not having a palindromic or self-complementary sequence, which can or cannot have a dinucleotide selected from the group consisting of CpG, YpG, YpR, CpR, R*pG and R*pR, wherein C is cytidine or 2'deoxycitidine, G is guanosine or 2' deoxyguanosine, Y is cytidine, 2'-deoxythymidine, 2'-deoxycytidine, 2' dideoxy-5-halocytosine, 2' dideoxy-5-halocytosine, arabinocytidine, 2'-deoxy-2'-substitutedarabinocytidine, 2'-O-substituted arabinocytidine, 2'-deoxy-5-hydroxycytidine, 2'-deoxy-N-4-alkyl-cytidine, 2'-deoxy-4-thiouridine, other non-natural pyrimidine nucleosides, R* is 1-(2'-deoxy-1-D-ribofuranosyl)-2-oxo-7-deaza-8-methyl-purine; R is guanosine or 2' deoxyguanosine, 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG. In some embodiments, Domain B is preferably a non-nucloetidic linker connecting oligonucleotides of Domain A and Domain C, which are referred to as "immunomers." In certain preferred embodiments, Domain C does not have the dinucleotide CpG, YpG, YpR, CpR, R*pG or R*pR.

In some embodiments, the oligonucleotides of contained in formula (I) are from about 12 to about 50 nucleotides in length. In certain embodiments the oligonucleotides of contained in formula (I) are from about 12 to about 26 nucleotides in length.

By way of non-limiting example, in certain embodiments of this aspect the immunostimulatory nucleic acid will have a structure as detailed in formula (II).

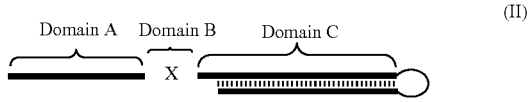

(II)

As one skilled in the art would recognize, there is a secondary structure element in the 3' end of the molecule in the form of an intramolecular stem-loop.

By way of non-limiting example, in certain embodiments of this aspect the immunostimulatory nucleic acid will have a structure as detailed in formula (III)

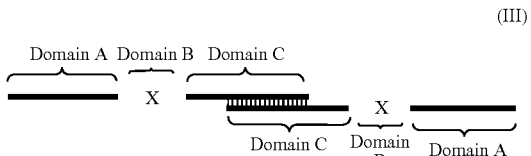

(III)

The structure depicted in formula (III) is referred to herein as a "terminal dimer," since the 3' ends of the two molecules are blocked because the sequences of the two 3' ends are complementary allowing for intermolecular hydrogen bonding. In addition, domains A and A' may or may not be identical, domains B and B' may or may not be identical and domains C and C' may or may not be identical.

By way of non-limiting example, in certain embodiments of this aspect the immunostimulatory nucleic acid will have a structure as detailed in formula (IV).

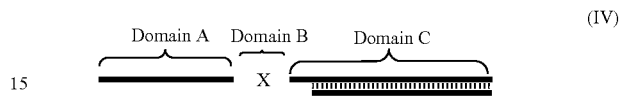

(IV)

As would be recognized by one skilled in the art, the 3' end of the depicted molecule has a secondary structure because the complementary sequence of its 3' end is hydrogen bonded to this region. In certain embodiments, a molecule such as a ligand may be attached to the 3'-end in order to facilitate cellular uptake or improve stability of the molecule.

Non-limiting examples of some nucleic acid molecules of the invention are presented in Tables 24B-C and 25B-C (see below).

In a second aspect, the invention provides immunomer conjugates, comprising an immunomer, as described above, and an antigen conjugated to the immunomer at a position other than the accessible 5' end. In some embodiments, the non-nucleotidic linker comprises an antigen, which is conjugated to the oligonucleotide. In some other embodiments, the antigen is conjugated to the oligonucleotide at a position other than its 3' end. In some embodiments, the antigen produces a vaccine effect.

The antigen is preferably selected from the group consisting of antigens associated with a pathogen, antigens associated with a cancer, antigens associated with an auto-immune disorder, and antigens associated with other diseases such as, but not limited to, veterinary or pediatric diseases, or wherein the antigen is an allergen. For purposes of the invention, the term "associated with" means that the antigen is present when the pathogen, cancer, auto-immune disorder, food allergy, skin allergy, respiratory allergy, asthma or other disease is present, but either is not present, or is present in reduced amounts, when the pathogen, cancer, auto-immune disorder, food allergy, skin allergy, respiratory allergy, or disease is absent.

The immunomer is covalently linked to the antigen, or it is otherwise operatively associated with the antigen. As used herein, the term "operatively associated with" refers to any association that maintains the activity of both immunomer and antigen. Nonlimiting examples of such operative associations include being part of the same liposome or other such delivery vehicle or reagent. In embodiments wherein the immunomer is covalently linked to the antigen, such covalent linkage preferably is at any position on the immunomer other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a third aspect, the invention provides pharmaceutical formulations comprising an immunomer or immunomer conjugate according to the invention and a physiologically acceptable carrier. As used herein, the term "physiologically acceptable" refers to a material that does not interfere with the effectiveness of the immunomer and is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

In a fourth aspect, the invention provides methods for generating an immune response in a vertebrate, such methods comprising administering to the vertebrate an immunomer or immunomer conjugate according to the invention. In some embodiments, the vertebrate is a mammal. For purposes of this invention, the term "mammal" is expressly intended to include humans. In preferred embodiments, the immunomer or immunomer conjugate is administered to a vertebrate in need of immunostimulation.

In the methods according to this aspect of the invention, administration of immunomers can be by any suitable route, including, without limitation, parenteral, oral, sublingual, transdermal, topical, intranasal, intramuscular, intrperitonal, subcutaneous, intradermal, aerosol, intraocular, intratracheal, intrarectal, vaginal, by gene gun, dermal patch or in eye drop or mouthwash form. Administration of the therapeutic compositions of immunomers can be carried out using known procedures at dosages and for periods of time effective to reduce symptoms or surrogate markers of the disease. When administered systemically, the therapeutic composition is preferably administered at a sufficient dosage to attain a blood level of immunomer from about 0.0001 micromolar to about 10 micromolar. For localized administration, much lower concentrations than this may be effective, and much higher concentrations may be tolerated. Preferably, a total dosage of immunomer ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

In certain preferred embodiments, immunomers according to the invention are administered in combination with vaccines, antibodies, cytotoxic agents, allergens, antibiotics, antisense oligonucleotides, peptides, proteins, gene therapy vectors, DNA vaccines and/or adjuvants to enhance the specificity or magnitude of the immune response. In these embodiments, the immunomers of the invention can variously act as adjuvants and/or produce direct immunostimulatory effects.

Either the immunomer or the vaccine, or both, may optionally be linked to an immunogenic protein, such as keyhole limpet hemocyanin (KLH), cholera toxin B subunit, or any other immunogenic carrier protein or nonimmunogenic carrier protein. Any of the plethora of adjuvants may be used including, without limitation, Freund's complete adjuvant, Freund's incomplete adjuvant, KLH, monophosphoryl lipid A (MPL), alum, and saponins, including QS-21, imiquimod, R848, or combinations thereof.

Toll-like receptors (TLRs) function as sensors of infection and induce the activation of innate and adaptive immune responses. TLRs recognize a wide variety of ligands, called pathogen-associated molecular patterns (PAMPs). Upon recognizing conserved pathogen-associated molecular products, TLRs activate host defense responses through their intracellular signalling domain, the Toll/interleukin-1 receptor (TIR) domain, and the downstream adaptor protein MyD88. Dendritic cells and macrophages normally respond to Toll-like receptor (TLR) ligands and cytokines (for example, interleukin-1β; IL-6 and tumour necrosis factor, TNF), which they also produce; natural killer (NK) cells and T cells are also involved in the pro-inflammatory circuit. After TLR stimulation by bacterial compounds, innate immune cells release a range of cytokines. Some examples of TLR ligands include, but are not limited to, lipoproteins; peptidoglycan, zymosan (TLR2), double-stranded RNA, polyI:polyC (TLR3), lipopolysaccharide, heat shock proteins, taxol (TLR4), flagellin (TLR5), and imidazoquinolines-R848, resiquimod, imiquimod; ssRNA (TLR7/8).

For purposes of this aspect of the invention, the term "in combination with" means in the course of treating the same disease in the same patient, and includes administering the immunomer and/or the vaccine and/or the adjuvant in any order, including simultaneous administration, as well as temporally spaced order of up to several days apart. Such combination treatment may also include more than a single administration of the immunomer, and/or independently the vaccine, and/or independently the adjuvant. The administration of the immunomer and/or vaccine and/or adjuvant may be by the same or different routes.

The methods according to this aspect of the invention are useful for model studies of the immune system. The methods are also useful for the prophylactic or therapeutic treatment of human or animal disease. For example, the methods are useful for pediatric and veterinary vaccine applications.

In a fifth aspect, the invention provides methods for therapeutically treating a patient having a disease or disorder, such methods comprising administering to the patient an immunomer or immunomer conjugate according to the invention. In various embodiments, the disease or disorder to be treated is cancer, an autoimmune disorder, airway inflammation, inflammatory disorders, allergy, asthma or a disease caused by a pathogen. Pathogens include bacteria, parasites, fungi, viruses, viroids and prions. Administration is carried out as described for the fourth aspect of the invention.

For purposes of the invention, the term "allergy" includes, without limitation, food allergies atopic dermatitis, allergic rhinitis (also known as hay fever), allergic conjunctivitis, urticaria (also known as hives), respiratory allergies and allergic reactions to other substances such as latex, medications and insect stings or problems commonly resulting from allergic rhinitis-sinusitis and otitis media. The term "airway inflammation" includes, without limitation, asthma. Specific examples of asthma include, but are not limited to, allergic asthma, non-allergic asthma, exercised-induced asthma, occupational asthma, and nocturnal asthma.

Allergic asthma is characterized by airway obstruction associated with allergies and triggered by substances called allergens. Triggers of allergic asthma include, but are not limited to, airborne pollens, molds, animal dander, house dust mites and cockroach droppings. Non-allergic asthma is caused by viral infections, certain medications or irritants found in the air, which aggravate the nose and airways. Triggers of non-allergic asthma include, but are not limited to, airborne particles (e.g., coal, chalk dust), air pollutants (e.g., tobacco smoke, wood smoke), strong odors or sprays (e.g., perfumes, household cleaners, cooking fumes, paints or varnishes), viral infections (e.g., colds, viral pneumonia, sinusitis, nasal polyps), aspirin-sensitivity, and gastroesophageal reflux disease (GERD). Exercise-induced asthma (EIA) is triggered by vigorous physical activity. Symptoms of EIA occur to varying degrees in a majority of asthma sufferers and are likely to be triggered as a result of breathing cold, dry air while exercising. Triggers of EIA include, but are not limited to, breathing airborne pollens during exercise, breathing air pollutants during exercise, exercising with viral respiratory tract infections and exercising in cold, dry air. Occupational asthma is directly related to inhaling irritants and other potentially harmful substances found in the workplace. Triggers of occupational asthma include, but are not limited to, fumes, chemicals, gases, resins, metals, dusts, vapors and insecticides.

As used herein, the term "autoimmune disorder" refers to disorders in which "self" proteins undergo attack by the immune system. Such term includes autoimmune asthma.

Without wishing to be bound to any particular theory, decreased exposure to bacteria may be partially responsible for the increased incidence of, severity of, and mortality due to allergic diseases such as asthma, atopic dermatitis, and rhinitis in the developed countries. This hypothesis is supported by evidence that bacterial infections or products can inhibit the development of allergic disorders in experimental animal models and clinical studies. Bacterial DNA or synthetic oligodeoxynucleotides containing unmethylated CpG dinucleotides in certain sequence contexts (CpG DNA) potently stimulate innate immune responses and thereby acquired immunity. The immune response to CpG DNA includes activation of innate immune cells, proliferation of B cells, induction of Th1 cytokine secretion, and production of immunoglobulins (Ig). The activation of immune cells by CpG DNA occurs via Toll-like receptor 9 (TLR9), a molecular pattern recognition receptor. CpG DNAs induce strong Th1-dominant immune responses characterized by secretion of IL-12 and IFN-$\tilde{\gamma}$. Immunomers (IMOs) alone or as allergen conjugates decrease production of IL-4, IL-5, and IgE and reduce eosinophilia in mouse models of allergic asthma. IMO compounds also effectively reverse established atopic eosinophilic airway disease by converting a Th2 response to a Th1 response.

OVA with alum is commonly used to establish a Th2-dominant immune response in various mouse and rat models. The Th2 immune response includes increased IL-4, IL-5, and IL-13 production, elevated serum levels of total and antigen-specific IgE, IgG 1, and lower levels of IgG2a. IMO compounds prevent and reverse established Th2-dominant immune responses in mice. The co-administration of IMO compounds with OVA/alum to mice reduces IL-4, IL-5, and IL-13 production and induces IFN-γ production in spleen-cell cultures subjected to antigen re-stimulation. Furthermore, IMO compounds inhibit antigen-specific and total IgE and enhance IgG2a production in these mice.

Injection of OVA/alum and IMO compounds induces a lymphocyte antigen-recall response (Th1-type) in mice characterized by low levels of Th2-associated cytokines, IgE and IgG1, and high levels of Th1-associated cytokines and IgG2a. Co-administration of IMO compounds with other kinds of antigens, such as S. masoni egg and hen egg lysozyme, also result in reversal of the Th2-response to a Th1-dominant response in in vitro and in vivo studies. As described herein, IMO compounds effectively prevent development of a Th2 immune response and allow a strong Th1 response.

While Th2 cytokines trigger an Ig isotype switch towards production of IgE and IgG 1, the Th1 cytokine IFN-γ induces production of IgG2a by B-lymphocytes. Mice injected with OVA/alum and IMO compounds produce lower levels of IL-4, IL-5, and IL-13 and higher levels of IFN-γ, accompanied by lower IgE and IgG1 and higher IgG2a levels, than mice injected with OVA/alum alone. This suggests the existence of a close link between Th1-cytokine induction and immunoglobulin isotype switch in mice that receive antigen and IMO compounds.

Serum antigen-specific and total IgE levels are significantly lower in mice receiving OVA/alum and IMO compounds than in mice receiving OVA/alum alone. In contrast, OVA-specific IgG1 levels are insignificantly changed and total IgG1 levels are only slightly decreased compared with mice injected with OVA/alum alone (data not shown). The different response may result from different mechanisms involved in the control of IgE and IgG1 class switch, though both isotypes are influenced by IL-4 and IL-13. For example, IL-6 promotes B lymphocytes to synthesize IgG1 in the presence of IL-4.

In any of the methods according to the invention, the immunomer or immunomer conjugate can be administered in combination with any other agent useful for treating the disease or condition that does not diminish the immunostimulatory effect of the immunomer. For purposes of this aspect of the invention, the term "in combination with" means in the course of treating the same disease in the same patient, and includes administering the immunomer and an agent in any order, including simultaneous administration, as well as any temporally spaced order, for example, from sequentially with one immediately following the other to up to several days apart. Such combination treatment may also include more than a single administration of the immunomer, and independently the agent. The administration of the immunomer and agent may be by the same or different routes.

In any of the methods according to the invention, the agent useful for treating the disease or condition includes, but is not limited to, antigen, allegen, or co-stimulatory molecules such as cytokines, chemokines, protein ligands, trans-activating factors, peptides and peptides comprising modified amino acids. Additionally, the agent can include DNA vectors encoding for antigen or allegen.

The invention provides a kit comprising a immunostimulatory oligonucleotides and/or immunomers, the latter comprising at least two oligonucleotides linked together, such that the immunomer has more than one accessible 5' end, wherein at least one of the oligonucleotides is an immunostimulatory oligonucleotide. In another aspect, the kit comprises an immunostimulatory oligonucleotide and/or immunostimulatory oligonucleotide conjugate and/or immunomer or immunomer conjugate according to the invention and a physiologically acceptable carrier. The kit will generally also include a set of instructions for use.

The examples below are intended to further illustrate certain preferred embodiments of the invention, and are not intended to limit the scope of the invention.

EXAMPLES

Example 1

Synthesis of Oligonucleotides Containing Immunomodulatory Moieties

Oligonucleotides were synthesized on a 1 μmol scale using an automated DNA synthesizer (Expedite 8909; PerSeptive Biosystems, Framingham, Mass.), following the linear synthesis or parallel synthesis procedures outlined in FIGS. 5 and 6.

Deoxyribonucleoside phosphoramidites were obtained from Applied Biosystems (Foster City, Calif.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosponamidite were obtained from Glen Research (Sterling, Va.). β-L-2'-deoxyribonucleoside phosphoramidite, α-2'-deoxyribonucleoside phosphoramidite, mono-DMT-glycerol phosphoramidite and di-DMT-glycerol phosphoramidite were obtained from ChemGenes (Ashland, Mass.). (4-Aminobutyl)-1,3-propanediol phosphoramidite was obtained from Clontech (Palo Alto, Calif.). Arabinocytidine phosphoramidite, arabinoguanosine, arabinothymidine and arabinouridine were obtained from Reliable Pharmaceutical (St. Louis, Mo.). Arabinoguanosine phosphoramidite, arabinothymidine phosphoramidite and arabinouridine phosphoramidite were synthesized at Hybridon, Inc. (Cambridge, Mass.) (Noronha et al. (2000) *Biochem.*, 39:7050-7062).

All nucleoside phosphoramidites were characterized by $^{31}$P and $^{1}$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Analysis of Spleen Cell Proliferation

Figure 8A:
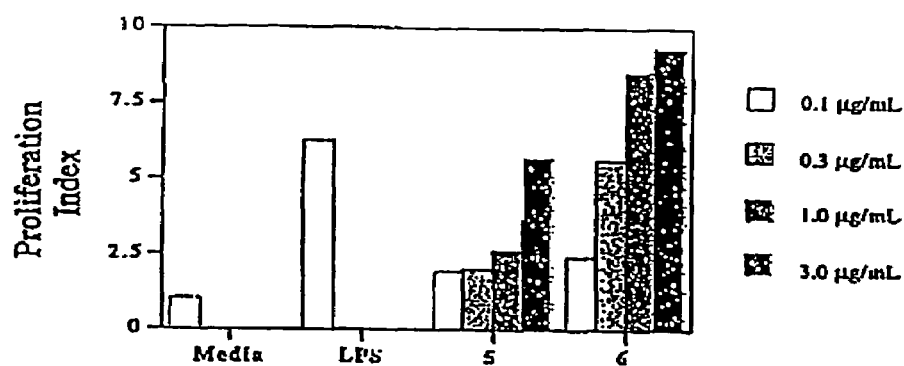
FIG. 8A is a graphic representation of the induction of BALB/c mouse spleen cell proliferation in cell cultures by different concentrations of Immunomers 5 and 6, which have inaccessible and accessible 5'-ends, respectively.

In vitro analysis of splenocyte proliferation was carried out using standard procedures as described previously (see, e.g., Zhao et al., Biochem Pharma 51:173-182 (1996)). The results are shown in FIG. 8A. These results demonstrate that at the higher concentrations, Immunomer 6, having two accessible 5' ends results in greater splenocyte proliferation than does Immunomer 5, having no accessible 5' end or Oligonucleotide 4, with a single accessible 5' end. Immunomer 6 also causes greater splenocyte proliferation than the LPS positive control.

Example 3

In Vivo Splenomegaly Assays

Figure 8B:
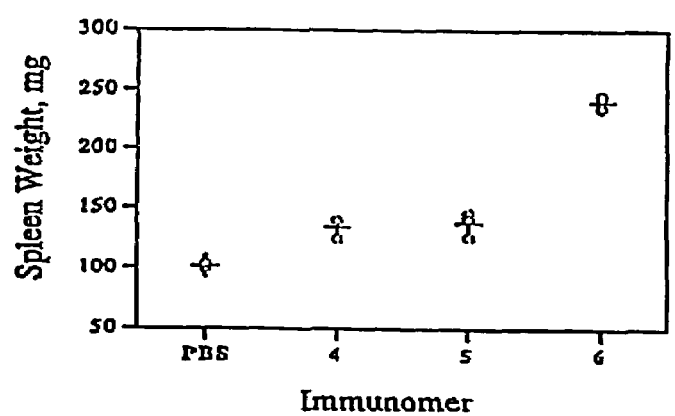
FIG. 8B is a graphic representation of BALB/c mouse spleen enlargement by Immunomers 4-6, which have an immunogenic chemical modification in the 5'-flanking sequence of the CpG motif. Again, the immunomer, which has accessible 5'-ends (6), has a greater ability to increase spleen enlargement compared with Immunomer 5, which does not have accessible 5'-end and with monomeric Oligo 4.
Figure 9A:
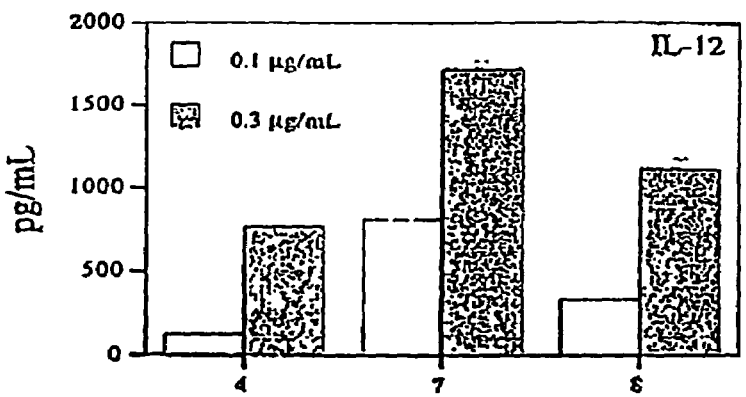
FIG. 9A is a graphic representation of induction of IL-12 by different concentrations of Oligo 4 and Immunomers 7 and 8 in BALB/c mouse spleen cell cultures.
Figure 9B:
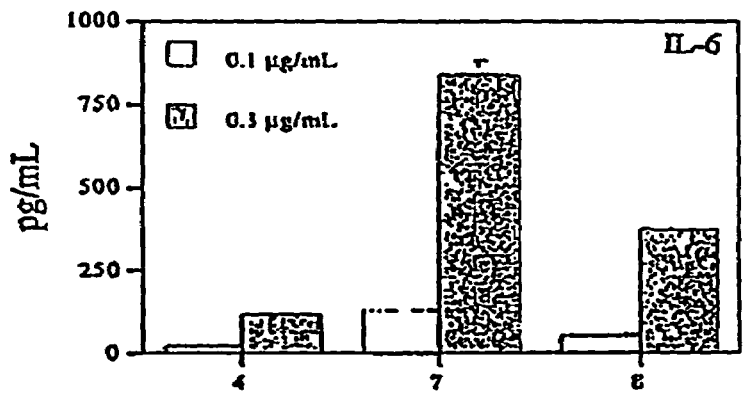
FIG. 9B is a graphic representation of induction of IL-6 by different concentrations of Oligo 4 and Immunomers 7 and 8 in BALB/c mouse spleen cell cultures.
Figure 9C:
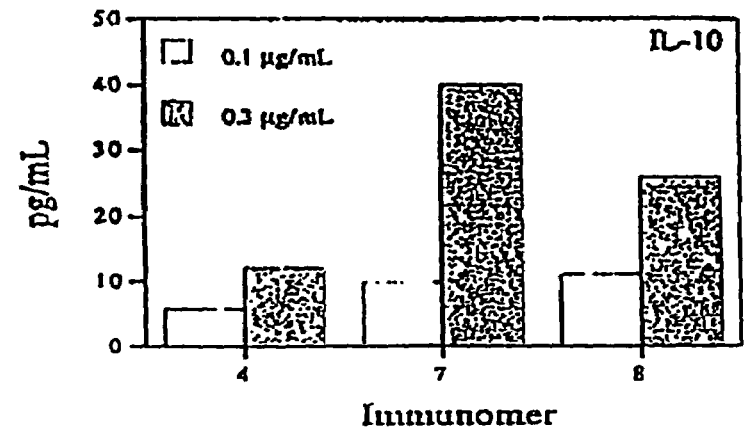
FIG. 9C is a graphic representation of induction of IL-10 by different concentrations of Oligo 4 and Immunomers 7 and 8 in BALB/c mouse spleen cell cultures.
Figure 10A:
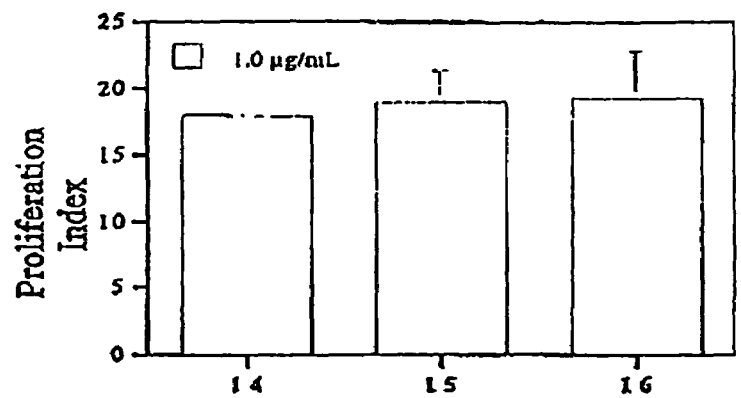
FIG. 10A is a graphic representation of the induction of cell proliferation by Immunomers 14, 15, and 16 in BALB/c mouse spleen cell cultures.
Figure 10B:
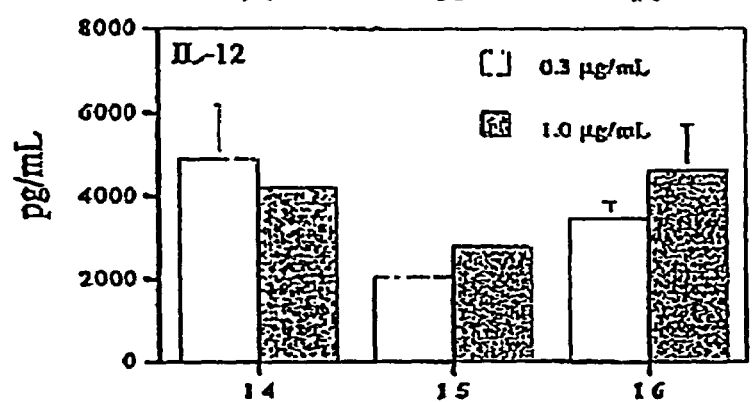
FIG. 10B is a graphic representation of the induction of cell proliferation by IL-12 by different concentrations of Immunomers 14 and 16 in BALB/c mouse spleen cell cultures.
Figure 10C:
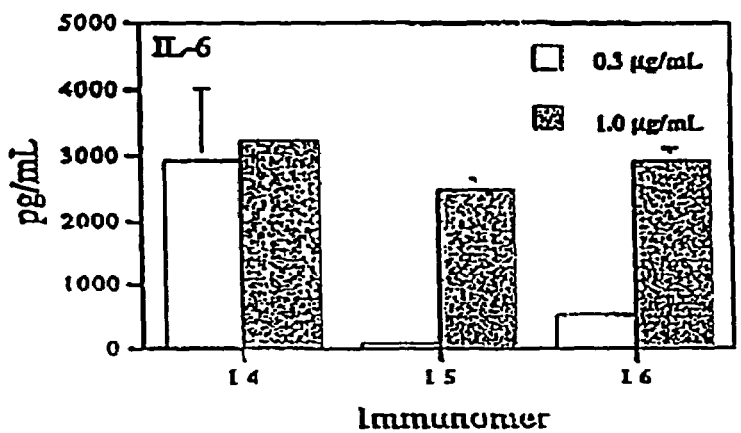
FIG. 10C is a graphic representation of the induction of cell proliferation by IL-6 by different concentrations of Immunomers 14 and 16 in BALB/c mouse spleen cell cultures.
Figure 11A:
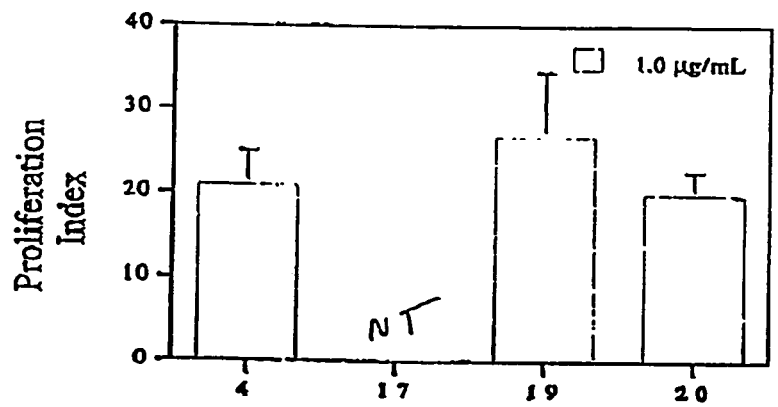
FIG. 11A is a graphic representation of the induction of cell proliferation by Oligo 4 and 17 and Immunomers 19 and 20 in BALB/c mouse spleen cell cultures.
Figure 11B:
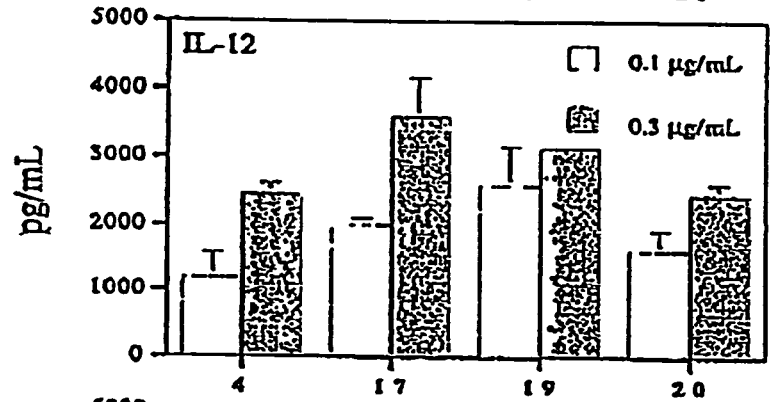
FIG. 11B is a graphic representation of the induction of cell proliferation IL-12 by different concentrations of Oligo 4 and 17 and Immunomers 19 and 20 in BALB/c mouse spleen cell cultures.
Figure 11C:
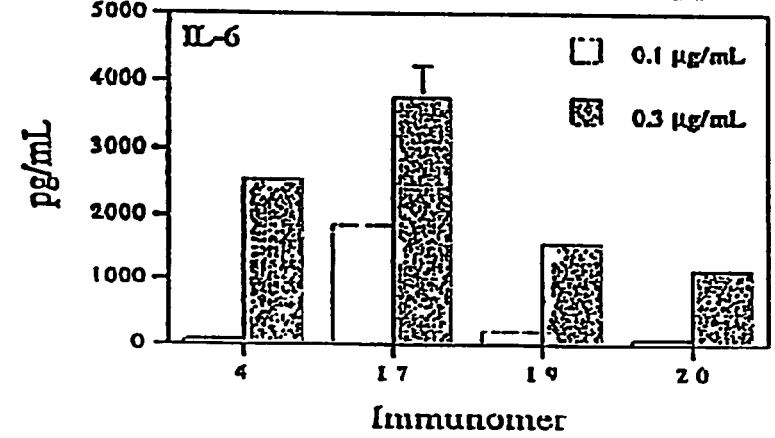
FIG. 11C is a graphic representation of the induction of cell proliferation IL-6 by different concentrations of Oligo 4 and 17 and Immunomers 19 and 20 in BALB/c mouse spleen cell cultures.
Figure 12:
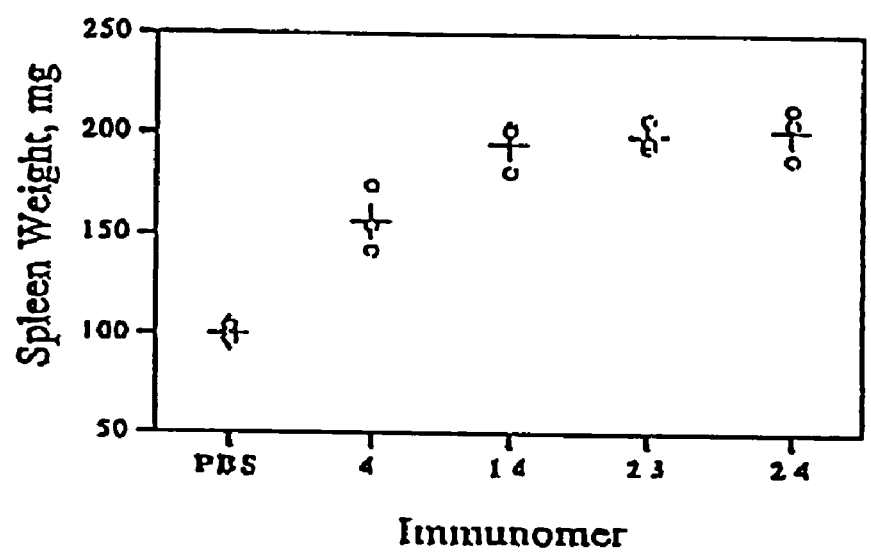
FIG. 12 is a graphic representation of BALB/c mouse spleen enlargement using oligonucleotides 4 and immunomers 14, 23, and 24.

To test the applicability of the in vitro results to an in vivo model, selected oligonucleotides were administered to mice and the degree of splenomegaly was measured as an indicator of the level of immunostimulatory activity. A single dose of 5 mg/kg was administered to BALB/c mice (female, 4-6 weeks old, Harlan Sprague Dawley Inc, Baltic, Conn.) intraperitoneally. The mice were sacrificed 72 hours after oligonucleotide administration, and spleens were harvested and weighed. The results are shown in FIG. 8B. These results demonstrate that Immunomer 6, having two accessible 5' ends, has a far greater immunostimulatory effect than do Oligonucleotide 4 or Immunomer 5.

Example 4

Cytokine Analysis

The secretion of IL-12 and IL-6 in vertebrate cells, preferably BALB/c mouse spleen cells or human PBMC, was measured by sandwich ELISA. The required reagents including cytokine antibodies and cytokine standards were purchased form PharMingen, San Diego, Calif. ELISA plates (Costar) were incubated with appropriate antibodies at 5 μg/mL in PBSN buffer (PBS/0.05% sodium azide, pH 9.6) overnight at 4° C. and then blocked with PBS/1% BSA at 37° C. for 30 minutes. Cell culture supernatants and cytokine standards were appropriately diluted with PBS/10% FBS, added to the plates in triplicate, and incubated at 25° C. for 2 hours. Plates were overlaid with 1 μg/mL appropriate biotinylated antibody and incubated at 25° C. for 1.5 hours. The plates were then washed extensively with PBS-T Buffer (PBS/0.05% Tween 20) and further incubated at 25° C. for 1.5 hours after adding streptavidin conjugated peroxidase (Sigma, St. Louis, Mo.). The plates were developed with Sure, Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments). The results are shown in Table 5A below.

Human peripheral blood mononuclear cells (PBMCs) were isolated from peripheral blood of healthy volunteers by Ficoll-Paque density gradient centrifugation (Histopaque-1077, Sigma, St. Louis, Mo.). Briefly, heparinized blood was layered onto the Histopaque-1077 (equal volume) in a conical centrifuge and centrifuged at 400×g for 30 minutes at room temperature. The buffy coat, containing the mononuclear cells, was removed carefully and washed twice with isotonic phosphate buffered saline (PBS) by centrifugation at 250×g for 10 minutes. The resulting cell pellet was then resuspended in RPMI 1640 medium containing L-glutamine (MediaTech, Inc., Herndon, Va.) and supplemented with 10% heat inactivated FCS and penicillin-streptomycin (100 U/ml). Cells were cultured in 24 well plates for different time periods at $1\times10^6$ cells/ml/well in the presence or absence of oligonucleotides. At the end of the incubation period, supernatants were harvested and stored frozen at −70° C. until assayed for various cytokines including IL-6 (BD Pharmingen, San Diego, Calif.), IL-10 (BD Pharmingen), IL-12 (BioSource International, Camarillo, Calif.), IFN-α (BioSource International) and -γ (BD Pharmingen) and TNF-α (BD Pharmingen) by sandwich ELISA. The results are shown in Tables 5 and 5A below.

In all instances, the levels of IL-12 and IL-6 in the cell culture supernatants were calculated from the standard curve constructed under the same experimental conditions for IL-12 and IL-6, respectively. The levels of IL-10, IFN-gamma and TNF-α in the cell culture supernatants were calculated from the standard curve constructed under the same experimental conditions for IL-10, IFN-gamma and TNF-α, respectively.

TABLE 5

Immunomer Structure and Immunostimulatory Activity in Human PBMC Cultures

| Oligo No. | Sequences and Modification (5'-3') | Oligo Length/ or Each Chain | IL-12 (pg/mL) D1 | IL-12 (pg/mL) D2 | IL-6 (pg/mL) D1 | IL-6 (pg/mL) D2 |
|---|---|---|---|---|---|---|
| 25 SEQ ID NO: 17 | 5'-CTATCTGTCGTTCTCTGT-3' | 18mer (PS) | 184 | 332 | 3077 | 5369 |
| 26 SEQ ID NO: 18 | 5'-TCTGTCR$_1$TTCT-3' \ X$_1$ / 5'-TCTGTCR$_1$TTCT-3' | 11mer (PS) | 237 | 352 | 3724 | 4892 |

TABLE 5-continued

Immunomer Structure and Immunostimulatory Activity in Human PBMC Cultures

| Oligo No. | Sequences and Modification (5'-3') | Oligo Length/ or Each Chain | IL-10 (pg/mL) D1 | IL-10 (pg/mL) D2 | ILN-γ (pg/mL) D1 | ILN-γ (pg/mL) D2 |
|---|---|---|---|---|---|---|
| 25 SEQ ID NO: 17 | 5'-CTATCTGTCGTTCTCTGT-3' | 18mer (PS) | 37 | 88 | 125 | 84 |
| 26 SEQ ID NO: 18 | 5'-TCTGTCR$_1$TTCT-3' \\ $X_1$ / 5'-TCTGTCR$_1$TTCT-3' | 11mer (PS) | 48 | 139 | 251 | 40 |

| Oligo No. | Sequences and Modification (5'-3') | Oligo Length/ or Each Chain | TNF-α (pg/mL) D1 | TNF-α (pg/mL) D2 |
|---|---|---|---|---|
| 25 SEQ ID NO: 17 | 5'-CTATCTGTCGTTCTCTGT-3' | 18mer (PS) | 537 | nt |
| 26 SEQ ID NO: 18 | 5'-TCTGTCR$_1$TTCT-3' \\ $X_1$ / 5'-TCTGTCR$_1$TTCT-3' | 11mer (PS) | 681 | nt |

D1 and D2 are donors 1 and 2.

TABLE 5A

Immunomer Structure and Immunostimulatory Activity in BALB/c Mouse Spleen Cell Cultures

| Oligo No. | Sequences and Modification (5'-3') | Oligo Length/ or Each Chain | IL-12 (pg/mL) 3 μg/mL | IL-6 (pg/mL) 10 μg/mL |
|---|---|---|---|---|
| 26 SEQ ID NO: 18 | 5'-TCTGTCR$_1$TTCT-3' \\ $X_1$ / 5'-TCTGTCR$_1$TTCT-3' | 11mer (PS) | 870 | 10670 |
| 27 SEQ ID NO: 19 | 5'-TCTGTCR$_2$TTCT-3' \\ $X_1$ / 5'-TCTGTCR$_2$TTCT-3' | 11mer (PS) | 1441 | 7664 |
| 28 SEQ ID NO: 20 | 5'-TCTGTY$_2$R$_2$TTCT-3' \\ $X_1$ / 5'-TCTGTY$_2$R$_2$TTCT-3' | 11mer (PS) | 1208 | 1021 |
| 29 SEQ ID NO: 21 | 5'-XXTCTGTCR$_1$TTCT-3' \\ $X_1$ / 5'-XXTCTGTCR$_1$TTCT-3' | 11mer (PS) | 182 | 1013 |
| 30 SEQ ID NO: 22 | 5'-CTGTCR$_2$TTCTCTGT-3' \\ $X_1$ / 5'-CTGTCR$_2$TTCTCTGT-3' | 14mer (PO) | 264 | 251 |
| 31 SEQ ID NO: 23 | 5'-CTGTY$_2$R$_2$TTCTCTGT-3' \\ $X_1$ / 5'-CTGTY$_2$R$_2$TTCTCTGT-3' | 14mer (PO) | 149 | 119 |

TABLE 5A-continued

Immunomer Structure and Immunostimulatory Activity in BALB/c Mouse Spleen Cell Cultures

| Oligo No. | Sequences and Modification (5'-3') | Oligo Length/ or Each Chain | IL-12 (pg/mL) 3 µg/mL | IL-6 (pg/mL) 10 µg/mL |
|---|---|---|---|---|
| 32 SEQ ID NO: 24 | 5'-TCTGACR$_1$TTCT-3' \ X$_1$ / 5'-TCTGACR$_1$TTCT-3' | 11mer (PS) | 2520 | 9699 |
| 33 SEQ ID NO: 25 | 5'-XXTCTGACR$_1$TTCT-3' \ X$_1$ / 5'-XXTCTGACR$_1$TTCT-3' | 11mer (PS) | 2214 | 16881 |
| 34 SEQ ID NO: 26 | 5'-TCTGACR$_2$TTCT-3' \ X$_1$ / 5'-TCTGACR$_2$TTCT-3' | 11mer PS) | 3945 | 10766 |
| 35 SEQ ID NO: 27 | 5'-TCTGAY$_2$R$_2$TTCT-3' \ X$_1$ / 5'-TCTGAY$_2$R$_2$TTCT-3' | 11mer (PS) | 2573 | 19411 |
| 36 SEQ ID NO: 28 | 5'-CTGAY$_2$GTTCTCTGT-3' \ X$_1$ / 5'-CTGAY$_2$GTTCTCTGT-3' | 14mer (PO) | 2699 | 408 |
| 37 SEQ ID NO: 29 | 5'-CTGACR$_2$TTCTCTGT-3' \ X$_1$ / 5'-CTGACR$_2$TTCTCTGT-3' | 14mer (PO) | 839 | 85 |
| 38 SEQ ID NO: 30 | 5'-CTGAY$_2$R$_2$TTCTCTGT-3' \ X$_1$ / 5'-CTGAY$_2$R$_2$TTCTCTGT-3' | 14mer (PO) | 143 | 160 |

Normal phase represents a phosphorothioate linkage; Italic phase represents a phosphodiester linkage.

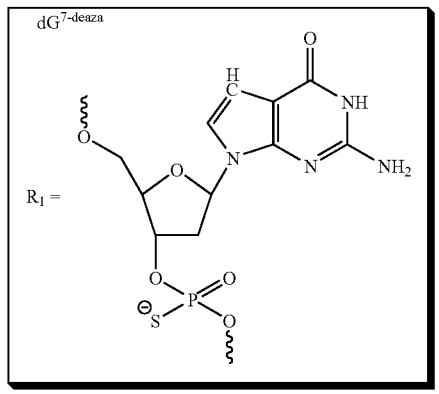

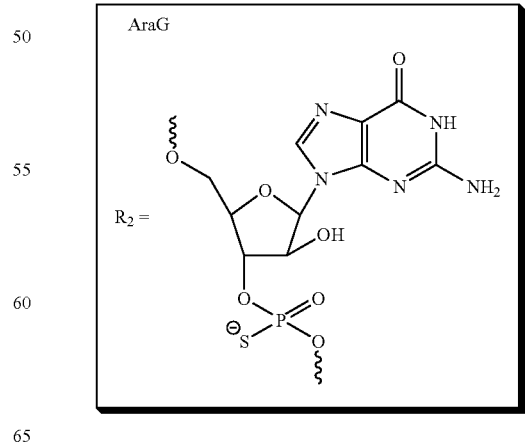

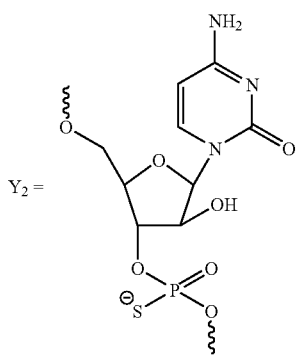

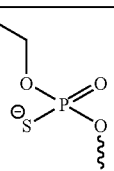

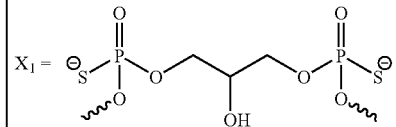

Figure 7A:
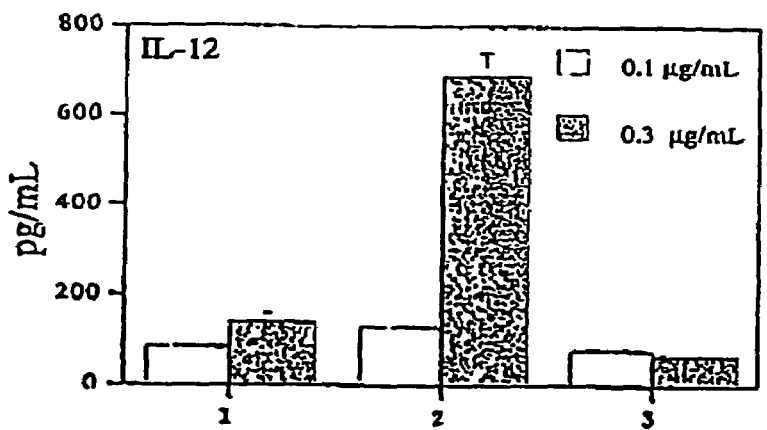
FIG. 7A is a graphic representation of the induction of IL-12 by immunomers 1-3 in BALB/c mouse spleen cell cultures. These data suggest that Immunomer 2, which has accessible 5'-ends, is a stronger inducer of IL-12 than monomeric Oligo 1, and that Immunomer 3, which does not have accessible 5'-ends, has equal or weaker ability to produce immune stimulation compared with oligo 1.
Figure 7B:
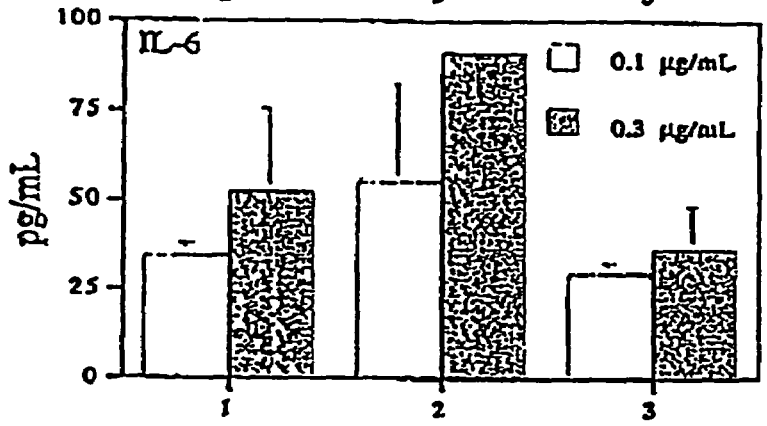
FIG. 7B is a graphic representation of the induction of IL-6 (top to bottom, respectively) by Immunomers 1-3 in BALB/c mouse spleen cells cultures. These data suggest that Immunomer 2, which has accessible 5'-ends, is a stronger inducer of IL-6 than monomeric Oligo 1, and that Immunomer 3, which does not have accessible 5'-ends, has equal or weaker ability to induce immune stimulation compared with Oligo 1.
Figure 7C:
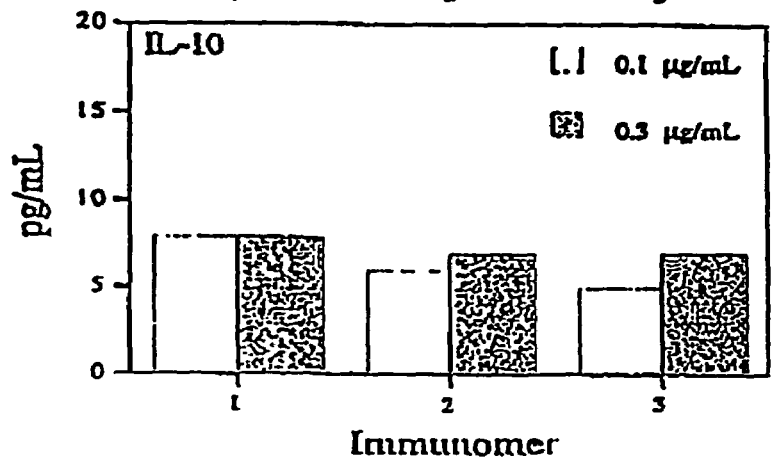
FIG. 7C is a graphic representation of the induction of IL-10 by Immunomers 1-3 (top to bottom, respectively) in BALB/c mouse spleen cell cultures.

In addition, the results shown in FIGS. 7A-C demonstrate that Oligonucleotide 2, with two accessible 5' ends elevates IL-12 and IL-6, but not IL-10 at lower concentrations than Oligonucleotides 1 or 3, with one or zero accessible 5' ends, respectively.

Example 5

Effect of Chain Length on Immunostimulatory Activity of Immunomers

In order to study the effect of length of the oligonucleotide chains, immunomers containing 18, 14, 11, and 8 nucleotides in each chain were synthesized and tested for immunostimulatory activity, as measured by their ability to induce secretion of the cytokines IL-12 and IL-6 in BALB/c mouse spleen cell cultures (Tables 6-8). In this, and all subsequent examples, cytokine assays were carried out in BALB/c spleen cell cultures as described in Example 4.

TABLE 6

Immunomer Structure and Immunostimulatory Activity

| No. | Sequences and Modification (5'-3') | Oligo Length/ or Each Chain | IL-12 (pg/mL) @ 0.3 µg/mL | IL-6 (pg/mL) @ 0.3 µg/mL |
|---|---|---|---|---|
| 4 SEQ ID NO: 2 | 5'-CTATCTGACGTTCTCTGT-3' | 18mer | 1802 | 176 |
| 39 SEQ ID NO: 2 | 5'-CTATCTGACGTTCTCTGT-3'⎤<br>           ⎬3'-T-5'<br>5'-CTATCTGACGTTCTCTGT-3'⎦ | 18mer | 1221 | 148 |
| 40 SEQ ID NO: 8 | 5'-CTGACGTTCTCTGT-3'⎤<br>           ⎬3'-T-5'<br>5'-CTGACGTTCTCTGT-3'⎦ | 14mer | 2107 | 548 |
| 41 SEQ ID NO: 13 | 5'-TCTGACGTTCT-3'⎤<br>           ⎬3'-T-5'<br>5'-TCTGACGTTCT-3'⎦ | 11mer | 3838 | 1191 |
| 42 N/A | 5'-GACGTTCT-3'⎤<br>           ⎬3'-T-5'<br>5'-GACGTTCT-3'⎦ | 8mer | 567 | 52 |

TABLE 7

Immunomer Structure and Immunostimulatory Activity

| No. | Sequences and Modification (5'-3') | Oligo Length/ or Each Chain | IL-12 (pg/mL) 1 µg/mL | IL-6 (pg/mL) 1 µg/mL |
|---|---|---|---|---|
| 25 SEQ ID NO: 17 | 5'-CTATCTGTCGTTCTCTGT-3' | 18mer | 291 | 85 |

TABLE 7-continued

Immunomer Structure and Immunostimulatory Activity

| No. | Sequences and Modification (5'-3') | Oligo Length/ or Each Chain | IL-12 (pg/mL) 1 μg/mL | IL-6 (pg/mL) 1 μg/mL |
|---|---|---|---|---|
| 43 SEQ ID NO: 17 | 5'-CTATCTGTCGTTCTCTGT-3'<br>          3'-T-5'<br>5'-CTATCTGTCGTTCTCTGT-3' | 18mer | 430 | 39 |
| 44 SEQ ID NO: 31 | 5'-CTGTCGTTCTCTGT-3'<br>          3'-T-5'<br>5'-CTGTCGTTCTCTGT-3' | 14mer | 813 | 59 |
| 45 SEQ ID NO: 32 | 5'-CTGTCGTTCTCT-3'<br>          3'-T-5'<br>5'-CTGTCGTTCTCT-3' | 12mer | 1533 | 123 |
| 46 SEQ ID NO: 33 | 5'-TCTGTCGTTCT-3'<br>          3'-T-5'<br>5'-TCTGTCGTTCT-3' | 11mer | 2933 | 505 |
| 47 N/A | 5'-GTCGTTCT-3'<br>          3'-T-5'<br>5'-GTCGTTCT-3' | 8mer | 1086 | 26 |
| 48 N/A | 5'-GTCGTTC-3'<br>          3'-T-5'<br>5'-GTCGTTC-3' | 7mer | 585 | 34 |
| 49 N/A | 5'-GTCGTT-3'<br>          3'-T-5'<br>5'-GTCGTT-3' | 6mer | 764 | 76 |
| 50 N/A | 5'-TCGTT-3'<br>          3'-T-5'<br>5'-TCGTT-3' | 5mer | 28 | 29 |

TABLE 8

Immunomer Structure and Immunostimulatory Activity

| No. | Sequences and Modification (5'-3') | Oligo Length/ or Each Chain | IL-12 (pg/mL) 1 μg/mL | IL-6 (pg/mL) 1 μg/mL |
|---|---|---|---|---|
| 51 SEQ ID NO: 34 | 5'-CTCACTTTCGTTCTCTGT-3' | 18mer | 91 | 73 |
| 52 SEQ ID NO: 34 | 5'-CTCACTTTCGTTCTCTGT-3'<br>          3'-T-5'<br>5'-CTCACTTTCGTTCTCTGT-3' | 18mer | 502 | 99 |
| 53 SEQ ID NO: 35 | 5'-CTTTCGTTCTCTGT-3'<br>          3'-T-5'<br>5'-CTTTCGTTCTCTGT-3' | 14mer | 683 | 119 |

TABLE 8-continued

Immunomer Structure and Immunostimulatory Activity

| No. | Sequences and Modification (5'-3') | Oligo Length/ or Each Chain | IL-12 (pg/mL) 1 µg/mL | IL-6 (pg/mL) 1 µg/mL |
|---|---|---|---|---|
| 54 SEQ ID NO: 36 | 5'-CTTTCGTTCTCT-3'⎤<br>⎯ 3'-T-5'<br>5'-CTTTCGTTCTCT-3'⎦ | 12mer | 633 | 102 |
| 55 N/A | 5'-TTCGTTCT-3'⎤<br>⎯ 3'-T-5'<br>5'-TTCGTTCT-3'⎦ | 8mer | 657 | 243 |
| 56 N/A | 5'-TCGTTCT-3'⎤<br>⎯ 3'-T-5'<br>5'-TCGTTCT-3'⎦ | 7mer | 592 | 1252 |

The results suggest that the immunostimulatory activity of immunomers increased as the length of the oligonucleotide chains is decreased from 18-mers to 7-mers. Immunomers having oligonucleotide chain lengths as short as 6-mers or 5-mers showed immunostimulatory activity comparable to that of the 18-mer oligonucleotide with a single 5' end. However, immunomers having oligonucleotide chain lengths as short as 6-mers or 5-mers have increased immunostimulatory activity when the linker is in the length of from about 2 angstroms to about 200 angstroms.

Example 6

Immunostimulatory Activity of Immunomers Containing A Non-Natural Pyrimidine or Non-Natural Purine Nucleoside As shown in Tables 9-11, immunostimulatory activity was maintained for immunomers of various lengths having a non-natural pyrimidine nucleoside or non-natural purine nucleoside in the immunostimulatory dinucleotide motif.

TABLE 9

Immunomer Structure and Immunostimulatory Activity

| No. | Sequences and Modification (5'-3') | Oligo Length/ or Each Chain | IL-12 (pg/mL) @ 3 µg/mL | IL-6 (pg/mL) @ 3 µg/mL |
|---|---|---|---|---|
| 51 SEQ ID NO: 34 | 5'-CTCACTTTCGTTCTCTGT-3' | 18 mer | 404 | 348 |
| 57 SEQ ID NO: 37 | 5'-TCTTTYGTTCT-3'⎤<br>⎯ 3'-T-5'<br>5'-TCTTTYGTTCT-3'⎦ | 11 mer | 591 | 365 |
| 58 SEQ ID NO: 38 | 5'-TCTTTCRTTCT-3'⎤<br>⎯ 3'-T-5'<br>5'-TCTTTCRTTCT-3'⎦ | 11 mer | 303 | 283 |
| 59 N/A | 5'-TTYGTTCT-3'⎤<br>⎯ 3'-T-5'<br>5'-TTYGTTCT-3'⎦ | 8 mer | 55 | 66 |
| 60 N/A | 5'-TTCRTTCT-3'⎤<br>⎯ 3'-T-5'<br>5'-TTCRTTCT-3'⎦ | 8 mer | 242 | 143 |

TABLE 9-continued

Immunomer Structure and Immunostimulatory Activity

| No. | Sequences and Modification (5'-3') | Oligo Length/ or Each Chain | IL-12 (pg/mL) @ 3 μg/mL | IL-6 (pg/mL) @ 3 μg/mL |
|---|---|---|---|---|

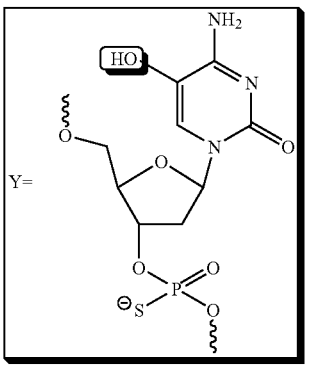

TABLE 10

Immunomer Structure and Immunostimulatory Activity

| No. | Sequences and Modification (5'-3') | Oligo Length/ or Each Chain | IL-12 (pg/mL) 3 μg/mL | IL-6 (pg/mL) 3 μg/mL |
|---|---|---|---|---|
| 25 SEQ ID NO: 17 | 5'-CTATCTGTCGTTCTCTGT-3' | 18 mer | 379 | 339 |
| 61 SEQ ID NO: 39 | 5'-TCTGTYGTTCT-3'<br>5'-TCTGTYGTTCT-3'  ⎤ 3'-T-5' | 11 mer | 1127 | 470 |
| 62 SEQ ID NO: 18 | 5'-TCTGTCRTTCT-3'<br>5'-TCTGTCRTTCT-3'  ⎤ 3'-T-5' | 11 mer | 787 | 296 |
| 63 N/A | 5'-GTYGTTCT-3'<br>5'-GTYGTTCT-3'  ⎤ 3'-T-5' | 8 mer | 64 | 126 |
| 64 N/A | 5'-GTCRTTCT-3'<br>5'-GTCRTTCT-3'  ⎤ 3'-T-5' | 8 mer | 246 | 113 |

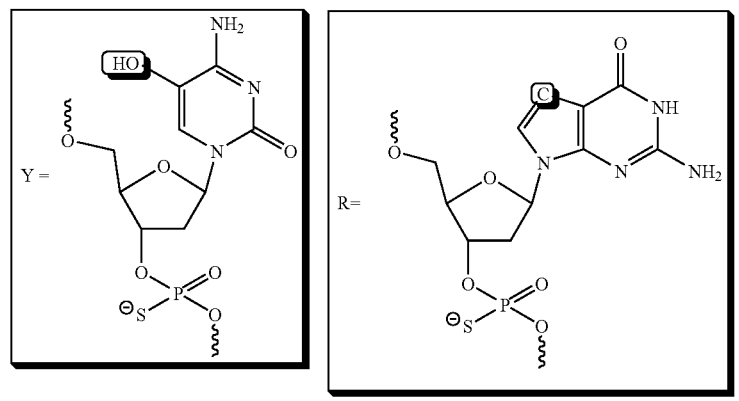

TABLE 11

Immunomer Structure and Immunostimulatory Activity

| No. | Sequences and Modification (5'-3') | Oligo Length/ or Each Chain | IL-12 (pg/mL) 3 µg/mL | IL-6 (pg/mL) 3 µg/mL |
|---|---|---|---|---|
| 4 SEQ ID NO: 2 | 5'-CTATCTGACGTTCTCTGT-3' | 18 mer | 1176 | 1892 |
| 65 SEQ ID NO: 4 | 5'-CTATCTGAYGTTCTCTGT-3' ⎤<br>5'-CTATCTGAYGTTCTCTGT-3' ⎦ 3'-T-5' | 18 mer | 443 | 192 |
| 66 SEQ ID NO: 5 | 5'-CTATCTGACRTTCTCTGT-3' ⎤<br>5'-CTATCTGACRTTCTCTGT-3' ⎦ 3'-T-5' | 18 mer | 627 | 464 |
| 67 SEQ ID NO: 6 | 5'-CTGAYGTTCTCTGT-3' ⎤<br>5'-CTGAYGTTCTCTGT-3' ⎦ 3'-T-5' | 14 mer | 548 | 152 |
| 68 SEQ ID NO: 7 | 5'-CTGACRTTCTCTGT-3' ⎤<br>5'-CTGACRTTCTCTGT-3' ⎦ 3'-T-5' | 14 mer | 1052 | 1020 |
| 69 SEQ ID NO: 40 | 5'-TCTGAYGTTCT-3' ⎤<br>5'-TCTGAYGTTCT-3' ⎦ 3'-T-5' | 11 mer | 2050 | 2724 |
| 70 SEQ ID NO: 24 | 5'-TCTGACRTTCT-3' ⎤<br>5'-TCTGACRTTCT-3' ⎦ 3'-T-5' | 11 mer | 1780 | 1741 |
| 71 N/A | 5'-GAYGTTCT-3' ⎤<br>5'-GAYGTTCT-3' ⎦ 3'-T-5' | 8 mer | 189 | 55 |
| 72 | 5'-GACRTTCT-3' ⎤<br>5'-GACRTTCT-3' ⎦ 3'-T-5' | 8 mer | 397 | 212 |

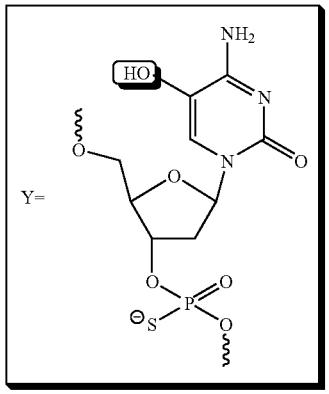

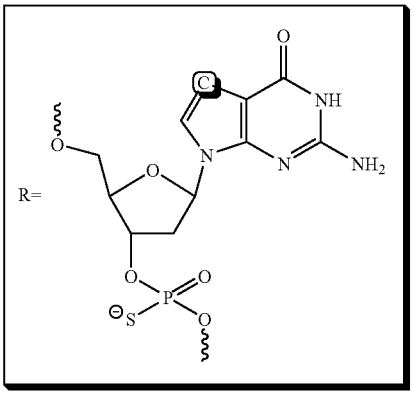

Example 7

Effect of the Linker on Immunostimulatory Activity

In order to examine the effect of the length of the linker connecting the two oligonucleotides, immunomers that contained the same oligonucleotides, but different linkers were synthesized and tested for immunostimulatory activity. The results shown in Table 12 suggest that linker length plays a role in the immunostimulatory activity of immunomers. The best immunostimulatory effect was achieved with C3- to C6-alkyl linkers or abasic linkers having interspersed phosphate charges.

TABLE 12

Immunomer Structure and Immunostimulatory Activity

| No. | Sequences and Modification (5'-3') | Oligo Length/ or Each Chain | IL-12 (pg/mL) 0.3 µg/mL | IL-6 (pg/mL) 1 µg/mL |
|---|---|---|---|---|
| 4 SEQ ID NO: 2 | 5'-CTATCTGACGTTCTCTGT-3' | 18 mer | 257 | 635 |
| 73 SEQ ID NO: 41 | 5'-CTGACGTTCT-3' ⟩$X_1$<br>5'-CTGACGTTCT-3' | 10 mer | 697 | 1454 |
| 74 SEQ ID NO: 41 | 5'-CTGACGTTCT-3' ⟩$X_2$<br>5'-CTGACGTTCT-3' | 10 mer | 1162 | 669 |
| 75 SEQ ID NO: 41 | 5'-CTGACGTTCT-3' ⟩$X_3$<br>5'-CTGACGTTCT-3' | 10 mer | 1074 | 1375 |
| 76 SEQ ID NO: 41 | 5'-CTGACGTTCT-3' ⟩$X_4$<br>5'-CTGACGTTCT-3' | 10 mer | 563 | 705 |
| 77 SEQ ID NO: 41 | 5'-CTGACGTTCT-3' ⟩$X_5$<br>5'-CTGACGTTCT-3' | 10 mer | 264 | 543 |
| 78 SEQ ID NO: 41 | 5'-CTGACGTTCT-3' ⟩$X_6$<br>5'-CTGACGTTCT-3' | 10 mer | 1750 | 2258 |
| 79 SEQ ID NO: 41 | 5'-CTGACGTTCT-3' ⟩$(X_3psX_3)$<br>5'-CTGACGTTCT-3' | 10 mer | 2255 | 2034 |
| 80 SEQ ID NO: 41 | 5'-CTGACGTTCT-3' ⟩$(X_3psX_3psX_3)$<br>5'-CTGACGTTCT-3' | 10 mer | 1493 | 1197 |
| 81 SEQ ID NO: 41 | 5'-CTGACGTTCT-3' ⟩$(X_6psX_6)$<br>5'-CTGACGTTCT-3' | 10 mer | 3625 | 2642 |
| 82 SEQ ID NO: 41 | 5'-CTGACGTTCT-3' ⟩$(X_6psX_6psX_6)$<br>5'-CTGACGTTCT-3' | 10 mer | 4248 | 2988 |
| 83 SEQ ID NO: 41 | 5'-CTGACGTTCT-3' ⟩$PO_3S$<br>5'-CTGACGTTCT-3' | 10 mer | 1241 | 1964 |

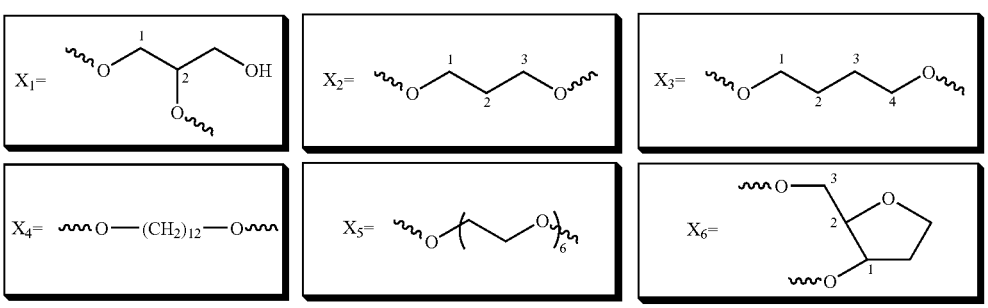

Example 8

Effect of Oligonucleotide Backbone on Immunostimulatory Activity

In general, immunostimulatory oligonucleotides that contain natural phosphodiester backbones are less immunostimulatory than are the same length oligonucleotides with a phosphorothioate backbones. This lower degree of immunostimulatory activity could be due in part to the rapid degradation of phosphodiester oligonucleotides under experimental conditions. Degradation of oligonucleotides is primarily the result of 3'-exonucleases, which digest the oligonucleotides from the 3' end. The immunomers of this example do not contain a free 3' end. Thus, immunomers with phosphodiester backbones should have a longer half life under experimental conditions than the corresponding monomeric oligonucleotides, and should therefore exhibit improved immunostimulatory activity. The results presented in Table 13 demonstrate this effect, with Immunomers 84 and 85 exhibiting immunostimulatory activity as determined by cytokine induction in BALB/c mouse spleen cell cultures.

TABLE 13

Immunomer Structure and Immunostimulatory Activity

| No. | Sequences and Modification (5'-3') | Oligo Length/ or Each Chain | IL-12 (pg/mL) 0.3 µg/mL | IL-6 (pg/mL) 1 µg/mL |
|---|---|---|---|---|
| 4 SEQ ID NO: 2 | 5'-CTATCTGACGTTCTCTGT-3' | 18mer | 225 | 1462 |
| 84 SEQ ID NO: 8 | 5'-CTGACGTTCTCTGT-3' ⎤<br>                          ├─ 3'-T-5'<br>5'-CTGACGTTCTCTGT-3' ⎦ | 14mer | 1551 | 159 |
| 85 SEQ ID NO: 8 | 5'-LLCTGACGTTCTCTGT-3' ⎤<br>                            ├─ 3'-T-5'<br>5'-LLCTGACGTTCTCTGT-3' ⎦ | 14mer | 466 | 467 |

L = C3-Linker

Example 9

Synthesis of Immunomers in Tables 12-15

Oligonucleotides were synthesized on 1 µmol scale using an automated DNA synthesizer (Expedite 8909 PerSeptive Biosystems). Deoxynucleoside phosphoramidites were obtained from Applied Biosystems (Foster City, Calif.). 7-Deaza-2'-deoxyguanosine phosphoramidite was obtained from Glen Research (Sterling Va.). 1,3-Bis-DMT-glycerol-CPG was obtained from ChemGenes (Ashland, Mass.). Modified nucleosides were incorporated into the oligonucleotides at specific site using normal coupling cycles. After the synthesis, oligonucleotides were deprotected using concentrated ammonium hydroxide and purified by reversed-phase HPLC, followed by dialysis. Purified oligonucleotides as sodium salt form were lyophilized prior to use. Purity of oligonucleotides was checked by CGE and MALDI-TOF MS (Bruker Proflex III MALDI-TOF Mass spectrometer).

Example 10

Immunomer Stability

Oligonucleotides were incubated in PBS containing 10% bovine serum at 37° C for 4, 24 or 48 hours. Intact oligonucleotide was determined by capillary gel electrophoresis. The results are shown in Table 14.

TABLE 14

Digestion of Oligonucleotides in 10% Bovine Serum PBS Solution

| Oligo No. | Sequences and Modification (5'-3') | CE analysis of oligos (% intact oligo remained after digestion) | | |
|---|---|---|---|---|
| | | after 4 h | After 24 h | after 48 h |
| 4 SEQ ID NO: 2 | 5-CTATCTGACGT TCTCTGT-3'/PS | 90.9 | 71.8 | 54.7 |
| 26 SEQ ID NO: 42 | (5'-TCTGTCGTT CT)₂S/PS (G = dG$^{deaza}$) | 97.1 | 91.0 | 88.1 |
| 86 SEQ ID NO: 43 | (5'-CTGTCGTTC TCTGT)₂S/PO | | 37.8 | 22.5 |
| 87 SEQ ID NO: 31 | (5'-XXCTGTCGT TCTCTGT)₂S/PO | 73.1 | 56.8 | 36.8 |
| 88 SEQ ID NO: 44 | (5'-UCTGTCGTT CTCTGT)₂S/PO | | 48.4 | 36.7 |

X = C3-Linker,
U, C = 2'-OMe-ribonucleoside

Example 11

Effect of Accessible 5' Ends on Immunostimulatory Activity

BALB/c mouse (4-8 weeks) spleen cells were cultured in RPMI complete medium. Murine macrophage-like cells, J774 (American Type Culture Collection, Rockville, Md.) were cultured in Dulbecco's modified Eagle's medium supplemented with 10% (v/v) FCS and antibiotics (100 IU/mL of penicillin G/streptomycin). All other culture reagents were purchased from Mediatech (Gaithersburg, Md.).

ELISAs for IL-12 and IL-6. BALB/c mouse spleen or J774 cells were plated in 24-well dishes at a density of 5×10⁶ or 1×10⁶ cells/mL, respectively. The IMO compounds dissolved in TE buffer (10 mM Tris-HCl, pH 7.5, 1 mM EDTA) was added to a final concentration of 0.03, 0.1, 0.3, 1.0, 3.0, or 10.0 µg/mL to mouse spleen cell cultures and 1.0, 3.0, or 10.0 µg/mL to J774 cell cultures. The cells were then incubated at 37° C. for 24 hr and the supernatants were collected for ELISA assays. The experiments were performed two or three times for each IMO compound in triplicate for each concentration.

The secretion of IL-12 and IL-6 was measured by sandwich ELISA. The required reagents, including cytokine antibodies and standards were purchased from PharMingen. ELISA plates (Costar) were incubated with appropriate antibodies at 5 μg/mL in PBSN buffer (PBS/0.05% sodium azide, pH 9.6) overnight at 4° C. and then blocked with PBS/1% BSA at 37° C. for 30 min. Cell culture supernatants and cytokine standards were appropriately diluted with PBS/1% BSA, added to the plates in triplicate, and incubated at 25° C. for 2 hr. Plates were washed and incubated with 1 μg/mL of appropriate biotinylated antibody and incubated at 25° C. for 1.5 hr. The plates were washed extensively with PBS/0.05% Tween 20 and then further incubated at 25° C. for 1.5 hr after the addition of streptavidine-conjugated peroxidase (Sigma). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments) at 450 nm. The levels of IL-12 and IL-6 in the cell culture supernatants were calculated from the standard curve constructed under the same experimental conditions for IL-12 and IL-6, respectively.

The results are shown in Table 15.

TABLE 15

Phosphorothioate CpG DNA sequences and modifications used in the study[a] (All oligonucleotides shown are disclosed as SEQ ID NO: 45)

| CpG DNA # | Sequence | Length | 5'-end | 3'-end |
|---|---|---|---|---|
| 89 | 5'-TCCATGACGTTCCTGATGC-3' | 19-mer | 1 | 1 |
| 90 | 5'-TCCATGACGTTCCTGATGC-3'-b | 19-mer | 1 | blocked |
| 91 | 5'-TCCATGACGTTCCTGATGC-3'-3'-g-5' | 20-mer | 2 | blocked |
| 92 | 5'-TCCATGACGTTCCTGATGC-3'-3'-h-5' | 23-mer | 2 | blocked |
| 93 | 5'-TCCATGACGTTCCTGATGC-3'-3'-i-5' | 27-mer | 2 | blocked |
| 94 | 5'-TCCATGACGTTCCTGATGC-3'-3'-j-5' | 38-mer | 2 | blocked |
| 95 | b-5'-TCCATGACGTTCCTGATGC-3' | 19-mer | blocked | 1 |
| 96 | 3'-c-5'-5'-TCCATGACGTTCCTGATGC-3' | 20-mer | blocked | 2 |
| 97 | 3'-d-5'-5'-TCCATGACGTTCCTGATGC-3' | 23-mer | blocked | 2 |
| 98 | 3'-e-5'-5'-TCCATGACGTTCCTGATGC-3' | 27-mer | blocked | 2 |
| 99 | 3'-f-5'-5'-TCCATGACGTTCCTGATGC-3' | 38-mer | blocked | 2 |
| 100 | 5'-TCCATGACGTTCCTGATGC-3'-k | 19-mer | 1 | blocked |
| 101 | l-5'-TCCATGACGTTCCTGATGC-3' | 19-mer | blocked | 1 |

[a]See Chart I for chemical structures b-l; 5'-CG-3' dinucleotide is shown underlined Chart 1 (SEQ ID NOS 46-48, respectively in order of appearance)

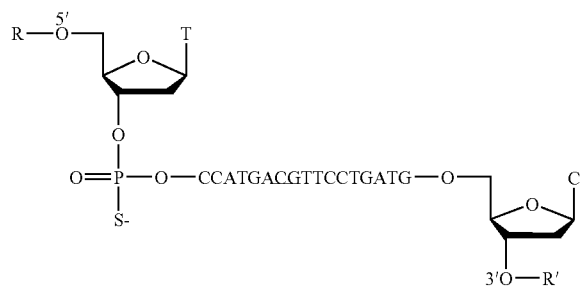

1: R, R' = a

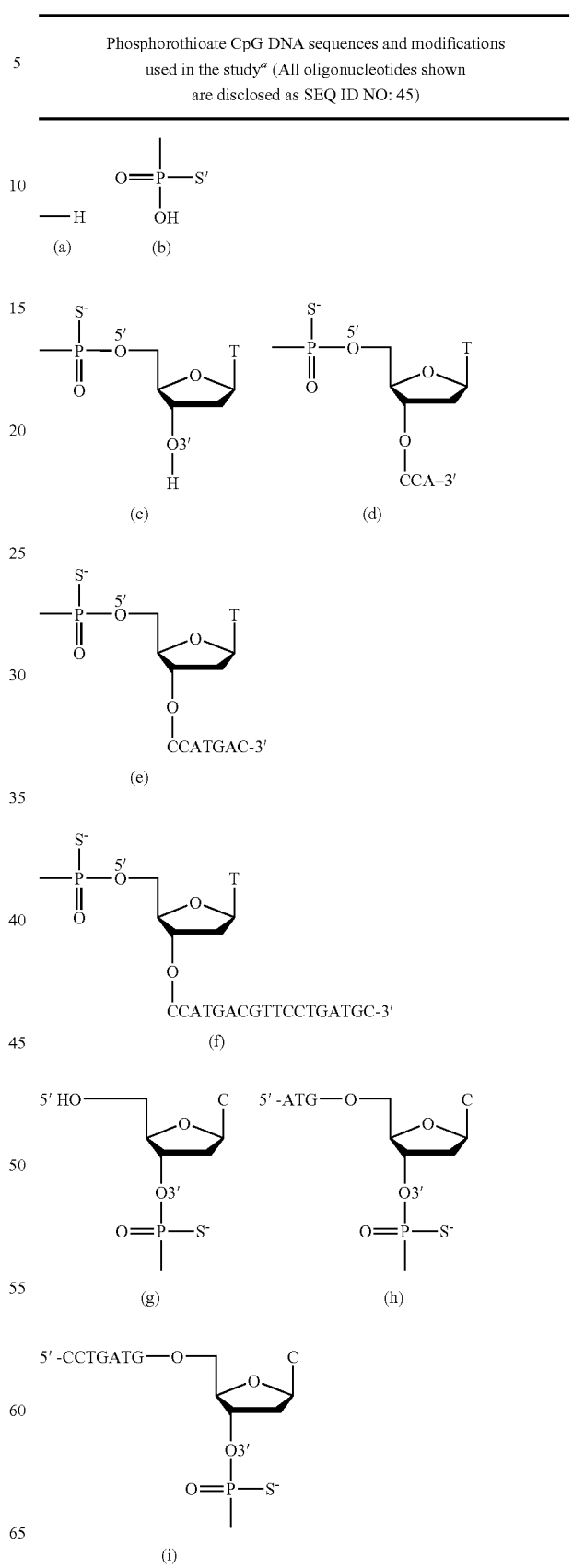

TABLE 15-continued

Phosphorothioate CpG DNA sequences and modifications used in the study[a] (All oligonucleotides shown are disclosed as SEQ ID NO: 45)

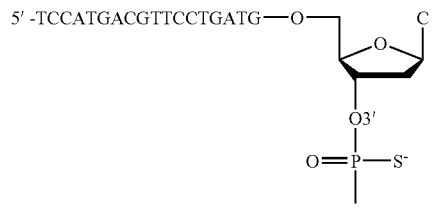

(j)

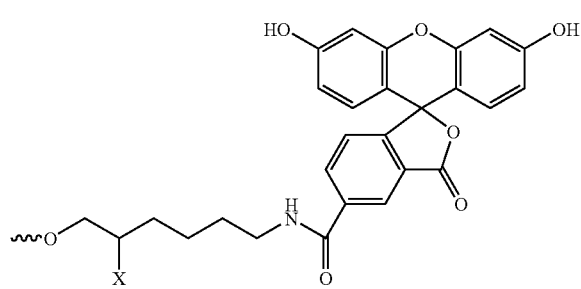

(k): X = CH$_2$OH;
(l): X = H.

Taken together, the current results suggest that an accessible 5'-end of CpG DNA is required for its optimal immunostimulatory activity and smaller groups such as a phosphorothioate, a mononucleotide, or a dinucleotide do not effectively block the accessibility of the 5'-end of CpG DNA to receptors or factors involved in the immunostimulatory pathway. However, the conjugation of molecules as large as fluorescein or larger at the 5'-end of CpG DNA could abrogate immunostimulatory activity. These results have a direct impact on the studies of immunostimulatory activity of CpG DNA-antigen/vaccine/monoclonal antibody (mAb) conjugates. The conjugation of large molecules such as vaccines or mAbs at the 5'-end of a CpG DNA could lead to suboptimal immunostimulatory activity of CpG DNA. The conjugation of functional ligands at the 3'-end of CpG DNA not only contributes to increased nuclease stability but also increased immunostimulatory potency of CpG DNA in vivo.

Example 12

Effect of Linkers on Cytokine Secretion

The following oligonucleotides were synthesized for this study. Each of these modified oligonucleotides can be incorporated into an immunomer.

TABLE 17

Sequences of CpG DNA showing the position of substitution.

| CpG DNA Number | Sequence (5'--->3')[a] |
|---|---|
| 102 | CCTACTAGCGTTCTCATC (SEQ ID NO: 49) |
| 103 | CCTACTAGC2TTCTCATC (SEQ ID NOS 80 and 81) |

TABLE 16

Induction of IL-12 and IL-6 secretion by CpG DNA-conjugates in BALB/c mice spleen cell cultures

| CpG DNA #[a] | IL-12 (pg/mL) ± SD | | | | | IL-6 (pg/mL) ± SD | | | | |
|---|---|---|---|---|---|---|---|---|---|---|
| | 0.1 µg/mL | 0.3 µg/mL | 1.0 µg/mL | 3.0 µg/mL | 10.0 µg/mL | 0.1 µg/mL | 0.3 µg/mL | 1.0 µg/mL | 3.0 µg/mL | 10.0 µg/mL |
| 89 | 991 ± 121 | 1820 ± 224 | 2391 ± 175 | 3507 ± 127 | 2615 ± 279 | 652 ± 48 | 2858 ± 180 | 13320 ± 960 | 18625 ± 1504 | 17229 ± 1750 |
| 90 | 526 ± 32 | 2100 ± 175 | 1499 ± 191 | 3019 ± 35 | 3489 ± 162 | 1387 ± 152 | 1426 ± 124 | 5420 ± 370 | 19096 ± 484 | 19381 ± 2313 |
| 91 | 1030 ± 11 | 1348 ± 102 | 2060 ± 130 | 3330 ± 130 | 3582 ± 259 | 923 ± 22 | 2542 ± 81 | 9054 ± 120 | 14114 ± 179 | 13693 ± 264 |
| 92 | 1119 ± 159 | 1726 ± 207 | 2434 ± 100 | 2966 ± 204 | 3215 ± 464 | 870 ± 146 | 1905 ± 56 | 7841 ± 350 | 17146 ± 1246 | 15713 ± 693 |
| 93 | 1175 ± 68 | 2246 ± 124 | 1812 ± 75 | 2388 ± 320 | 2545 ± 202 | 1152 ± 238 | 3499 ± 116 | 7142 ± 467 | 14064 ± 167 | 13566 ± 477 |
| 94 | 1087 ± 121 | 1705 ± 163 | 1797 ± 141 | 2522 ± 195 | 3054 ± 103 | 1039 ± 105 | 2043 ± 157 | 4848 ± 288 | 15527 ± 224 | 21021 ± 1427 |
| 95 | 1173 ± 107 | 2170 ± 155 | 2132 ± 58 | 2812 ± 203 | 3689 ± 94 | 807 ± 0.5 | 927 ± 0.5 | 3344 ± 0.5 | 10233 ± 0.5 | 9213 ± 0.5 |
| 96 | 866 ± 51 | 1564 ± 63 | 1525 ± 63 | 2666 ± 97 | 4030 ± 165 | 750 ± 63 | 1643 ± 30 | 5559 ± 415 | 11549 ± 251 | 11060 ± 651 |
| 97 | 227 ± 3 | 495 ± 96 | 1007 ± 68 | 897 ± 15 | 1355 ± 97 | 302 ± 18 | 374 ± 22 | 1000 ± 68 | 9106 ± 271 | 13077 ± 381 |
| 98 | 139 ± 18 | 211 ± 12 | 452 ± 22 | 458 ± 29 | 1178 ± 237 | 220 ± 23 | 235 ± 18 | 383 ± 35 | 1706 ± 33 | 11530 ± 254 |
| 99 | 181 ± 85 | 282 ± 105 | 846 ± 165 | 2082 ± 185 | 3185 ± 63 | 467 ± 122 | 437 ± 85 | 1697 ± 283 | 9781 ± 13 | 11213 ± 294 |
| Medium | 86 ± 6 | | | | | 60 ± 12 | | | | |

[a]See Table 1 for sequences.

TABLE 17-continued

Sequences of CpG DNA showing the position of substitution.

| CpG DNA Number | Sequence (5'--->3')[a] |
|---|---|
| 104 | CCTACT2GCGTTCTCATC (SEQ ID NOS 82 and 50) |
| 105 | CCTA2TAGCGTTCTCATC (SEQ ID NO: 83 and 51) |
| 106 | CCT22TAGCGTTCTCATC (SEQ ID NO: 84 and 51) |
| 107 | 22TACTAGCGTTCTCATC (SEQ ID NO: 52) |
| 108 | CCTACTAGCGT2CTCATC (SEQ ID NOS 53 and 85) |
| 109 | CCTACTAGCGTTC2CATC (SEQ ID NOS 54 and 86) |
| 110 | CCTACTAGCGTTC22ATC (SEQ ID NOS 54 and 87) |
| 111 | CCT6CTAGCGTTCTCATC (SEQ ID NOS 84 and 55) |
| 112 | CCTACTAGCGTTC6CATC (SEQ ID NOS 54 and 86) |
| 113 | CCT7CTAGCGTTCTCATC (SEQ ID NOS 84 and 55) |
| 114 | CCTACTAGCGTTC7CATC (SEQ ID NOS 54 and 86) |
| 4 | CTATCTGACGTTCTCTGT (SEQ ID NO: 2) |
| 115 | CTAT1TGACGTTCTCTGT (SEQ ID NOS 78 and 3) |
| 116 | CTA1CTGACGTTCTCTGT (SEQ ID NOS 79 and 8) |
| 117 | CTATCTG2CGTTCTCTGT (SEQ ID NOS 87 and 56) |
| 118 | CTATC2GACGTTCTCTGT (SEQ ID NOS 88 and 57) |
| 119 | CTA2CTGACGTTCTCTGT (SEQ ID NOS 79 and 8) |
| 120 | 22222TGACGTTCTCTGT (SEQ ID NO: 3) |
| 121 | 2222TGACGTTCTCTGT (SEQ ID NO: 3) |
| 122 | 222TGACGTTCTCTGT (SEQ ID NO: 3) |
| 123 | 22TGACGTTCTCTGT (SEQ ID NO: 3) |
| 124 | 2TGACGTTCTCTGT (SEQ ID NO: 3) |
| 125 | CTAT3TGACGTTCTCTGT (SEQ ID NOS 78 and 3) |
| 126 | CTA3CTGACGTTCTCTGT (SEQ ID NOS 79 and 8) |
| 127 | CTA33CTGACGTTCTCTGT (SEQ ID NOS 79 and 3) |
| 128 | 33TGACGTTCTCTGT (SEQ ID NO: 3) |
| 129 | CTAT4TGACGTTCTCTGT (SEQ ID NOS 78 and 3) |
| 130 | CTA4CTGACGTTCTCTGT (SEQ ID NOS 79 and 8) |
| 131 | CTA44TGACGTTCTCTGT (SEQ ID NOS 79 and 3) |
| 132 | 44TGACGTTCTCTGT (SEQ ID NO: 3) |
| 133 | CTAT5TGACGTTCTCTGT (SEQ ID NOS 78 and 3) |
| 134 | CTA5CTGACGTTCTCTGT (SEQ ID NOS 79 and 8) |
| 135 | CTA55TGACGTTCTCTGT (SEQ ID NOS 79 and 3) |
| 136 | 55TGACGTTCTCTGT (SEQ ID NO: 3) |
| 137 | CTA6CTGACGTTCTCTGT (SEQ ID NOS 79 and 8) |
| 138 | CTATCTGACGTTC6CTGT (SEQ ID NOS 58 and 89) |
| 139 | CTA7CTGACGTTCTCTGT (SEQ ID NOS 79 and 8) |
| 140 | CTATCTGACGTTC7CTGT (SEQ ID NOS 58 and 89) |
| 141 | CTATCTG8CGTTCTCTGT (SEQ ID NOS 87 and 59) |
| 142 | CTATCT8ACGTTCTCTGT (SEQ ID NOS 90 and 60) |
| 143 | CTATC8GACGTTCTCTGT (SEQ ID NOS 88 and 57) |
| 144 | CTAT8TGACGTTCTCTGT (SEQ ID NOS 78 and 3) |
| 145 | CTA8CTGACGTTCTCTGT (SEQ ID NOS 79 and 8) |
| 146 | CTATCTGACG8TCTCTGT (SEQ ID NOS 61 and 91) |
| 147 | CTATCTGACGT8CTCTGT (SEQ ID NOS 62 and 92) |
| 148 | CTATCTGACGTT8TCTGT (SEQ ID NOS 63 and 93) |
| 149 | CTATCTGACGTTC8CTGT (SEQ ID NOS 58 and 64) |
| 150 | CTATCTG9CGTTCTCTGT (SEQ ID NOS 87 and 59) |
| 151 | CTATCT9ACGTTCTCTGT (SEQ ID NOS 90 and 60) |
| 152 | CTA9CTGACGTTCTCTGT (SEQ ID NOS 79 and 8) |
| 153 | CTATCTGACGT9CTCTGT (SEQ ID NOS 62 and 92) |
| 154 | CTATCTGACGTTC9CTGT (SEQ ID NOS 58 and 64) |

Figure 14:
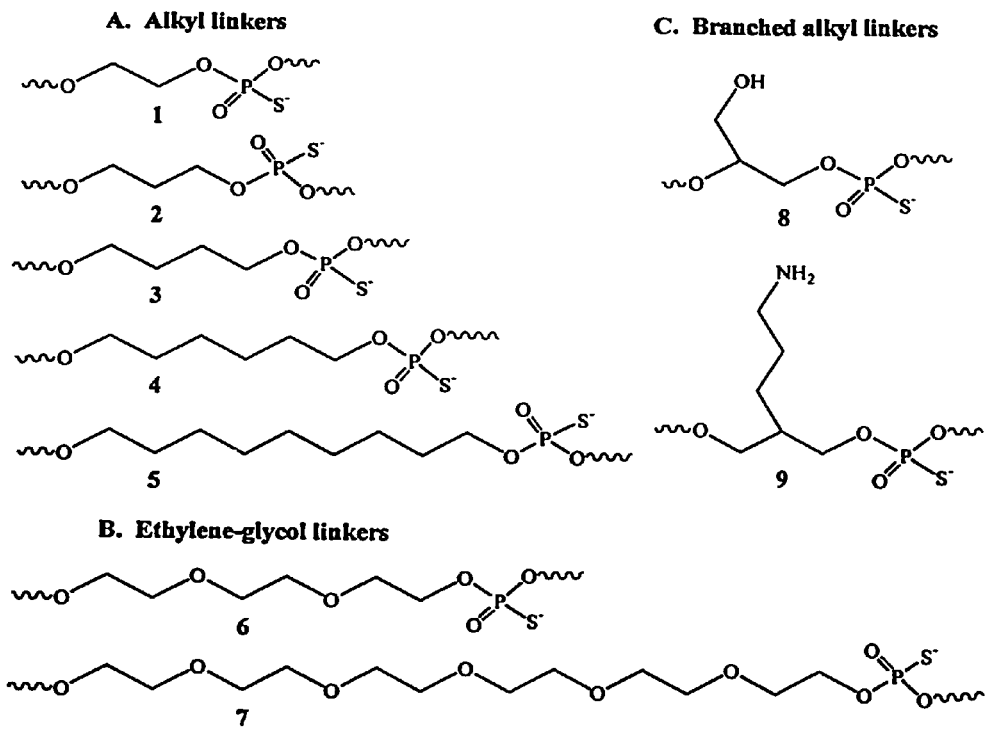
FIG. 14 shows the chemical substitutions used in Example 13.

[a]See FIG. 14 for the chemical structures of substitutions 1-9. All CpG DNAs are phosphorothioate backbone modified.

Figure 15:
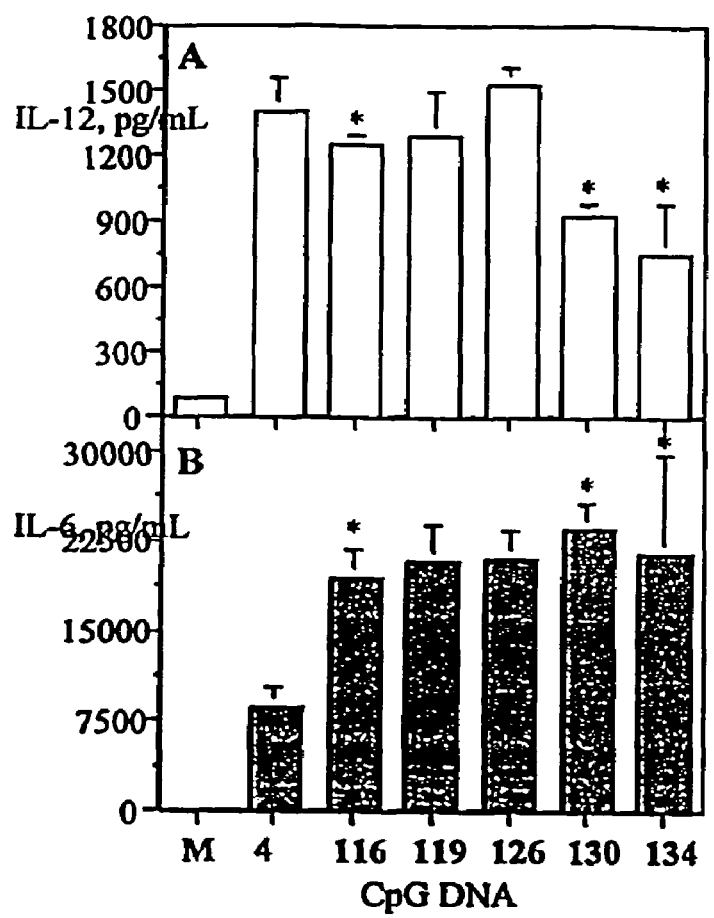
FIG. 15 shows cytokine profiles obtained using the modified oligonucleotides of Example 13.

To evaluate the optimal linker size for potentiation of immunostimulatory activity, we measured IL-12 and IL-6 secretion induced by modified CpG DNAs in BALB/c mouse spleen cell cultures. All CpG DNAs induced concentration-dependent IL-12 and IL-6 secretion. FIG. 15 shows data obtained at 1 µg/mL concentration of selected CpG DNAs, 116, 119, 126, 130, and 134, which had a linker at the fifth nucleotide position in the 5'-flanking sequence to the CpG dinucleotide compared with the parent CpG DNA. The CpG DNAs, which contained C2-(1), C3-(2), and C4-linkers (3), induced secretion of IL-12 production similar to that of the parent CpG DNA 4. The CpG DNA that contained C6 and C9-linkers (4 and 5) at the fifth nucleotide position from CpG dinucleotide in the 5'-flanking sequence induced lower levels of IL-12 secretion than did the parent CpG DNA (FIG. 15), suggesting that substitution of linkers longer than a C4-linker results in the induction of lower levels of IL-12. All five CpG DNAs, which had linkers, induced two to three times higher IL-6 secretion than did the parent CpG DNA. The presence of a linker in these CpG DNAs showed a significant effect on the induction of IL-6 compared with CpG DNAs that did not have a linker. However, we did not observe length-dependent linker effect on IL-6 secretion.

To examine the effect on immunostimulatory activity of CpG DNA containing ethylenegylcol-linkers, we synthesized CpG DNAs 137 and 138, in which a triethyleneglycol-linker (6) is incorporated at the fifth nucleotide position in the 5'- and at the fourth nucleotide position in the 3'-flanking sequences to the CpG dinucleotide, respectively. Similarly, CpG DNAs 139 and 140 contained a hexaethyleneglycol-linker (7) in the 5'- or the 3'-flanking sequence to the CpG dinucleotide, respectively. All four modified CpG DNAs (137-140) were tested in BALB/c mouse spleen cell cultures for cytokine induction (IL-12, IL-6, and IL-10) in comparison with parent CpG DNA 4. All CpG DNAs induced concentration-dependent cytokine production over the concentration range tested (0.03-10.0 µg/mL) (data not shown). The levels of cytokines induced at 0.3 µg/mL concentration of CpG DNAs 137-140 are shown in Table 18. CpG DNAs 137 and 139, which had an ethyleneglycol-linker in the 5'-flanking sequence induced higher levels of IL-12 (2106±143 and 2066±153 pg/mL) and IL-6 (2362±166 and 2507±66 pg/mL) secretion than did parent CpG DNA 4 (Table 18). At the same concentration, 137 and 139 induced slightly lower levels of IL-10 secretion than did the parent CpG DNA (Table 18). CpG DNA 138, which had a shorter ethyleneglycol-linker (6) in the 3'-flanking sequence induced IL-12 secretion similar to that of the parent CpG DNA, but significantly lower levels of IL-6 and IL-10 (Table 18). CpG DNA 140, which had a longer ethyleneglycol-linker (7) induced significantly lower levels of all three cytokines tested compared with the parent CpG DNA (Table 18).

Though triethyleneglycol-linker (6) had a chain length similar to that of C9-linker (5), the CpG DNA containing triethyleneglycol-linker had better immunostimulatory activity than did CpG DNA containing C9-linker, as determined by induction of cytokine secretion in spleen cell cultures. These results suggest that the lower immunostimulatory activity observed with CpG DNA containing longer alkyl-linkers (4 and 5) may not be related to their increased length but to their hydrophobic characteristics. This observation prompted us to examine substitution of branched alkyl-linkers containing hydrophilic functional groups on immunostimulatory activity.

TABLE 18

Cytokine secretion induced by CpG DNAs containing an ethyleneglycol-linker in BALB/c mice spleen cell cultures.

| CpG DNA Number | Cytokine, pg/mL | | |
|---|---|---|---|
| | IL-12 | IL-6 | IL-10 |
| 4 | 1887 ± 233 | 2130 ± 221 | 86 ± 14 |
| 137 | 2106 ± 143 | 2362 ± 166 | 78 ± 21 |
| 138 | 1888 ± 259 | 1082 ± 25 | 47 ± 14 |
| 139 | 2066 ± 153 | 2507 ± 66 | 73 ± 17 |
| 140 | 1318 ± 162 | 476 ± 13 | 25 ± 5 |
| Medium | 84 ± 13 | 33 ± 6 | 2 ± 1 |

To test the effect on immunostimulatory activity of CpG DNA containing branched alkyl-linkers, two branched alkyl-linkers containing a hydroxyl (8) or an amine (9) functional group were incorporated in parent CpG DNA 4 and the effects on immunostimulatory activity of the resulting modified CpG DNAs (150-154-Table 19) were examined. The data obtained with CpG DNAs 150-154, containing amino-linker 9 at different nucleotide positions, in BALB/c mouse spleen cell cultures (proliferation) and in vivo (splenomegaly) are shown in Table 19.

TABLE 19

Spleen cell proliferation induced by CpG DNA containing an aminobutyryl propanediol-linker in BALB/c mice spleen cell cultures and splenomegaly in BALB/c mice.

| CpG DNA Number[a] | Spleen cell proliferation (PI)[b] | Spleen weight (mg)[c] |
|---|---|---|
| 4 | 3.7 ± 0.8 | 121 ± 16 |
| 150 | 2.5 ± 0.6 | 107 ± 11 |
| 151 | 9.2 ± 0.7 | 169 ± 16 |
| 152 | 8.8 ± 0.4 | 220 ± 8 |
| 153 | 7.6 ± 0.7 | 127 ± 24 |
| 154 | 7.8 ± 0.04 | 177 ± 12 |
| M/V | 1.2 ± 0.3 | 102 ± 8 |
| LPS | 2.8 ± 0.5 | ND |

Parent CpG DNA 4 showed a proliferation index of 3.7±0.8 at a concentration of 0.1 µg/mL. At the same concentration, modified CpG DNAs 151-154 containing amino-linker 9 at different positions caused higher spleen cell proliferation than did the parent CpG DNA (Table 19). As observed with other linkers, when the substitution was placed adjacent to CpG dinucleotide (150), a lower proliferation index was noted compared with parent CpG DNA (Table 19), further confirming that the placement of a linker substitution adjacent to CpG dinucleotide has a detrimental effect on immunostimulatory activity. In general, substitution of an amino-linker for 2'-deoxyribonucleoside in the 5'-flanking sequence (151 and 152) resulted in higher spleen cell proliferation than found with the substitution in the 3'-flanking sequence (153 and 154). Similar results were observed in the splenomegaly assay (Table 19), confirming the results observed in spleen cell cultures. Modified CpG DNAs containing glycerol-linker (8) showed immunostimulatory activity similar to or slightly higher that that observed with modified CpG DNA containing amino-linker (9) (data not shown).

Figure 4:
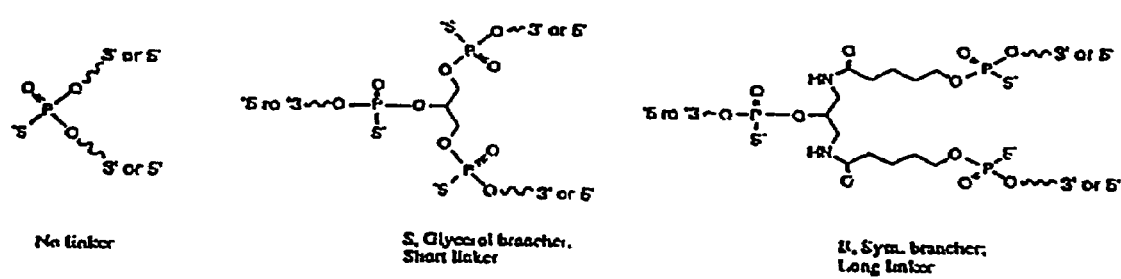
FIG. 4 depicts a group of representative small molecule linkers suitable for parallel synthesis of immunomers of the invention.
Figure 16:
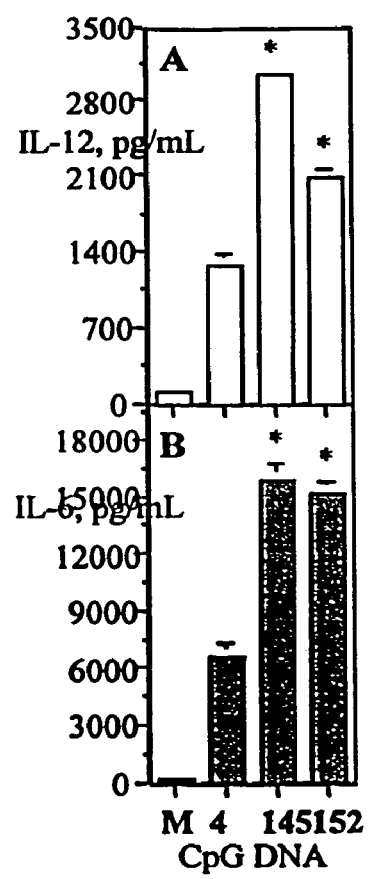
FIG. 16 shows relative cytokine induction for glycerol linkers compared with amino linkers.

In order to compare the immunostimulatory effects of CpG DNA containing linkers 8 and 9, we selected CpG DNAs 145 and 152, which had substitution in the 5'-flanking sequence and assayed their ability to induce cytokines IL-12 and IL-6 secretion in BALB/c mouse spleen cell cultures. Both CpG DNAs 145 and 152 induced concentration-dependent cytokine secretion. FIG. 4 shows the levels of IL-12 and IL-6 induced by 145 and 152 in mouse spleen cell cultures at 0.3 µg/mL concentration compared with parent CpG DNA 4. Both CpG DNAs induced higher levels of IL-12 and IL-6 than did parent CpG DNA 4. CpG DNA containing glycerol-linker (8) induced slightly higher levels of cytokines (especially IL-12) than did CpG DNA containing amino-linker (9) (FIG. 16). These results further confirm that the linkers containing hydrophilic groups are more favorable for immunostimulatory activity of CpG DNA.

We examined two different aspects of multiple linker substitutions in CpG DNA. In one set of experiments, we kept the length of nucleotide sequence to 13-mer and incorporated one to five C3-linker (2) substitutions at the 5'-end (120-124). These modified CpG DNAs permitted us to study the effect of an increase in the length of linkers without causing solubility problems. In the second set of experiments, we incorporated two of the same linker substitutions (3, 4, or 5) in adjacent positions in the 5'-flanking sequence to the CpG dinucleotide to study if there would be any additive effect on immunostimulatory activity.

Modified CpG DNAs were studied for their ability to induce cytokine production in BALB/c mouse spleen cell cultures in comparison with parent CpG DNA 4. All CpG DNAs induced concentration-dependent cytokine production. The data obtained at 1.0 µg/mL concentration of CpG DNAs is shown in Table 20. In this assay, parent CpG DNA 4 induced 967±28 pg/mL of IL-12, 1593±94 pg/mL of IL-6, and 14±6 pg/mL of IL-10 secretion at 1 µg/mL of concentration. The data presented in Table 20 suggest that as the number of linker substitutions decreased IL-12 induction decreased. However, the induction of lower levels of IL-12 secretion by CpG DNAs 123 and 124 could be the result of the shorter length of CpG DNAs. Our studies with unmodified CpG DNA shorter than 15-nucleotides showed insignificant immunostimulatory activity (data not shown). Neither length nor the number of linker substitutions have a lesser effect on IL-6 secretion. Though IL-10 secretion increased with linker substitutions, the overall IL-10 secretion by these CpG DNAs was minimal.

CpG DNAs containing two linker substitutions (linker 3-127; linker-4-131; linker-5-135) at the fourth and fifth positions in the 5'-flanking sequences to the CpG dinucleotide and the corresponding 5'-truncated versions 128, 132, and 136, respectively, were tested for their ability to induce cytokine secretion in BALB/c mouse spleen cell cultures. The levels of with parent CpG DNA 4, suggesting that the nucleobase and sugar ring at these positions are not required for receptor recognition and/or binding. The deletion of the nucleotides beyond the linker substitutions (CpG DNA 128) caused higher IL-12 and IL-6 secretion than that found with CpG DNAs 4 and 127. As expected, the substitution of two C6-linkers (4) resulted in IL-12 secretion lower than and IL-6 secretion similar to that induced by parent CpG DNA 4. The 5'-truncated CpG DNA 132 induced higher cytokine secretion than did CpG DNA 131. The CpG DNAs 135 and 136, which had two C9-linkers (5), induced insignificant cytokine secretion, confirming the results obtained with mono-substituted CpG DNA containing the same linker as described above.

Example 13

Effect of Phosphodiester Linkages on Cytokine Induction

To test the effect of phosphodiester linkages on immunomer-induced cytokine induction, the following molecules were synthesized.

TABLE 21

PO-Immunomer sequences and analytical data
(SEQ ID NOS 2, 2, 8, and 8, respectively in order of appearance)

| CpG DNA | Sequence[a] | Backbone[b] | Molecular Weight Calculated | Found[c] |
|---|---|---|---|---|
| 4 | 5'-CTATCTGACGTTCTCTGT-3' → | PS | 5702 | 5704 |
| 155 | 5'-CTATCTGACGTTCTCTGT-3' → | PO | 5432 | 5428 |
| 156 | 5'-CTGACGTTCTCTGT-X-TGTCTCTTGCAGTC-5' → ← | PO | 8656 | 8649 |
| 157 | 5'-YYCTGACGTTCTCGT-X-TGTCTCTTGCAGTCYY-5' → ← | PO | 9208 | 9214 |

[a]Arrows indicate 5'-3' directionality of CpG dinucleotide in each DNA molecule and structures of X and Y are shown in boxes.
[b]PS and PO stand for phosphorothioate and phosphodiester backbones, respectively.
[c]As determined by MALDI-TOF mass spectrometry.

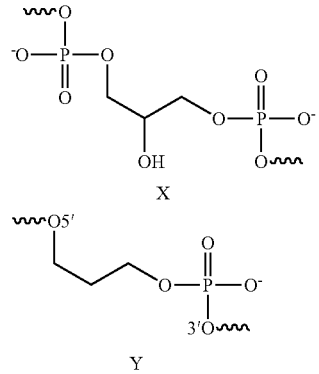

Figure 17:
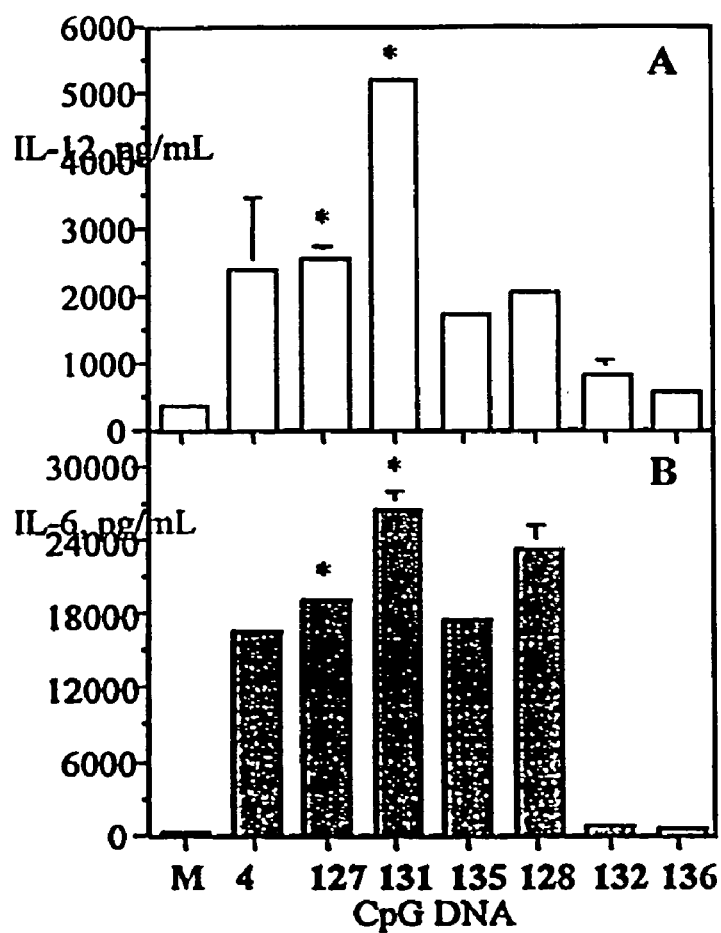
FIG. 17 shows relative cytokine induction for various linkers and linker combinations.

IL-12 and IL-6 secreted at 1.0 µg/mL concentration are shown in FIG. 17. The results presented in FIG. 17 suggest that the immunostimulatory activity is dependent on the nature of the linker incorporated. The substitution of the fourth and fifth nucleosides with C4-linker 3 (CpG DNA 127) had an insignificant effect on cytokine secretion compared PS-CpG DNA 4 (Table 21) was found to induce an immune response in mice (data not shown) with PO-CpG DNA 155 serving as a control. PO-immunomers 156 and 157 each contain two identical, truncated copies of the parent CpG DNA 155 joined through their 3'-ends via a glyceryl linker, X (Table 21). While 156 and 157 each contain the same oligonucleotide segments of 14 bases, the 5'-ends of 157 were modified by the addition of two C3-linkers, Y (Table 21). All oligonucleotides 4, 155-157 contain a 'GACGTT' hexameric motif known to activate the mouse immune system.

Figure 18:
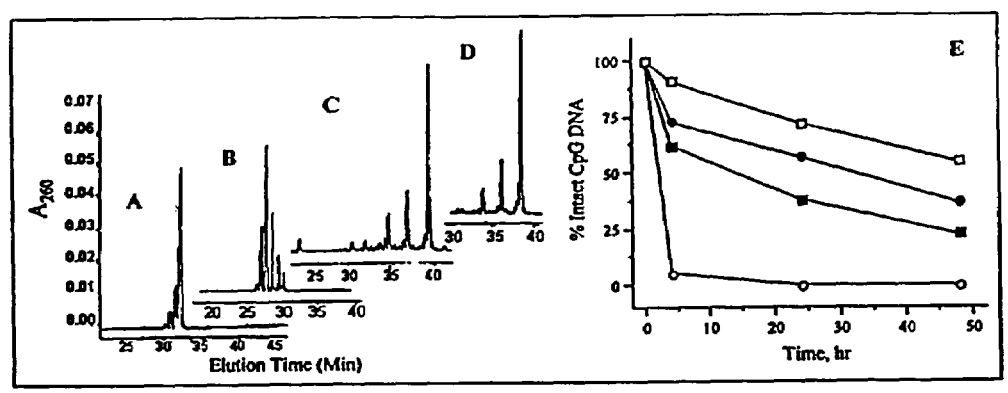
FIGS. 18A-E shows relative nuclease resistance for various PS and PO immunomers and oligonucleotides.

The stability of PO-immunomers against nucleases was assessed by incubating CpG DNAs 4, 155-157 in cell culture medium containing 10% fetal bovine serum (FBS) (non-heat-inactivated) at 37° C. for 4, 24, and 48 hr. Intact CpG DNA remaining in the reaction mixtures were then determined by CGE. FIG. 18A-D shows the nuclease digestion profiles of CpG DNAs 4, 155-157 incubated in 10% FBS for 24 hr. The amount of full-length CpG DNA remaining at each time point is shown in FIG. 18E. As expected, the parent PS-CpG DNA 4 is the most resistant to serum nucleases. About 55% of 18-mer 4 remained undegraded after 48 hr incubation. In contrast, only about 5% of full-length PO-immunomer 155 remained after 4 hr under the same experimental conditions confirming that DNA containing phosphodiester linkages undergoes rapid degradation. As expected, both PO-immunomers 156 and 157 were more resistant than 155 to serum nucleases. After 4 hr, about 62% and 73% of 156 and 157 respectively were intact compared with about 5% of 155 (FIG. 18E). Even after 48 hr, about 23% and 37% of 156 and 157, respectively, remained undegraded. As well as showing that 3'-3'-linked PO-immunomers are more stable against serum nucleases, these studies indicate that chemical modifications at the 5'-end can further increase nuclease stability.

Figure 19:
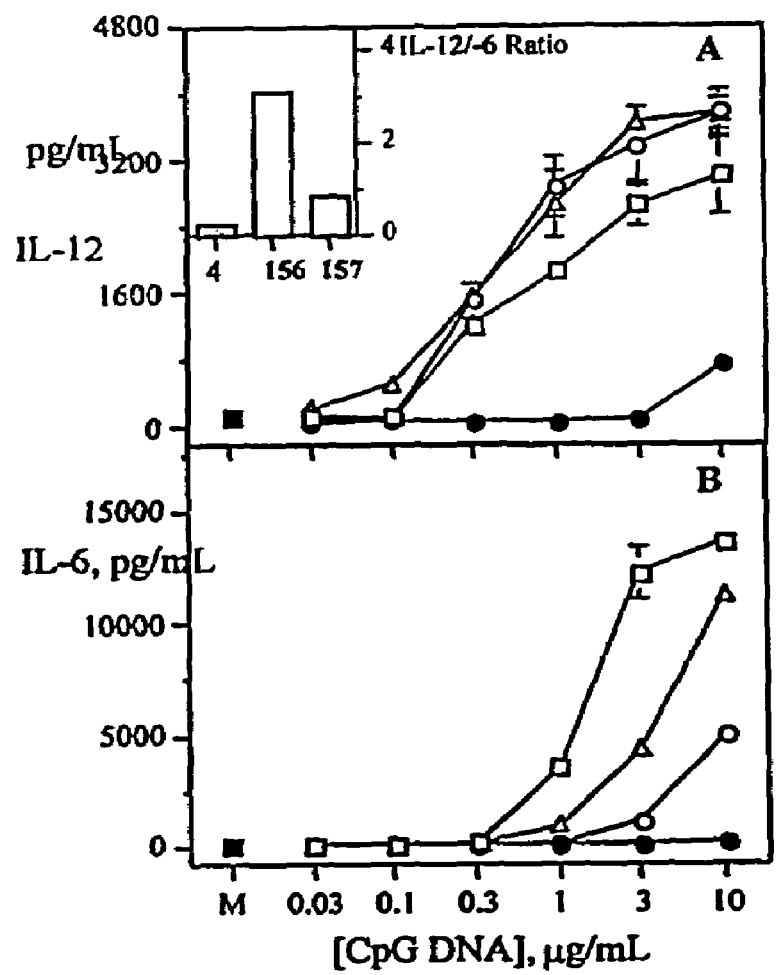
FIG. 19 shows relative cytokine induction for PO immunomers compared with PS immunomers in BALB/c mouse spleen cell cultures.

The immunostimulatory activity of CpG DNAs was studied in BALB/c and C3H/HeJ mice spleen cell cultures by measuring levels of cytokines IL-12 and IL-6 secreted. All CpG DNAs induced a concentration-dependent cytokine secretion in BALB/c mouse spleen cell cultures (FIG. 19). At 3 µg/mL, PS-CpG DNA 4 induced 2656±256 and 12234±1180 pg/mL of IL-12 and IL-6 respectively. The parent PO-CpG DNA 155 did not raise cytokine levels above background except at a concentration of 10 µg/mL. This observation is consistent with the nuclease stability assay results. In contrast, PO-immunomers 156 and 157 induced both IL-12 and IL-6 secretion in BALB/c mouse spleen cell cultures.

The results presented in FIG. 19 show a clear distinction in cytokine induction profiles of PS- and PO-CpG DNAs. PO-immunomers 156 and 157 induced higher levels of IL-12 than did PS-CpG DNA 4 in BALB/c mouse spleen cell cultures (FIG. 19A). In contrast, at concentrations up to 3 µg/mL, they produced negligible amounts of IL-6 (FIG. 19B). Even at the highest concentration (10 µg/mL), PO-immunomer 156 induced significantly less IL-6 than did PS-CpG DNA 4. The presence of C3 linkers at the 5'-terminus of PO-immunomer 157 resulted in slightly higher levels of IL-6 secretion compared with 156. However, importantly, the levels of IL-6 produced by PO-immunomer 157 are much lower than those induced by PS CpG DNA 4. The inset of FIG. 19A shows the ratio of IL-12 to IL-6 secreted at 3 µg/mL concentration. In addition to increasing IL-12 secretion, PO-immunomers 156 and 157 induced higher levels of IFN-γ than did PS-CpG DNA 4 in BALB/c mouse spleen cell cultures (data not shown).

Figure 20:
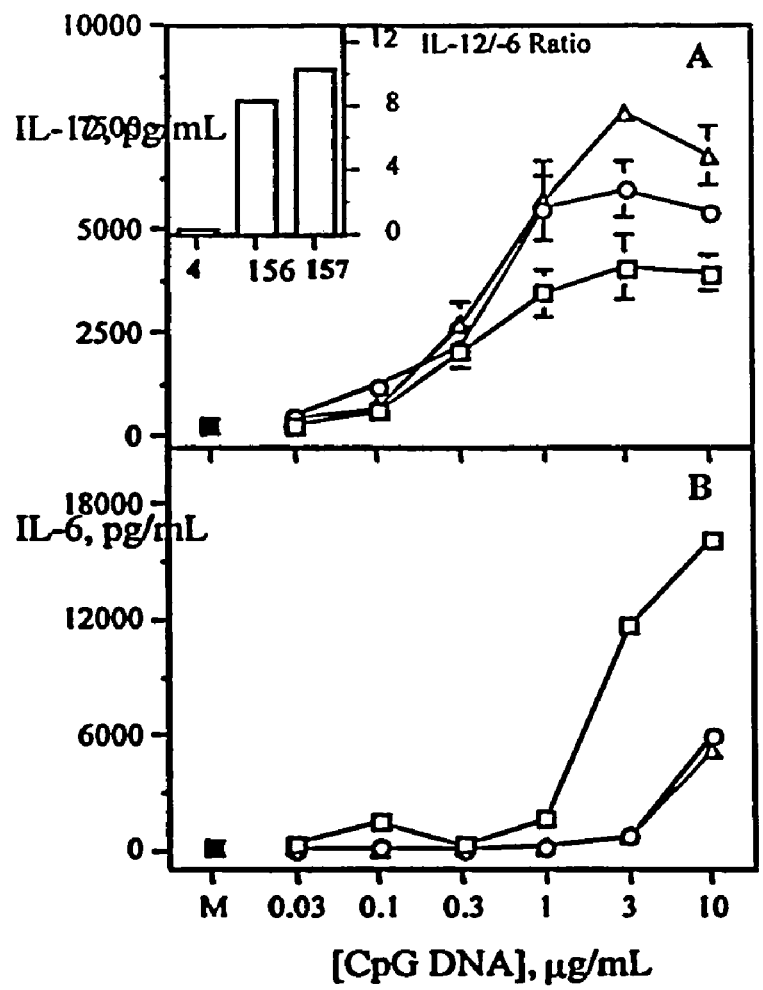
FIG. 20 shows relative cytokine induction for PO immunomers compared with PS immunomers in C3H/Hej mouse spleen cell cultures.

The different cytokine profiles induced by PO- and PS-CpG DNAs in BALB/c mouse spleen cell cultures prompted us to study the pattern of cytokine induction of CpG DNAs in C3H/HeJ mouse spleen cell cultures (an LPS lower-responsive strain). All three CpG DNAs tested in this assay induced concentration-dependent cytokine secretion (FIGS. 20A and B). Since PO-CpG DNA 155 failed to induce cytokine secretion in BALB/c mouse spleen cell cultures, it was not further tested in C3H/HeJ spleen cell cultures. Both PO-immunomers 156 and 157 induced higher IL-12 production than did PS-CpG DNA 4 (FIG. 20A). However, at concentrations up to 3 µg/mL, neither induced IL-6 production. At the highest concentration tested (10 µg/mL), both induced significantly less IL-6 than did PS-CpG DNA 4 (FIG. 20B). The ratio of IL-12 to IL-6 secreted is calculated to distinguish cytokine secretion profiles of PS and PO CpG DNAs (FIG. 20A inset). In addition, the C3H/HeJ spleen cell culture results suggest that the responses observed with CpG DNAs are not due to LPS contamination.

Figure 21:
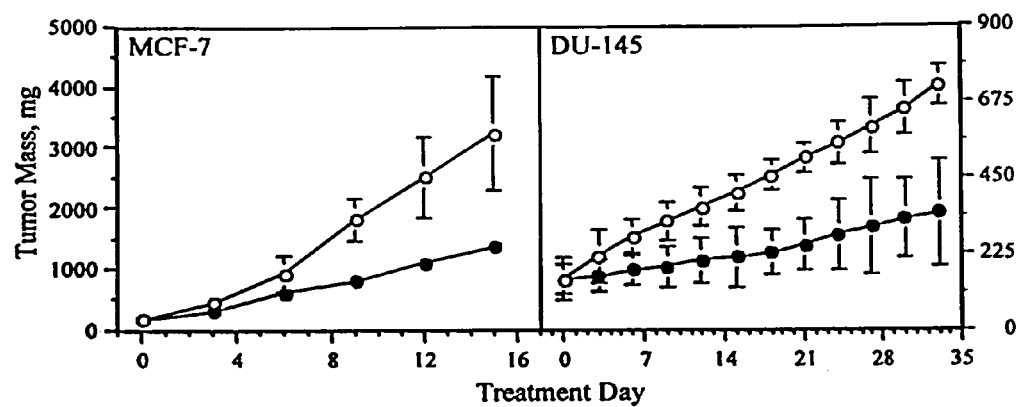
FIG. 21 shows relative cytokine induction for PO immunomers compared with PS immunomers in C3H/Hej mouse spleen cell cultures at high concentrations of immunomers.

PS-CpG DNAs have been shown to induce potent antitumor activity in vivo. Since PO-CpG DNAs exhibited greater nuclease stability and induced higher levels of IL-12 and IFN-γ secretion in in vitro assays, we were interested to see if these desirable properties of PO-immunomers improve the antitumor activity in vivo. We administered PO-immunomer 157 subcutaneously at a dose of 0.5 mg/kg every other day to nude mice bearing tumor xenografts of MCF-7 breast cancer cells that express wild-type p53, or DU-145 prostate cancer cells that express mutated p53. PO-immunomer 157 gave 57% growth inhibition of MCF-7 tumors on day 15 compared with the saline control (FIG. 21A). It also produced 52% growth inhibition of DU-145 tumors on day 34 (FIG. 21B). These antitumor studies suggest that PO-immunomers of the proposed design exhibit potent antitumor activity in vivo.

Example 14

Short Immunomers

To test the effects of short immunomers on cytokine induction, the following immunomers were used. These results show that immunomers as short as 5 nucleotides per segment are effective in inducing cytokine production.

TABLE 22

Immunomer Structure and Immunostimulatory Activity in BABL/C Mouse Spleen Cell Cultures

| Oligo No. | Sequences and Modification (5'-3') | Oligo Length/ or Each Chain | IL-12 (pg/mL) 10 µg/mL | IL-6 (pg/mL) 10 µg/mL |
|---|---|---|---|---|
| 4 SEQ ID NO: 2 | 5'-CTATCTGACGTTCTCTGT-3' | 18mer | 2731 | 4547 |
| 25 SEQ ID NO: 17 | 5'-CTATCTGTCGTTCTCTGT-3' | 18mer | 795 | 789 |
| 158 SEQ ID NO: 13 | 5'-TCTGACGTTCT-3'\\$X_1$/5'-TCTGACGTTCT-3' | 11mer | 3490 | 5319 |

TABLE 22-continued

Immunomer Structure and Immunostimulatory Activity in BABL/C Mouse Spleen Cell Cultures

| Oligo No. | Sequences and Modification (5'-3') | Oligo Length/ or Each Chain | IL-12 (pg/mL) 10 μg/mL | IL-6 (pg/mL) 10 μg/mL |
|---|---|---|---|---|
| 159 SEQ ID NO: 33 | 5'-TCTGTCGTTCT-3'<br>              \\$X_1$<br>              /<br>5'-TCTGTCGTTCT-3' | 11mer | 3265 | 4625 |
| 160 | 5'-TCGTTG-3'<br>        \\$X_1$<br>        /<br>5'-TCGTTG-3' | 6mer | 2085 | 2961 |
| 161 | 5'-TCGTTG-3'XX<br>          \\$X_1$<br>          /<br>5'-TCGTTG-3'XX | 6mer | 3169 | 5194 |
| 162 | 5'-TCGTTG-3'X<br>         \\$X_1$<br>         /<br>5'-TCGTTG-3'X | 6mer | 1015 | 705 |
| 163 | 5'-TCGTT-3'X<br>        \\$X_1$<br>        /<br>5'-TCGTT-3'X | 5mer | 2623 | 3619 |
| 164 | 5'-ACGTTG-3'X<br>         \\$X_1$<br>         /<br>5'-ACGTTG-3'X | 6mer | 564 | 845 |
| 165 | 5'-GCGTTG-3'X<br>         \\$X_1$<br>         /<br>5'-GCGTTG-3'X | 6mer | 196 | 0 |
| 166 | 5'-CCGTTG-3'X<br>         \\$X_1$<br>         /<br>5'-CCGTTG-3'X | 6mer | 219 | 0 |
| 167 | 5'-GTCGTT-3'X<br>         \\$X_1$<br>         /<br>5'-GTCGTT-3'X | 6mer | 1441 | 5056 |
| 168 | 5'-TGTCGT-3'X<br>         \\$X_1$<br>         /<br>5'-TGTCGT-3'X | 6mer | 198 | 0 |
| 169 | 5'-TCGTTG-3'X<br>         \\$X_1$—X3'-GTTGCT-5'<br>         /<br>5'-TCGTTG-3'X | 6mer | 2410 | 4857 |

Normal phase represents a phosphorothioate linkage.

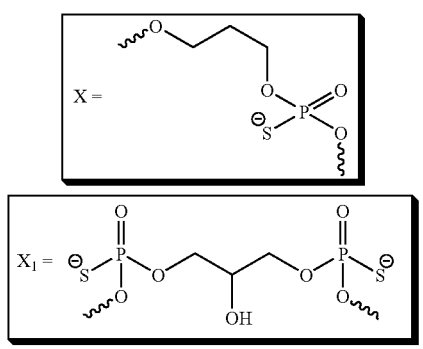

Example 15

Isolation of Human B Cells and Plasmacytoid Dendritic Cells (pDCs)

PBMCs from freshly drawn healthy volunteer blood (CBR Laboratories, Boston, Mass.) were isolated by Ficoll density gradient centrifugation method (Histopaque-1077, Sigma) and B cells were isolated from PBMCs by positive selection using the CD19 cell isolation kit (Miltenyi Biotec) according to the manufacturer's instructions.

Example 16

B Cell Proliferation Assay

A total of $1\times10^5$ B cells/200 µl were stimulated with 0.3, 1.0, 3.0, or 10.0 µg/mL concentrations of CpG DNAs for 64 hr, then pulsed with 0.75 µCi of [$^3$H]-thymidine and harvested 8 h later. The incorporation of radioactivity was measured using liquid scintillation counter. Table 23 shows an average ±SD of B cell proliferation for 6 CpG DNAs at a final concentration of 10.0 µg/mL.

TABLE 23

Immunomer Structure and Immunostimulatory Activity in Human B-Cell Proliferation Assay (72 hs)

| Oligo No. | Sequences and Modification (5'-3') | [$^3$H]-T (cpm) 10 µg/ml D1 |
|---|---|---|
| 176 SEQ ID NOS 65 and 66 | 5'-TCGTCGTT-XXX-_GUCUCGAGAC_-5' | |
| 177 SEQ ID NOS 67 and 68 | 5'-TCRTCRTT-XXX-GTCTCGAGAC-5' | |
| 178 SEQ ID NOS 65 and 68 | 5'-TCGTCGTT-XXX-GTCTCGAGAC-5' | 43962 ± 8242 |
| 179 SEQ ID NOS 69 and 70 | _5'-TCGTCGTT-XXX-GTCTCGAGAC-5'_ | 3424 ± 1923 |

TABLE 23-continued

Immunomer Structure and Immunostimulatory Activity in Human B-Cell Proliferation Assay (72 hs)

| Oligo No. | Sequences and Modification (5'-3') | [$^3$H]-T (cpm) 10 µg/ml D1 |
|---|---|---|
| 180 SEQ ID NOS 65 and 71 | 5'-TCGTCGTT-XXX-_GUCUCGAGAC_-5' | 37001 ± 4423 |

Normal phase represents a phosphorothioate linkage; Underline represents a 2'-OMe ribonucleotide; Italic phase represents a phopshodiester linkage Normal phase represents a phosphorothioate linkage; Underline represents a 2'-OMe ribonucleotide; Italic phase represents a phopshodiester Linkage.

Example 17

Human pDC Cultures and IFN-α ELISA pDCs were isolated from human PBMCs using a BDCA-4 cell isolation kit (Miltenyi Biotec) according to the manufacturer's instructions. pDC were plated in 96-well plates using $1\times10^6$ cells/mL, 200 µL/well). The CpG DNAs were added to a final concentration of 0.3, 1.0, 3.0, or 10.0 µg/mL to the cell cultures and incubated at 37° C. for 24 hr. Supernatants were then harvested and assayed for IFN-α using the human IFN-α ELISA kit (PBL). Tables 24A-24C shows an average ±SD of IFN-α for 6 CpG DNAs at a concentrations of 1.0 and 10.0 µg/mL.

TABLE 24A

Immunomer Structure and Immunostimulatory Activity in Human Dendritic Cell Assay (72 hs)

| Oligo No. | Sequences and Modification (5'-3') | IFN-α (pg/ml) 10 µg/ml D1 | IFN-α (pg/ml) 10 µg/ml D2 | IFN-α (pg/ml) 10 µg/ml D3 |
|---|---|---|---|---|
| 176 SEQ ID NOS 65 and 66 | 5'-TCGTCGTT-XXX-_GUCUCGAGAC_-5' | 6234 ± 20 | | |
| 177 SEQ ID NOS 67 and 68 | 5'-TCRTCRTT-XXX-GTCTCGAGAC-5' | 6976 ± 251 | | |
| 178 SEQ ID NOS 65 and 68 | 5'-TCGTCGTT-XXX-GTCTCGAGAC-5' | 14735 ± 645 | 2747 ± 17 | |
| 179 SEQ ID NOS 69 and 70 | _5'-TCGTCGTT-XXX-GTCTCGAGAC-5'_ | 0 ± 0 | | |
| 180 SEQ ID NOS 65 and 71 | 5'-TCGTCGTT-XXX-_GUCUCGAGAC_-5' | 2757 ± 88 | | |

TABLE 24B

Immunomer Structure and Immunostimulatory Activity in Human Dendritic Cell Assay (24 hs)

| Oligo No. | Sequences and Modification (5'-3') | IFN-α (pg/ml) 1 µg/ml D1 | IFN-α (pg/ml) 1 µg/ml D2 | IFN-α (pg/ml) 1 µg/ml D3 |
|---|---|---|---|---|
| 181<br>SEQ ID NO: 72 | 5'-TCRTCRTTG-3'\<br>　　　　　　　$X_1$<br>5'-TCRTCRTTG-3'/ | 17124 ± 210 | 4870 ± 73 | 526 ± 12 |
| 182<br>SEQ ID NO: 73 | 5'-TCR$_1$TCR$_1$TTG-3'\<br>　　　　　　　$X_1$<br>5'-TCR$_1$TCR$_1$TTG-3'/ | 15359 ± 132 | 6668 ± 214 | 839 ± 0 |
| 183<br>SEQ ID NO: 74 | 5'-TTGTGCTTG-3'\<br>　　　　　　　$X_1$<br>5'-TTGTGCTTG-3'/ | 60 ± 0 | 60 ± 0 | 0 ± 0 |
| 184<br>SEQ ID NO: 75 | 5'-TCGTCGTTG-3'\<br>　　　　　　　$X_1$<br>5'-TCGTCGTTG-3'/ | 37111 ± 0 | 34540 ± 302 | 1313 ± 34 |
| Media | | 20 ± 0 | 20 ± 0 | 0 ± 0 |

TABLE 24C

Immunomer Structure and Immunostimulatory Activity in Human Dendritic Cell Assay (24 hs)

| Oligo No. | Sequences and Modification (5'-3') | IFN-α (pg/ml) 1 µg/ml D4 | IFN-β (pg/ml) 1 µg/ml D5 | IFN-α (pg/ml) 10 µg/ml D6 |
|---|---|---|---|---|
| 181<br>SEQ ID NO: 72 | 5'-TCRTCRTTG-3'\<br>　　　　　　　$X_1$<br>5'-TCRTCRTTG-3'/ | 11326 ± 23 | 2220 ± 493 | 3226 ± 519 |
| 182<br>SEQ ID NO: 73 | 5'-TCR$_1$TCR$_1$TTG-3'\<br>　　　　　　　$X_1$<br>5'-TCR$_1$TCR$_1$TTG-3'/ | 4560 ± 72 | 3190 ± 681 | |
| 183<br>SEQ ID NO: 74 | 5'-TTGTGCTTG-3'\<br>　　　　　　　$X_1$<br>5'-TTGTGCTTG-3'/ | 0 ± 0 | 462 ± 64 | 20 ± 3 |
| 184<br>SEQ ID NO: 75 | 5'-TCGTCGTTG-3'\<br>　　　　　　　$X_1$<br>5'-TCGTCGTTG-3'/ | 11629 ± 120 | | 183 ± 35 |
| Media | | 0 ± 0 | nd | 24 ± 3 |

Example 18

Human peripheral blood mononuclear cells (PBMCs) were isolated from peripheral blood of healthy volunteers and prepared as discussed above in Example 4. Tables 25A-25C shows an average ±SD of IL-6, IL-12 and IL-γ for 5 IMO compounds at a concentrations of 10.0 µg/mL.

TABLE 25A

Immunomer Structure and Immunostimulatory Activity in Human PBMC Assay (72 hs)

| Oligo No. | Sequences and Modification (5'-3') | IL-6 (pg/ml) 10 µg/ml D1 | IL-12 (pg/ml) 10 µg/ml D1 | IFN-γ (pg/ml) 10 µg/ml D1 |
|---|---|---|---|---|
| 176 SEQ ID NOS 65 and 66 | 5'-TCGTCGTT-XXX-<u>GUCUCGAGAC</u>-5' | | | |
| 177 SEQ ID NOS 67 and 68 | 5'-TCRTCRTT-XXX-GTCTCGAGAC-5' | | | |
| 178 SEQ ID NOS 65 and 68 | 5'-TCGTCGTT-XXX-GTCTCGAGAC-5' | 11429 ± 38 | 1310 ± 2 | 887 ± 35 |
| 179 SEQ ID NOS 69 and 70 | *5'-TCGTCGTT-XXX-GTCTCGAGAC-5'* | | | |
| 180 SEQ ID NOS 65 and 71 | 5'-TCGTCGTT-XXX-<u>GUCUCGAGAC</u>-5' | 6281 ± 317 | 439 ± 11 | 642 ± 6 |

TABLE 25B

Immunomer Structure and Immunostimulatory Activity in Human PBMC Assay (24 hs)

| Oligo No. | Sequences and Modification (5'-3') | IFN-γ (pg/ml) 10 µg/ml D7 | IL-6 (pg/ml) 10 µg/ml D7 |
|---|---|---|---|
| 181 SEQ ID NO: 72 | 5'-TCRTCRTTG-3' \ $X_1$ / 5'-TCRTCRTTG-3' | 287 ± 38 | 24383 ± 57 |
| 182 SEQ ID NO: 73 | 5'-TC$R_1$TC$R_1$TTG-3' \ $X_1$ / 5'-TC$R_1$TC$R_1$TTG-3' | 485 ± 7 | 14220 ± 1663 |
| 183 SEQ ID NO: 74 | 5'-TTGTGCTTG-3' \ $X_1$ / 5'-TTGTGCTTG-3' | 484 ± 53 | 642 ± 4 |
| 184 SEQ ID NO: 75 | 5'-TCGTCGTTG-3' \ $X_1$ / 5'-TCGTCGTTG-3' | 817 ± 62 | 8451 ± 437 |
| Media | | 146 ± 30 | 150 ± 3 |

TABLE 25C

Immunomer Structure and Immunostimulatory Activity in Human PBMC Assay (24 hs)

| Oligo No. | Sequences and Modification (5'-3') | IL-12 (pg/ml) 10 µg/ml D8 | IL-6 (pg/ml) 10 µg/ml D8 |
|---|---|---|---|
| 181 SEQ ID NO: 72 | 5'-TCRTCRTTG-3' \ $X_1$ / 5'-TCRTCRTTG-3' | 90 ± 4 | 24853 ± 671 |
| 182 SEQ ID NO: 73 | 5'-TC$R_1$TC$R_1$TTG-3' \ $X_1$ / 5'-TC$R_1$TC$R_1$TTG-3' | 347 ± 2 | 24218 ± 397 |
| 183 SEQ ID NO: 74 | 5'-TTGTGCTTG-3' \ $X_1$ / 5'-TTGTGCTTG-3' | 286 ± 53 | 15903 ± 476 |
| 184 SEQ ID NO: 75 | 5'-TCGTCGTTG-3' \ $X_1$ / 5'-TCGTCGTTG-3' | 345 ± 22 | 25562 ± 746 |
| Media | | 70 ± 20 | 2585 ± 272 |

Soley for the purposes of Tables 23, 24A-24C and 25A-25C: Normal phase represents a phosphorothioate linkage; Underline represents a 2'-OMe ribonucleotide; Italic phase represents a phopshodiester linkage and R, $R_1$, X and $X_1$ are defined as follows:

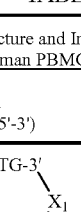

R =  dG$^{7\text{-deaza}}$

-continued

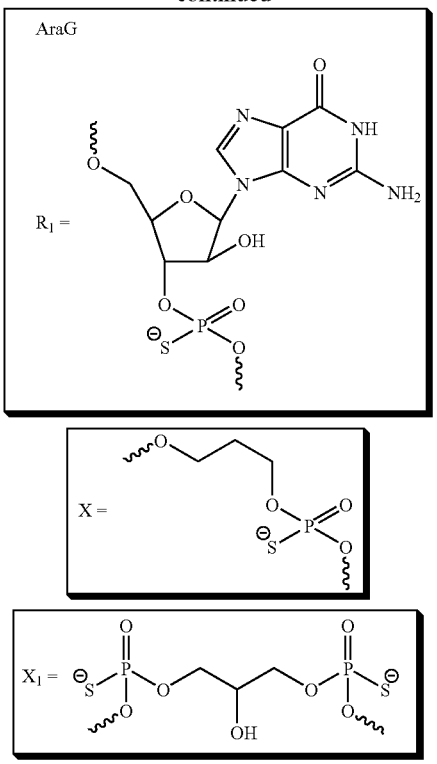

Example 19

Spleen Cell Studies

Female BALB/c mice, 5-6 weeks old, were obtained from Taconic Farms (Germantown, N.Y.) and maintained on an OVA-free diet. Groups of five mice were used in the immunization study. IMO compounds (FIG. 22) were synthesized, purified, and analyzed as described above.

Figure 2:
FIG. 2 depicts several representative immunomers of the invention (All oligonucleotides shown are disclosed as SEQ ID NO: 2).
Figure 3:
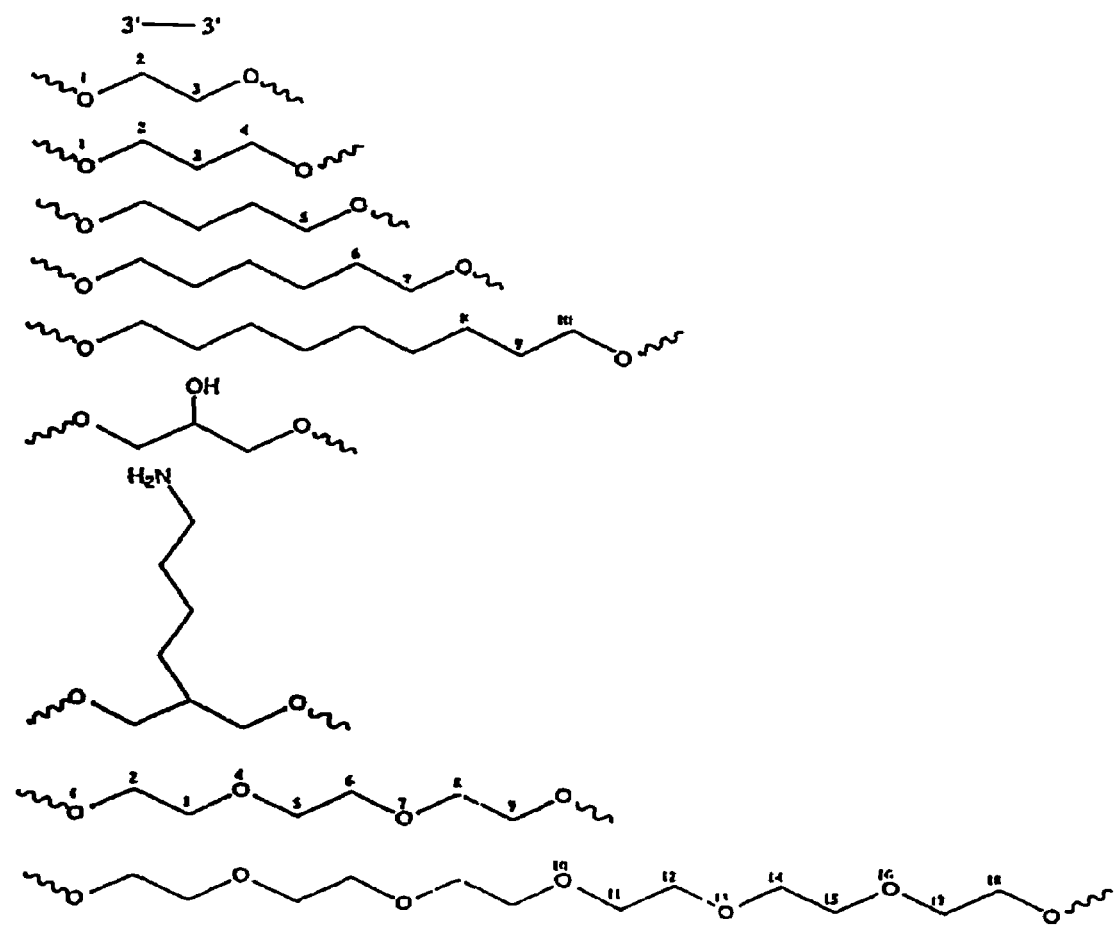
FIG. 3 depicts a group of representative small molecule linkers suitable for linear synthesis of immumomers of the invention.

Each mouse was sensitized by subcutaneous (s.c.) injection of 10-μg chicken ovalbumin (OVA; grade V, Sigma, St. Louis, Mo.) in 100-μl PBS mixed with an equal volume of alum solution (Imject-Alum, Pierce, Rockford, Ill.) on days 0 and 14 and challenged intranasally (i.n.) with 20-μg OVA in 40-μl PBS on days 28, 29, and 30 (FIG. 2). IMOs 1 and 2 (30 or 60 μg) dissolved in 200 μl PBS was injected s.c. to mice on days 33, 37, 40 and 43. Blood samples from mice under anesthesia were collected 2 h after the first injection of an IMO compound on day 33 by retro-orbital puncture and serum was harvested for cytokine assays. Each mouse was challenged i.n. with 10-μg OVA in 40-μl PBS on day 44. Mice were bled and the lungs and spleens were removed 24 h after the last OVA challenge.

Single spleen-cell suspensions were prepared in cold RPMI 1640 medium (Sigma) and pooled for each experimental group at 5×10$^6$ cells/ml in RPMI 1640 medium containing 10% FCS (HyClone, Logan, Utah) and 100-1 g/ml penicillin and 100-U/ml streptomycin (HyClone). Spleen cells (0.2 ml/well) were incubated in 96-well flat-bottom culture plates (Costar, Cambridge, Mass.) in the presence of 100-μg/ml OVA at 37° C. in a 5% $CO_2$ atmosphere. Following a 72-h incubation, culture supernatants were harvested for cytokine assays.

Levels of IL-5, IL-10, IL-12, and IFN-γ were determined by enzyme-linked immunosorbent assay (ELISA) with mouse antibodies from BD Biosciences (San Diego, Calif.). IL-6 and IL-13 levels were assessed with mouse DuoSet ELISA kits (R & D System, Minneapolis, Minn.) following the manufacturer's instructions.

Figure 24A:
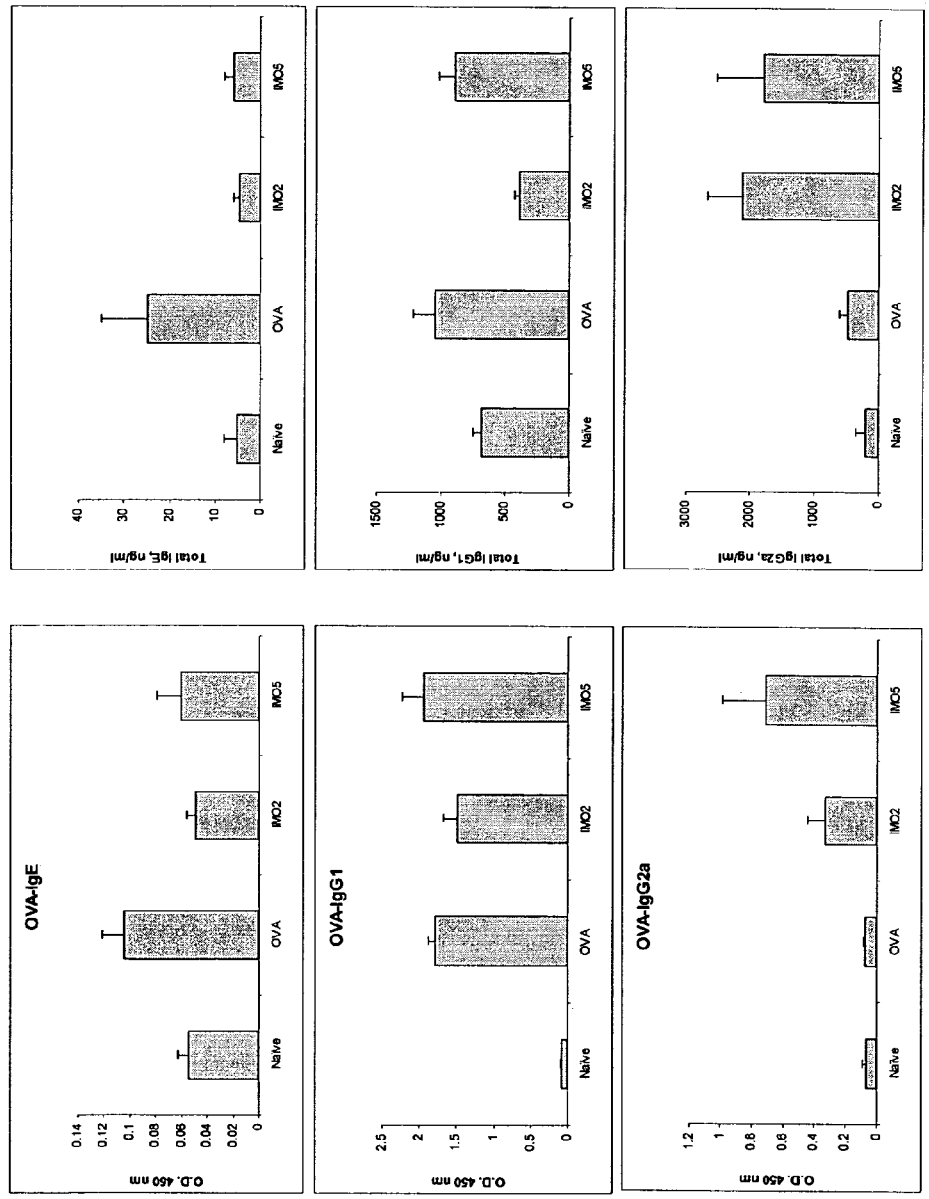
FIGS. 24A and 24B show IMO prevention of OVA-induced Th2 immune response in mice as demonstrated by serum antibody responses.
Figure 24B:
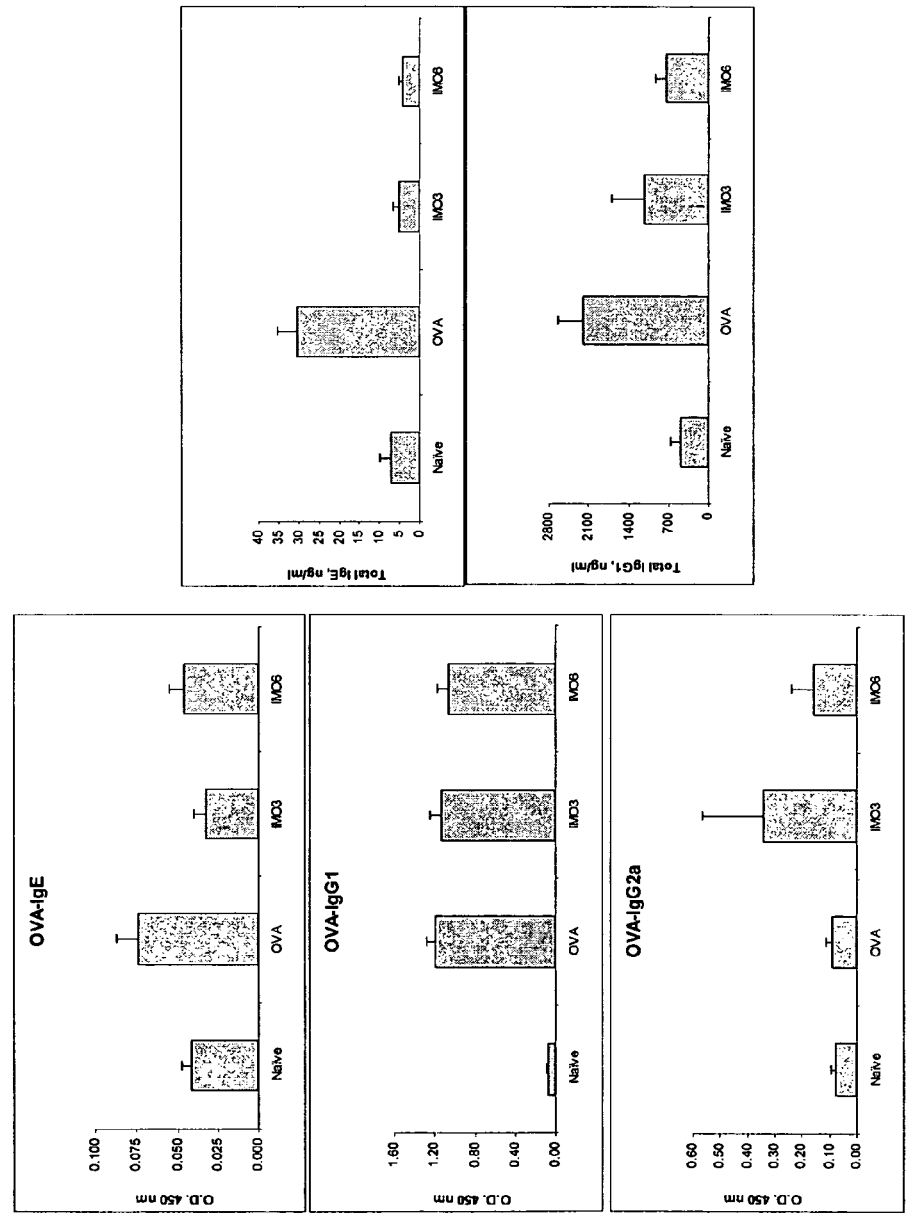

Levels of OVA-specific and total IgE and IgG2a were evaluated in mouse serum by ELISA. For OVA-specific Ig detection, 96-well ELISA plates (Immulon 2; Dynatech, Chantilly, Va.) were coated with 10-μg/ml OVA in PBS, pH 9.6. For total Ig detection, the plates were coated with 1-μg/ml anti-mouse IgE (clone R35-72) and 1-μg/ml anti-mouse IgG2a (clone R11-89). After incubation at 4° C. overnight, the plates were blocked with 1% BSA/PBS, pH 7.4, at room temperature for 1 h. Serial dilutions of serum (1:10 for IgE, 1:100 for IgG2a) was added to the plates and incubated at room temperature for 2 h. The plates were washed and 100 μl/well of biotinylated anti-mouse IgE (clone R35-116) at 0.25 μg/ml, or IgG2a (clone R19-15) at 0.25 μg/ml was added to plates and incubated at room temperature for 2 h. All antibodies were obtained from BD Biosciences. Plates were washed and 100 μl/well of 0.25 μg/ml streptavidin-peroxidase (Sigma) was added for 1-h incubation at room temperature. Assays were developed in 100 μl/well of TMB Substrate Solution (KPL, Gaithersburg, Md.) followed by 100 μl/well of Stop Solution (KPL). $A_{450}$ (same as OD450?) was measured using a microplate reader (Bio-Tek Instruments, Inc. Winooski, Vt.), and the data were analyzed with KC Junior software (High Point, N.C.). (see FIG. 24)

Example 20

Lung Histology

The lungs removed on day 45 were fixed in neutral formalin and sent to Mass Histology Service (Warwick, R.I.) for processing and hematoxylin & eosin (HE) and periodic acid Schiff (PAS) staining. The lung tissue sections were observed under a light microscope and photographed with a digital camera.

Statistical analysis was performed using analysis of variance (ANOVA). OVA-immunized and IMO-treated groups were compared using Student's t-test. Results were expressed as the mean±SEM. All comparisons were two tailed and the statistical significances were shown as *p<0.05.

Example 21

Study in Prevention Model

The ability of IMO compounds to prevent OVA-induced allergic inflammation in mice was examined. Each mouse was sensitized by subcutaneous (s.c.) injection of 20-μg chicken ovalbumin (OVA; grade V, Sigma, St. Louis, Mo.) in 100-μl PBS mixed with an equal volume of alum solution (Imject-Alum, Pierce, Rockford, Ill.) on days 0, 7 and 14. The naive group of mice received alum injection only. IMO compounds (10 μg) dissolved in the OVA/alum mixture were administered to mice on days 0, 7 and 14. Fourteen days after the last immunization, mice under anesthesia with isoflurane (Abbott Laboratories, North Chicago, Ill.) were bled by retro-orbital puncture and then sacrificed to remove the spleens.

Example 22

Effect of IMO Compounds on the Inhibition of Th2 Cytokines, IL-4, IL-5, IL-12 and IL-13 in Antigen-Specific Recall Immune Response To determine the ability of IMO compounds to alter the Th2-dominant immune response in mice injected with OVA/alum, IMO compounds along with OVA/alum were injected on days 0 and 14. The spleen cells were isolated from mice on day 28 and incubated with OVA for 72 hrs (antigen recall). Spleen cells from mice injected with OVA/alum only produced higher levels of Th2-associated cytokines, such as IL-4 (~2-fold), IL-5 (130-fold), and IL-13 (28-fold), than did naïve mice (see FIGS. 23A and 23B). Spleen cells from mice that received CpG DNA or IMO compounds and OVA secreted significantly less of these cytokines, particularly IL-5 and IL-13; IL-5 was decreased by 20% to 97% and IL-13 was decreased by 60% to 95%. These results suggest that IMO compounds have an inhibitory effect on Th2-associated cytokine secretion.

Example 23

Figure 23A:
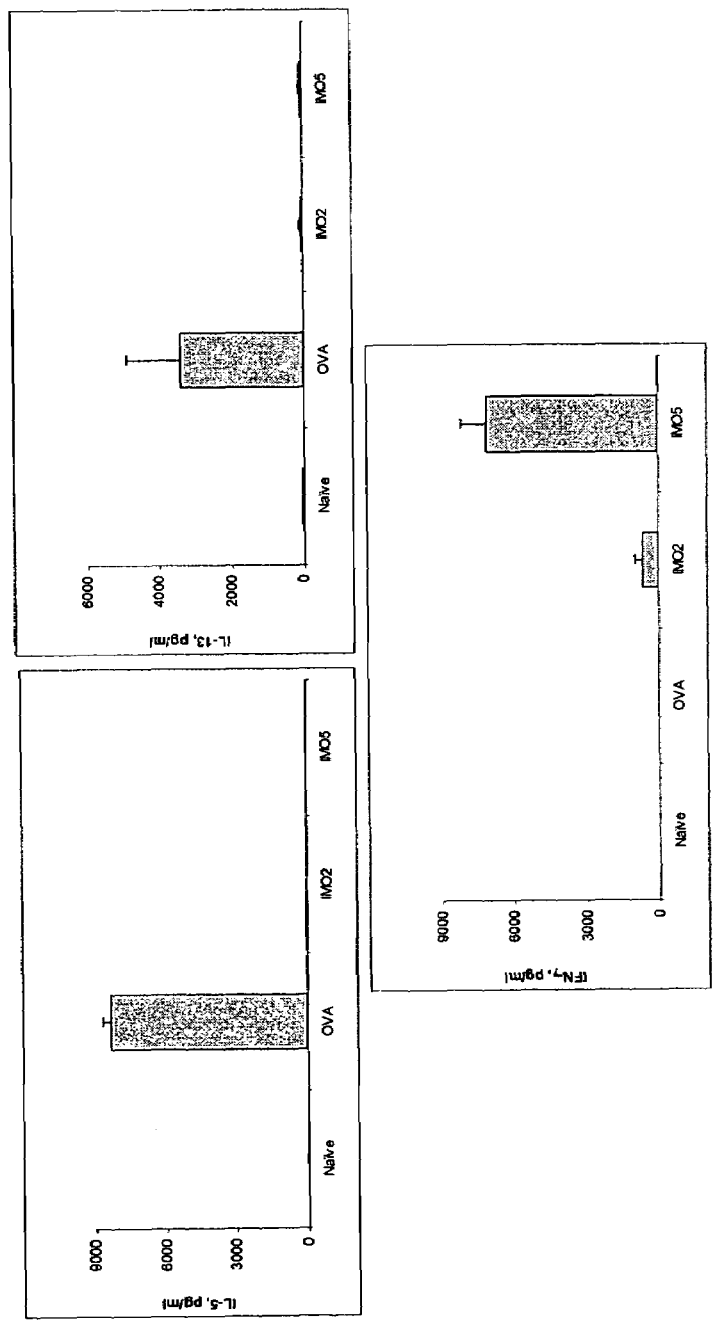
FIGS. 23A and 23B show IMO prevention of OVA-induced Th2 immune response in mice as demonstrated by cytokine responses in spleen cell cultures.
Figure 23B:
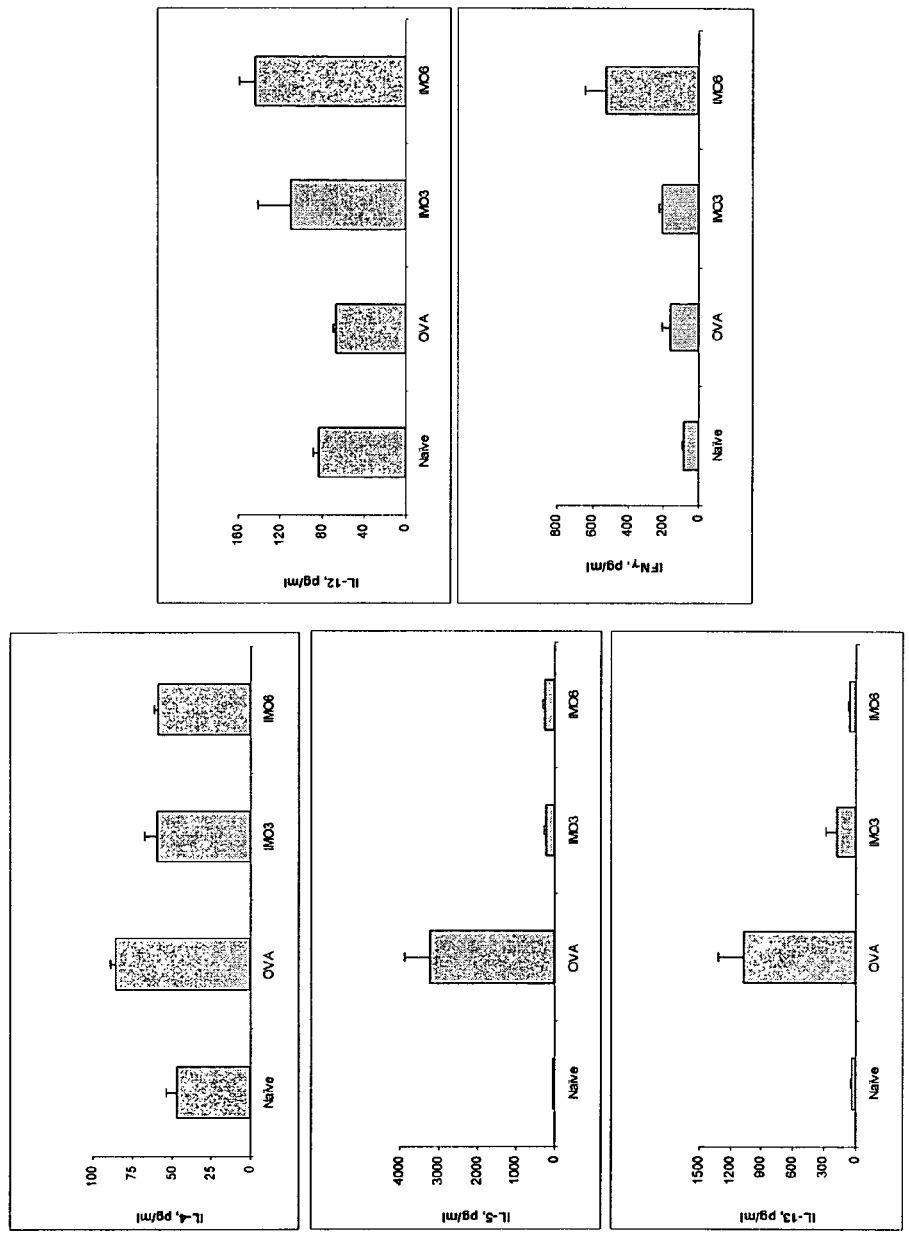

Effect of IMO Compounds on IFN-γ Production in Antigen-Specific Recall Immune Response In the same antigen-recall experiments, significantly higher levels of the Th1 cytokine IFN-γ were produced by spleen cells from mice injected with OVA/alum and IMO compounds than by cells from naïve or OVA/alum-injected mice (see FIGS. 23A and 23B). Spleen cells from mice injected with OVA/alum and conventional CpG DNA I produced levels of IFN-γ comparable to those produced by naive spleen cells. These results demonstrate that treatment of OVA/alum-injected mice with IMO compounds can change the immune response from Th2-dominant to predominantly Th1 type, as reflected by the cytokines produced by spleen cells.

Example 24

The Effect of IMO Compounds on OVA-Specific and Total IgE Production

To assess the effects of IMO compounds on IgE production, serum levels of OVA-specific and total IgE 14 days after the last OVA/alum injection were examined. Sensitization with OVA/alum resulted in high levels of OVA-specific IgE production in mice; levels of OVA-specific IgE levels were significantly lower (comparable to those found in naïve mice) in mice that received IMO compounds along with OVA/alum (see FIGS. 24A and 24B). Total serum IgE levels were also low in mice injected with OVA/alum and IMO compounds.

Example 25

Effect of IMO Compounds on OVA-Specific and Total IgG1 and IgG2a Production To assess the effects of IMO compounds on IgG1 and IgG2a production, serum levels of OVA-specific and total IgG1 and IgG2a were examined. Animals that received injections of OVA/alum produced high levels of OVA-specific IgG1 and insignificant levels of OVA-specific IgG2a (see FIGS. 24A and 24B). Injection of IMO compounds to mice either had no effect or reduced the levels of OVA-specific IgG1 compared with levels found in OVA/alum-injected mice. OVA-specific IgG2a antibody levels were significantly higher in the serum of mice who received IMO compounds than in those who received only OVA/alum. These IgG1 and IgG2a levels translated into higher ratios of OVA-specific IgG2a/IgG1 in mice injected with OVA/alum plus IMO compounds than in mice who received only OVA/alum.

Similar results were found for serum total Ig production. Serum from mice injected with OVA/alum and IMO compounds had lower levels of total IgG1 and higher levels of total IgG2a than did mice that received OVA/alum only.

Example 26

Study in Therapeutic Model

The therapeutic potential of IMOs 1 and 2 were tested in a mouse model of asthma. Mice were sensitized and challenged with OVA and treated with IMOs 1 and 2 as described in the protocol above.

To determine the effects of IMOs 1 and 2 treatment on the local immune response, the histology of the lungs of naive and OVA/alum-sensitized-and-challenged mice with or without IMOs 1 and 2 treatment was examined 48 hours after the last injection of IMOs 1 and 2. OVA-sensitized and challenged mice that were not treated with IMOs 1 and 2 showed severe inflammatory cell infiltration and airway epithelial hyperplasia compared with naive mice (data not shown). On the contrary, IMOs 1 and 2-treated mice had less inflammatory cell infiltration and less airway hyperplasia than did untreated mice (data not shown). These results demonstrate the ability of IMOs 1 and 2 to reverse OVA-induced lung inflammation in mice sensitized and challenged with OVA.

Example 27

Figure 25:
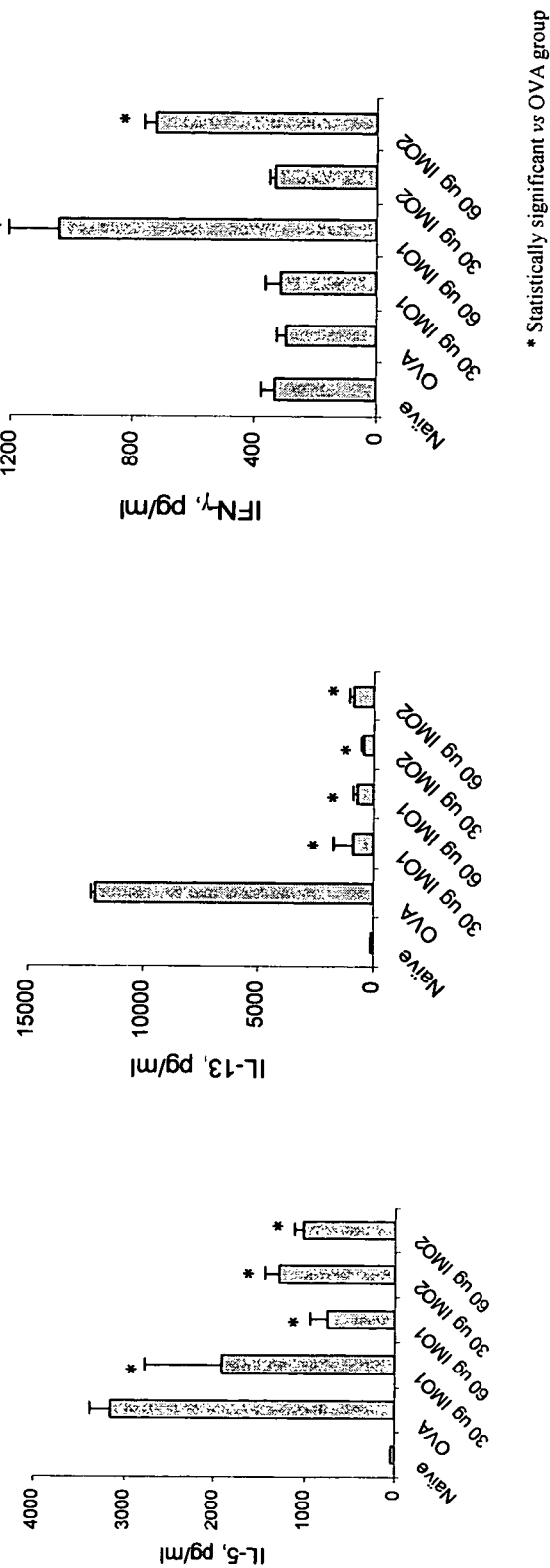
FIG. 25 shows dose-dependent effects of IMOs 1 and 2 on established OVA-induced allergic asthma in mice. Cytokine secretion is in spleen cell cultures in OVA-recall response. Both IMOs 1 and 2 significantly inhibited IL-5 secretion in a dose-dependent fashion. IL-13 was significantly inhibited by both IMO compounds. Both IMO compounds induced dose-dependent IFN-g secretion.

Effect of IMOs 1 and 2 Treatment on Th2 and Th1 Cytokines in Antigen-Specific Recall Immune Response To determine the ability of IMOs 1 and 2 to reverse Th2-dominant immune responses in mice sensitized and challenged with OVA, we isolated spleen cells from mice on day 45 and incubated them with OVA for 72 hr. After re-stimulation of spleen cells with OVA, we observed marked differences in the production of Th2 cytokines (IL-5, and IL-13) among the treatment groups. Spleen cells from mice injected with OVA only produced high levels of Th2-associated cytokines (FIG. 25). Mice treated with IMOs 1 and 2 produced significantly less of the OVA-induced Th2 cytokines (FIG. 25). In the antigen-recall experiments, only low levels of IL-12 and IFN-γ were induced in cultures of spleen cells from naïve and OVA/alum-sensitized-and-challenged mice. Spleen cells from mice treated with IMOs 1 and 2 following the OVA challenge produced significantly higher levels of IFN-γ (FIG. 25).

Example 28

Figure 26:
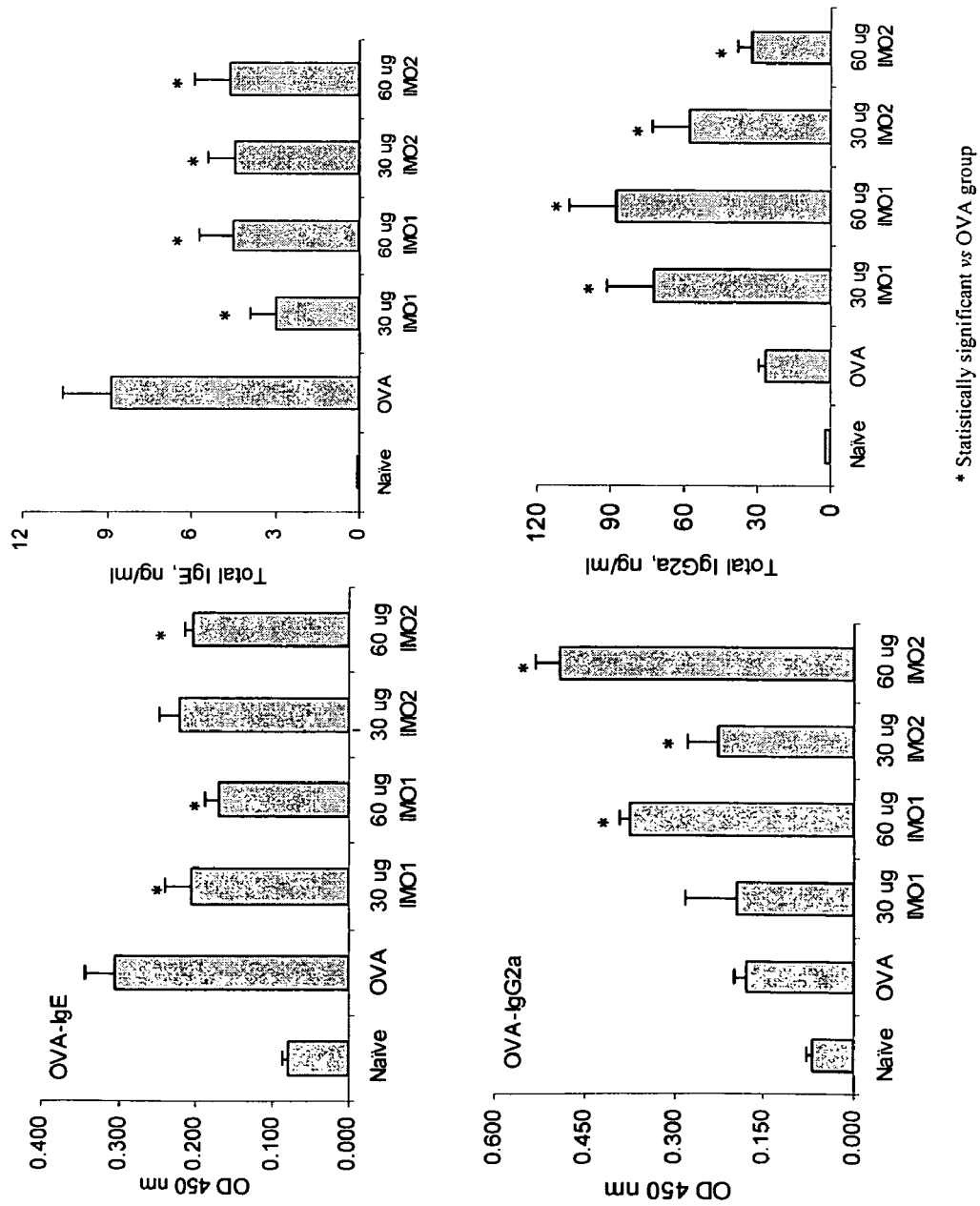

Effect of Treatment with IMOs 1 and 2 on OVA-Specific and Total Serum IgE Production in OVA-Sensitized and Challenged Mice To assess the effects of IMOs 1 and 2 on IgE production, we examined serum levels of OVA-specific and total IgE. Mice that were sensitized and challenged with OVA but not treated with IMOs 1 and 2 had high levels of OVA-specific IgE in serum (FIG. 26), while mice treated with IMOs 1 and 2 had significantly lower levels of OVA-specific IgE. Total serum IgE levels were also low in mice that received IMOs 1 and 2 treatment (FIG. 26).

Example 29

Effect of IMOs 1 and 2 Treatment on OVA-Specific and Total IgG2a Production in OVA/Alum-Sensitized-and-Challenged Mice To assess the effect of IMOs 1 and 2 treatment on IgG2a production, we examined serum levels of OVA-specific and total IgG2a. Without IMOs 1 and 2 treatment, mice sensitized and challenged with OVA had insignificant levels of OVA-specific IgG2a (FIG. 26). OVA-sensitized and -challenged mice treated with IMOs 1 and 2 had an increase in OVA-specific IgG2a antibody levels (FIG. 26). Similar results were found for serum total Ig production (FIG. 26): mice sensitized and challenged with OVA and treated with IMOs 1 and 2 had higher levels of total IgG2a than did mice that were not treated with IMOs 1 and 2.

Example 30

Figure 27:
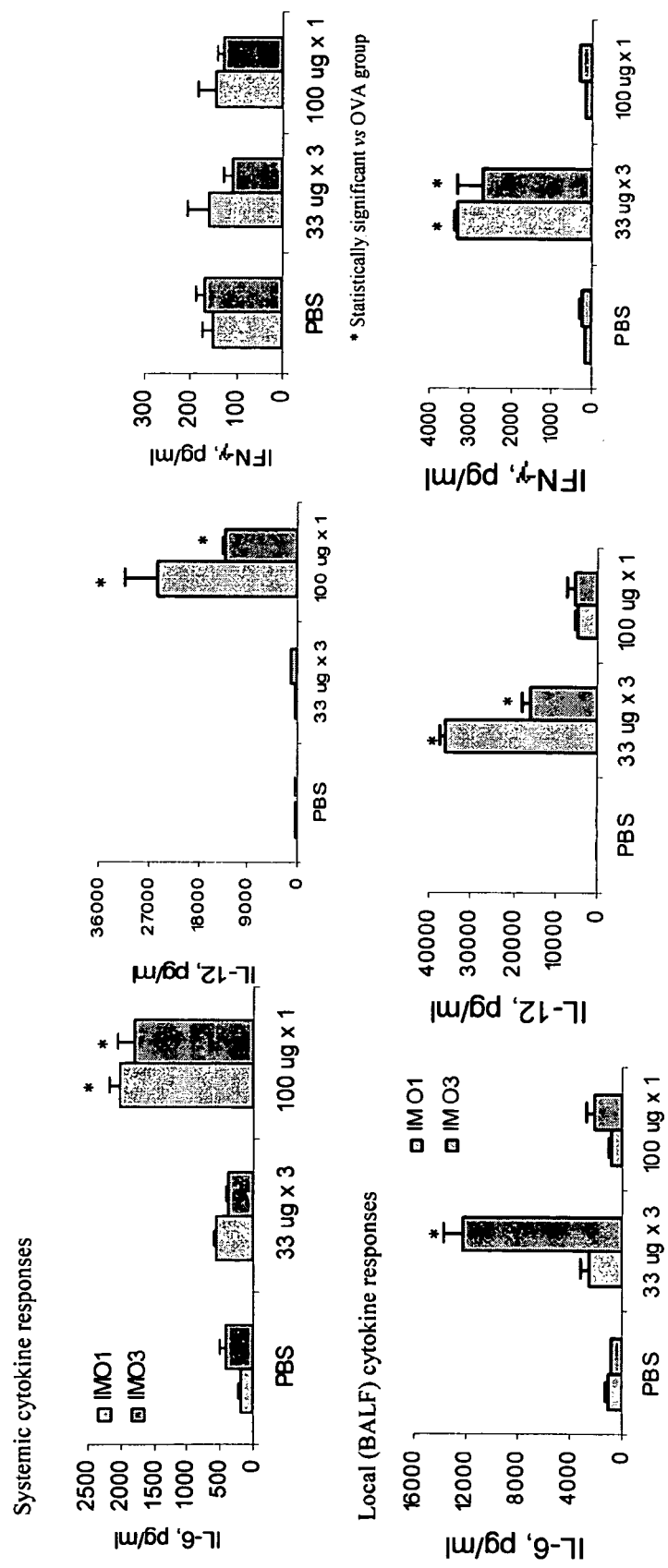
FIG. 27 shows the effect of a single high dose vs multiple lower doses of IMO compounds on local and systemic Th1 cytokine levels in naive mice. A single dose of 100 mg induced higher levels of systemic cytokine responses. On the contrary three smaller doses (3×33 mg) induced higher local (BALF) cytokine responses.

Effect of a Single High Dose vs. Multiple Lower Doses of IMO Compounds on Local and Systemic Th1 Cytokine Levels in Naïve Mice To determine the effects of dosage on IMO treatment, Mice were treated intranasally with 33 µg of IMO 1 or 3 on days 1, 2 and 3 or treated with a single intranasal administration of 100 µg of IMO 1 or 3. Mice were bled and the lungs removed 5 hours after the last treatment. A single 100 µg dose induced higher levels of systemic cytokine responses, however, the three smaller doses (3×33 µg) induced higher local (BALF) cytokine responses (FIG. 27).

Figure 28:
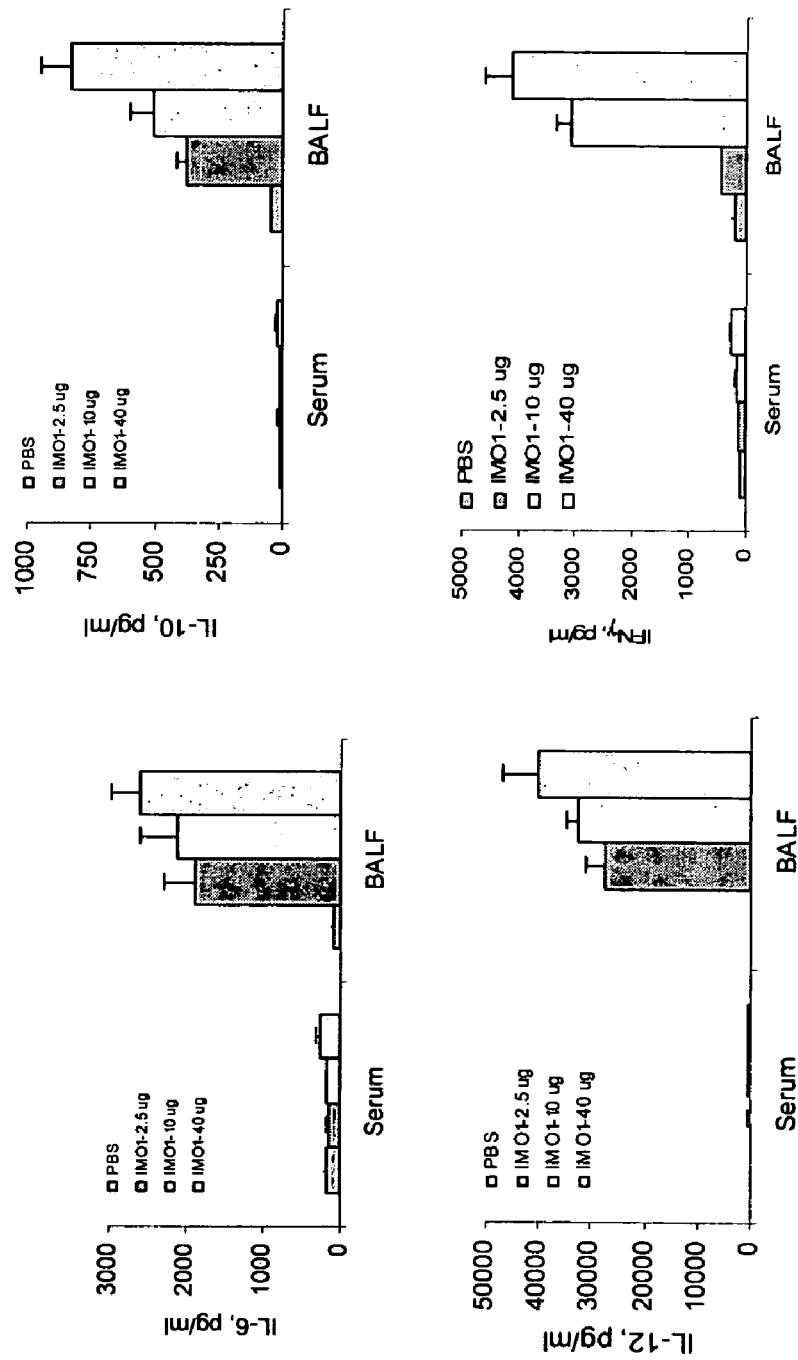
FIG. 28 shows dose-dependent effects of low multiple administrations of IMO compounds on local and systemic cytokine levels in naïve mice. IMO 1 increased local (BALF) cytokine levels but not systemic cytokine levels in mice when administered multiple times in small doses. This effect is dose-dependent.

To determine dose-dependent effects of low multiple administrations of IMO compounds on local and systemic cytokine levels in naive mice, mice were treated intranasally with 2.5 µg, 10.0 µg or 40.0 µg of IMO 1 on days 1, 2 and 3. The mice were bled and the lungs were removed 5 hours after the last treatment. IMO compounds increased local (BALF) cytokine levels but not systemic cytokine levels in mice when administered multiple times in small doses (FIG. 28). This effect was dose dependant.

Example 31

Comparison of the Effects of IMO Compounds and Corticosteriod In Vitro

Figure 29:
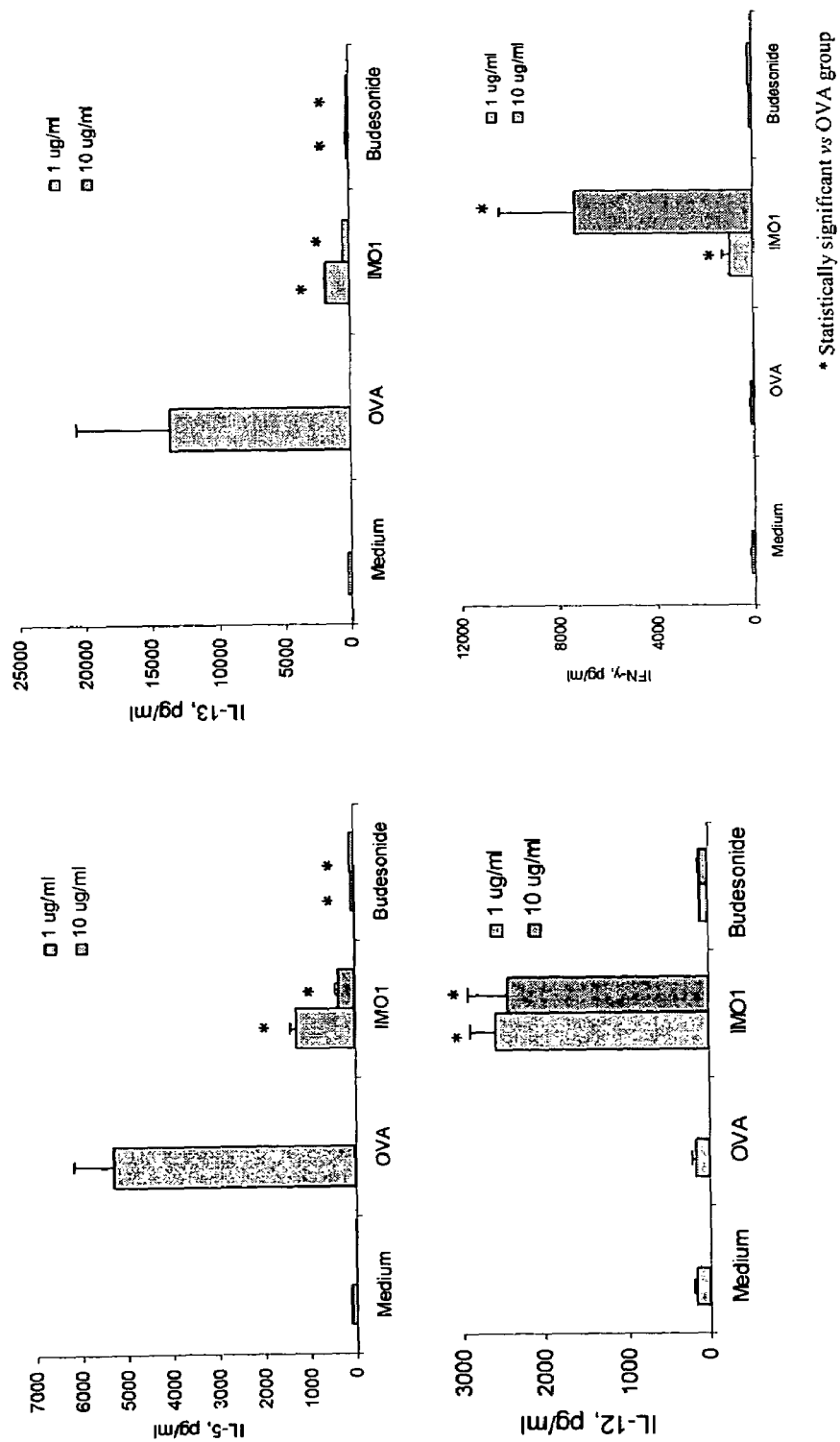
FIG. 29 compares the effects of IMO and corticosteriod in vitro. Both IMO 1 and budesonide suppressed OVA-induced Th2 cytokine secretion. However, only IMO 1 showed strong Th1 cytokine induction.

Mice were sensitized by intraperitonal (i.p.) injection of 10 mg OVA pm days 0 and 14 and challenged intranasally with 10 µg OVA in 40-µ PBS on day 28. Spleen cells were collected on day 30 and incubated with 100 µg/m OVA with or without 1 µg/ml to 10 µg/ml IMO compounds or budesonide for 72 hours. Both IMO 1 and budesonide suppressed OVA induced Th2 cytokine secretion (IL-5, ILB) (FIG. 29). However, only IMO 1 showed strong Th1 cytokine induction (IL-12, FN-8).

Equivalents

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An immunostimulatory oligonucleotide immunomer comprising at least two oligonucleotides linked by a non-nucleotide linker and having more than one 5' end, wherein the immunomer has the sequence of 5'-TCRTCRTTG-X-GT-TRCTRCT-5', wherein R is arabinoguanosine and X is glycerol linker (SEQ ID NO: 73).

2. An immunomodulatory composition comprising the immunomodulatory oligonucleotide immunomer according to claim 1; and further comprising a co-stimulatory molecule selected from the group consisting of cytokines, chemokines, protein ligands, a trans-activating factors, peptides, and peptides comprising a modified amino acid.

3. The immunomodulatory composition of claim 2, wherein the co-stimulatory molecule is conjugated to the immunomodulatory oligonucleotide immunomer.

4. The immunomodulatory composition of claim 2, further comprising an adjuvant.

5. The immunomodulatory composition of claim 2, further comprising a pharmaceutically acceptable camer.

6. An immunomodulatory composition comprising the immunomodulatory oligonucleotide immunomer according to claim 1; and further comprising an antigen.

7. The immunomodulatory composition of claim 6, further comprising an adjuvant.

8. The immunomodulatory composition of claim 6, further comprising a pharmaceutically acceptable carrier.

9. A method for modulating an immune response in a patient having airway inflammation, inflammatory disorders, allergy, or asthma comprising administering to the patient an immunomer according to claim 1.

10. The method according to claim 9, wherein the immune response is a Th1 immune response.

11. The method according to claim 9, wherein the immune response is a Th2 immune response.

12. The method according to claim 9, further comprising administering an antigen associated with said condition or disorder.

13. The method according to claim 12, wherein the immunomer or the antigen, or both, are linked to an immunogenic protein or non-immunogenic protein.

14. A method for modulating an immune response in a patient having airway inflammation, inflammatory disorders, allergy, or asthma comprising administering to the patient an immunomer according to claim 2.

* * * * *

```
                            SEQUENCE LISTING

<160> NUMBER OF SEQ ID NOS: 93

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagaacgctc gacctt                                                     16

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctatctgacg ttctctgt                                                   18

<210> SEQ ID NO 3
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 3
tgacgttctc tgt                                                          13

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 5OHdC

<400> SEQUENCE: 4
ctatctgang ttctctgt                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG

<400> SEQUENCE: 5
ctatctgacn ttctctgt                                                     18

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 6
ctgangttct ctgt                                                         14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 7
ctgacnttct ctgt                                                         14

<210> SEQ ID NO 8
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctgacgttct ctgt                                                        14

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside

<400> SEQUENCE: 9
nntgacgttc tctgt                                                       15

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 10
nnntgacgtt ctctgt                                                      16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (7)
<223> OTHER INFORMATION: 5OHdC

<400> SEQUENCE: 11
nnntgangtt ctctgt                                                      16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
```

```
<222> LOCATION: (8)
<223> OTHER INFORMATION: 7-deaza-dG

<400> SEQUENCE: 12
nnntgacntt ctctgt                                                    16

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tctgacgttc t                                                         11

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 14
nnntctgacg ttct                                                      14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (9)
<223> OTHER INFORMATION: 5OHdC

<400> SEQUENCE: 15
nnntctgang ttct                                                      14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (10)
<223> OTHER INFORMATION: 7-deaza-dG

<400> SEQUENCE: 16
nnntctgacn ttct                                                      14
```

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctatctgtcg ttctctgt                                                      18

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 18
tctgtcnttc t                                                             11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 19
tctgtcnttc t                                                             11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 20
tctgtnnttc t                                                             11

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)

```
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 21
nntctgtcnt tct                                                      13

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester linkage
<220> FEATURE:
<221> NAME/KEY: modified_base
<222> LOCATION: (6)
<223> OTHER INFORMATION: AraG

<400> SEQUENCE: 22
ctgtcnttct ctgt                                                     14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester linkage
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG

<400> SEQUENCE: 23
ctgtnnttct ctgt                                                     14

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 24
tctgacnttc t                                                        11

<210> SEQ ID NO 25
<211> LENGTH: 13
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 25
nntctgacnt tct                                                          13

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 26
tctgacnttc t                                                            11

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 27
tctgannttc t                                                            11

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester linkage
<220> FEATURE:
<221> NAME/KEY: modified_base
<222> LOCATION: (5)
<223> OTHER INFORMATION: AraC

<400> SEQUENCE: 28
ctgangttct ctgt                                                         14

<210> SEQ ID NO 29
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester linkage
<220> FEATURE:
<221> NAME/KEY: modified_base
<222> LOCATION: (6)
<223> OTHER INFORMATION: AraG

<400> SEQUENCE: 29
ctgacnttct ctgt                                                              14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester linkage
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG

<400> SEQUENCE: 30
ctgannttct ctgt                                                              14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctgtcgttct ctgt                                                              14

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctgtcgttct ct                                                                12

<210> SEQ ID NO 33
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tctgtcgttc t                                                                 11
```

```
<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctcactttcg ttctctgt                                                  18

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ctttcgttct ctgt                                                      14

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctttcgttct ct                                                        12

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 37
tctttngttc t                                                         11

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 38
tctttcnttc t                                                         11

<210> SEQ ID NO 39
<211> LENGTH: 11
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 39
tctgtngttc t                                                                11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 40
tctgangttc t                                                                11

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgacgttct                                                                  10

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: dGdeaza
<220> FEATURE:
<221> NAME/KEY: modified_base
<222> LOCATION: (18)
<223> OTHER INFORMATION: dGdeaza

<400> SEQUENCE: 42
tctgtcgttc ttctgtcgtt ct                                                    22

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctgtcgttct ctgtctgtcg ttctctgt                                              28

<210> SEQ ID NO 44
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-ribonucleoside
<220> FEATURE:
<221> NAME/KEY: modified_base
<222> LOCATION: (16)..(17)
<223> OTHER INFORMATION: 2'-OMe-ribonucleoside

<400> SEQUENCE: 44
nntgtcgttc tctgtnntgt cgttctctgt                                        30

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tccatgacgt tcctgatgc                                                    19

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccatgacgtt cctgatg                                                      17

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tccatgacgt tcctgatg                                                     18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccatgacgtt cctgatgc                                                     18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 49
cctactagcg ttctcatc                                                    18

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gcgttctcat c                                                           11

<210> SEQ ID NO 51
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tagcgttctc atc                                                         13

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tactagcgtt ctcatc                                                      16

<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cctactagcg t                                                           11

<210> SEQ ID NO 54
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctactagcg ttc                                                         13

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

```
ctagcgttct catc                                                    14

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cgttctctgt                                                         10

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gacgttctct gt                                                      12

<210> SEQ ID NO 58
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctatctgacg ttc                                                     13

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cgttctctgt                                                         10

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
acgttctctg t                                                       11

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
```

```
ctatctgacg                                                            10

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctatctgacg t                                                          11

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctatctgacg tt                                                         12

<210> SEQ ID NO 64
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 ctgt                                                                   4

<210> SEQ ID NO 65
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65 tcgtcgtt                                                               8

<210> SEQ ID NO 66
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: 2'-OMe-ribonucleotide

<400> SEQUENCE: 66
cagagcucug                                                            10

<210> SEQ ID NO 67
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 67 tcntcntt                                                                8

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cagagctctg                                                             10

<210> SEQ ID NO 69
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphodiester

<400> SEQUENCE: 69 tcgtcgtt                                                                8

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphodiester

<400> SEQUENCE: 70
cagagctctg                                                             10

<210> SEQ ID NO 71
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphodiester
<220> FEATURE:
<221> NAME/KEY: misc_feature
<222> LOCATION: (1)..(10)
<223> OTHER INFORMATION: 2'-OMe-ribonucleotide

<400> SEQUENCE: 71
```
cagagcucug                                                              10

<210> SEQ ID NO 72
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 72 tcntcnttg                                                               9

<210> SEQ ID NO 73
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (6)
<223> OTHER INFORMATION: AraG

<400> SEQUENCE: 73 tcntcnttg                                                               9

<210> SEQ ID NO 74
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74 ttgtgcttg                                                               9

<210> SEQ ID NO 75
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75 tcgtcgttg                                                               9

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<221> NAME/KEY: modified_base
<222> LOCATION: (6)
<223> OTHER INFORMATION: Arabinoguanosine

<400> SEQUENCE: 76
ctgtcnttct c                                                            11

<210> SEQ ID NO 77
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 1-(2'-deoxy-b-D-ribofuranosyl)-2-oxo-7-deaza-8-
      methyl-purine

<400> SEQUENCE: 77
tctgtngttc t                                                            11

<210> SEQ ID NO 78
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 ctat                                                                     4

<210> SEQ ID NO 79
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79 cta                                                                      3

<210> SEQ ID NO 80
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80 cctactagc                                                                9

<210> SEQ ID NO 81
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81 ttctcatc                                                                 8
```

```
<210> SEQ ID NO 82
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 cctact                                                              6

<210> SEQ ID NO 83
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 ccta                                                                4

<210> SEQ ID NO 84
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84 cct                                                                 3

<210> SEQ ID NO 85
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85 ctcatc                                                              6

<210> SEQ ID NO 86
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86 catc                                                                4

<210> SEQ ID NO 87
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87 atc                                                                 3

<210> SEQ ID NO 88
```

-continued

```
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88 ctatc                                                                      5

<210> SEQ ID NO 89
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89 ctgt                                                                       4

<210> SEQ ID NO 90
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90 ctatct                                                                     6

<210> SEQ ID NO 91
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91 tctctgt                                                                    7

<210> SEQ ID NO 92
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92 ctctgt                                                                     6

<210> SEQ ID NO 93
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 tctgt                                                                      5
```